US008137661B2

(12) United States Patent
Spencer, Jr. et al.

(10) Patent No.: US 8,137,661 B2
(45) Date of Patent: Mar. 20, 2012

(54) CONTROLLED RELEASE INTERFERON DRUG PRODUCTS AND TREATMENT OF HCV INFECTIONS USING SAME

(75) Inventors: David Gelvin Spencer, Jr., Chapel Hill, NC (US); John Elliott Humphries, Chapel Hill, NC (US); Leonardus Gerardus Jozef De Leede, HM Waddinxveen (NL); Rudolf Verrijk, HS Noordwijk (NL)

(73) Assignee: Biolex Therapeutics, Inc., Pittsboro, NC (US)

( * ) Notice: Subject to any disclaimer, the term of this patent is extended or adjusted under 35 U.S.C. 154(b) by 297 days.

(21) Appl. No.: 12/180,214

(22) Filed: Jul. 25, 2008

(65) Prior Publication Data

US 2009/0068280 A1 Mar. 12, 2009

Related U.S. Application Data

(60) Provisional application No. 60/951,879, filed on Jul. 25, 2007, provisional application No. 60/952,140, filed on Jul. 26, 2007, provisional application No. 60/978,330, filed on Oct. 8, 2007, provisional application No. 60/985,526, filed on Nov. 5, 2007.

(51) Int. Cl.
*A61K 38/21* (2006.01)
(52) U.S. Cl. ............... 424/85.7; 424/85.5; 514/1.1
(58) Field of Classification Search ............ None
See application file for complete search history.

(56) References Cited

U.S. PATENT DOCUMENTS

| | | | |
|---|---|---|---|
| 4,749,576 A | 6/1988 | Lee | |
| 5,980,948 A | 11/1999 | Goedemoed et al. | |
| 6,117,423 A | 9/2000 | Berg | |
| 6,153,211 A | 11/2000 | Hubbell et al. | |
| 6,172,046 B1 | 1/2001 | Albrecht | |
| 6,299,872 B1 | 10/2001 | Albrecht et al. | |
| 6,387,365 B1 | 5/2002 | Albrecht et al. | |
| 6,461,605 B1 | 10/2002 | Cutler et al. | |
| 6,465,425 B1 | 10/2002 | Tracy et al. | |
| 6,472,373 B1 | 10/2002 | Albrecht | |
| 6,482,613 B1 | 11/2002 | Goeddel et al. | |
| 6,610,830 B1 | 8/2003 | Goeddel et al. | |
| 6,703,037 B1 | 3/2004 | Hubbell et al. | |
| 6,815,184 B2 | 11/2004 | Stomp et al. | |
| 6,835,557 B1 | 12/2004 | Weissmann | |
| 7,208,167 B2 * | 4/2007 | Rudolph | 424/278.1 |
| 7,736,674 B2 * | 6/2010 | Bechet et al. | 424/489 |
| 7,867,518 B2 * | 1/2011 | Bechet et al. | 424/489 |
| 2003/0203039 A1 | 10/2003 | Lyons et al. | |
| 2003/0206928 A1 | 11/2003 | Tormala et al. | |
| 2005/0269364 A1 | 12/2005 | Gibson | |
| 2006/0257365 A1 | 11/2006 | Albrecht | |
| 2007/0021434 A1 | 1/2007 | Boyd et al. | |
| 2007/0128162 A1 | 6/2007 | Dickey et al. | |

FOREIGN PATENT DOCUMENTS

| | | |
|---|---|---|
| EP | 0707855 | 4/1996 |
| EP | 0830859 | 3/1998 |
| EP | 0903148 | 3/1999 |
| EP | 0956861 | 11/1999 |
| EP | 1005868 | 6/2000 |
| EP | 1136075 | 9/2001 |
| EP | 1213029 | 6/2002 |
| EP | 1247522 | 10/2002 |
| EP | 1317929 | 6/2003 |
| EP | 1679065 | 7/2006 |
| WO | WO 97/16204 | 5/1997 |
| WO | WO 02/09675 | 2/2002 |
| WO | WO 03/041689 | 5/2003 |
| WO | WO 2004/067563 | 8/2004 |
| WO | WO 2006/011792 | 2/2006 |
| WO | WO 2006/085747 | 8/2006 |

OTHER PUBLICATIONS

Bizollon, Thierry, et al., "Pilot study of the combination of interferon alfa and ribavirin as therapy of recurrent hepatitis C after liver transplant", Hepatology, 1997, p. 500-504, vol. 26.
Braconier, Jean Henrik, et al., "Combined alpha-interferon and ribavirin treatment in chronic hepatitis C: a pilot study", Scan J. Infect. Dis, 1995, p. 325-329, vol. 27.
Chemello, Liliana, et al., "The effect of interferon alfa and ribavirin combination therapy in naïve patients with chronic hepatitis C", Journal of Hepatology, 1995, p. 8-12, vol. 23, Suppl. 2.
Conensus Statement, "EASL International Consensus Conference on Hepatitis C", Journal of Hepatitis C, 1999, p. 956-961, vol. 30.
De Leede et al., Novel Controlled-release interferon Lemna-Derived IFN-α2b- (Locteron): Pharmacokinetics, Pharmacodynamics, and Tolerability in a Phase 1 Clinical Trial , Journal of Interferon & Cytokine research, 2008, p. 113-122, vol. 28.
Dusheiko, Geoffrey, "Side effects of alpha interferon in chronic hepatitis C", Hepatology, 1997, p. 112S-121S, vol. 26, No. 3, Suppl. 1.
Formann E., et al., "Twice-weekly administration of peginterferon-α-2b improves viral kinetics in patients with chronic hepatitis C genotype 1", Journal of Viral Hepatitis, 2003,p. 271-276, vol. 10.
Herrmann, Eva, et al., "The kinetics of hepatitis C virus", European Journal of Gastroenterology & Hepatology, 2006, vol. 18, No. 4, p. 339-342.
Herrmann, Eva, et al., "Viral kinetics in patients with chronic hepatitis C treated with serine protease inhibitor BILN 2061", Antiviral Therapy, 2006, p. 371-376, vol. 11.
Kasahara, Akinori, et al., "Ability of prolonged interferon treatment to suppress relapse after cessation of therapy in patients with chronic hepatitis C: a multicenter randomized controlled trial", Hepatology, 1995, p. 291-297, vol. 21, No. 2.
Lai, Ming-Yang et al., "Long term efficacy of ribavirin plus interferon alfa in the treatment of chronic hepatitis C", Gastroenterology, 1996, p. 1307-1312, vol. 111, No. 5.

(Continued)

*Primary Examiner* — Daniel C Gamett
(74) *Attorney, Agent, or Firm* — Brinks Hofer Gilson & Lione

(57) ABSTRACT

The invention relates to controlled release formulations comprising a microparticle comprising a biodegradable polymer and one or more interferon compounds and methods of using the formulations.

9 Claims, 22 Drawing Sheets

OTHER PUBLICATIONS

Lindsay, Karen L., et al., "Response to higher doses of interferon alpha-2b in patients with chronic hepatitis C: a randomized multicenter trial", Hepatology, 1996, p. 1034-1040, vol. 24, No. 5.

Reichard, Olle, et al., "Therapy of hepatitis C: Alpha interferon and ribavirin", Hepatology, 1997, pp. 109S-111S, vol. 26, No. 3.

Octoplus Prospectus, Aug. 31, 2006 (excerpt).

Octoplus Prospectus, Aug. 31, 2006 (full).

Biolex Press Release, "Biolex Therapeutics Announces Initiation of Locteron™ Phase 2 Clinical Study in Chronic Hepatitis C," dated Jan. 30, 2007.

Octoplus Press Release dated Jan. 30, 2007.

Hoogdalem et al., "Pharmacokinetics, Safety and Biomarkers in Man after Administration of Locteron™, a Once every Two Weeks Controlled Release Formulation of IFNa2b," presented at the EASLD Meeting, Vienna, Apr. 2006.

Weigand, Kilian et al., "Treatment of hepatitis C virus infection", World J. Gastroenterol., 2007, p. 1897-1905, vol. 13, No. 13.

Written Opinion, dated Dec. 18, 2008, issued in co-pending International Application No. PCT/US2008/71191,filed Jul. 25, 2008.

International Preliminary Report on Patentability, issued in PCT/US2008/071191, dated Feb. 4, 2010.

Zeuzem et al., "Antiviral Response at Week 12 Following Completion of Treatment with Albinterferon α-2b Plus Ribavirin in Genotype 1, IFN-Näive, Chronic Hepatits C Patients," Journal of Hepatology, vol. 46, Supplement No. 1, (2007), p. S293.

Ferenci et al., "Predicting Sustained Virological Responses in Chronic Hepatitis C Patients Treated with Peginterferon alfa-2a (40 KD)/Ribavirin," Journal of Hepatology, vol. 43, (2005), pp. 425-433.

Kontsek et al., "The Human Interferon System: Characterization and Classification after Discovery of Novel Members," Acta Virologica, vol. 47, (2003), pp. 201-215.

Marcellin et al., "Virological Response at 4 and 12 Weeks Predict High Rates of Sustained Virological Response in Genotype 1 Patients Treated with Peginterferon alfa-2a (40KD) plus Ribavirin," Conference Reports for NATAP, 42nd Meeting of the European Association for the Study of the Liver (EASL), (Apr. 11-15, 2007), Barcelona, Spain.

Marcellin et al., "Host and Viral Baseline Characteristics in Hepatitis C Naïve and Non-Responder Patients: Comparison of Three Large Randomised Multinational Trials," Journal of Hepatology, Supplement No. 2, vol. 44, Posters, (2006), p. S232.

Napoli et al., "A Pegylated Interferon Alpha-2b Dose-Reduction in HCV 1b Patients with Rapid Virological Response does not Affect Sustained Virological Response," Journal of Hepatology, Abstracts of the 42nd Annual Meeting of EASL, Supplement No. 1, vol. 46, (2007), p. S225.

Zeuzem et al., "Interim (Week 12) Phase 2B Virological Efficacy and Safety Results of Albuferon (albumin interferon alfa-2b) Combined with Ribavirin in Genotype 1 Treatment-naïve Chronic Hepatitis C Infection," Conference Reports for NATAP, 41st Meeting of the European Association for the Study of Liver Diseases, (Apr. 26-30, 2006), Vienna, Austria.

Zeuzem et al., "Optimal Pre-Treatment HCV RNA Level for Prediction of SVR with Peginterferon alfa-2a (40KD) (PEGASYS) plus Ribavirin (COPEGUS) in Genotype 1 Pateints: Generalised Additive Logistic Regression Model (GAM) Analysis," Conference Reports for NATAP, 42nd Meeting of the European Association for the Study of Liver Diseases (EASL), (Apr. 11-15, 2007), Barcelona, Spain.

PEG-INTRON product label, Schering Coporation, SCH 54031, Section 2, copyright 2000, pp. 1-20.

PEGASYS product label, Roche Pharmaceuticals, RAPID v4.5, copyright 2003-2005, pp. 1-46.

Bain et al., "A Phase 2 Study to Evaluate the Antiviral Activity, Safety, and Pharmacokinetics of Recombinant Human Albumin-Interferon Alfa Fusion Protein in Genotype 1 Chronic Hepatitis C Patients," Journal of Hepatology, vol. 44, (2006), pp. 671-678.

Conference Reports for NATAP, "58th Annual Meeting of the American Association for the Study of Liver Diseases (AASLD)," (Nov. 2-6, 2007), Boston, MA.

Crommelin et al., "Pharmaceutical Biotechnology," Harwood Academic Publishers, (1997), pp. 219-222.

Davis et al., "Early Virologic Response to Treatment with Peginterferon Alfa-2b plus Ribavirin in Patients with Chronic Hepatitis C," Heptatology, vol. 38, (2003), pp. 645-652.

De Leede et al., "Novel Controlled-Release Lemna-Derived IFN-α2b (Locteron): Pharmacokinetics, Pharmacodynamics, and Tolerability in a Phase I Clinical Trial," Journal of Interferon & Cytokine Research, vol. 28, (2008), pp. 113-122.

Sherman et al., "Clinical Need and Therapeutic Targets for New HCV Agents," Copyright 2007, Clinical Care Options, LLC, pp. 1-13.

Signals Online Magazine, "Race to Cure HCV Infection Heats Up," (May 31, 2007), pp. 1-15.

Smith, "Hepatitis C Virus Therapies," Nature Reviews, vol. 5, (Sep. 2006), pp. 715-716.

Trepo et al., "Novel Sustained Release Formulation of IFN-alfa-2b-XL, Improves Tolerability and Demonstrates Potent Viral Load Reduction in a Phase I/II HCV Clinical Trial," Flamel Presentation, pp. 1-19, 12th International Symposium on Viral Hepatitis and Liver Disease, Jul. 3, 2006.

* cited by examiner

Key:
filled circles: average cumulative in vitro release of IFN from phase 2 formulation;
filled squares: average cumulative in vitro release of IFN from phase 1 formulation Percentage of Patients After 12-Weeks of Treatment
With Clinical Adverse Events Rated As Severe

CONTROLLED RELEASE INTERFERON DRUG PRODUCTS AND TREATMENT OF HCV INFECTIONS USING SAME

This application claims the benefit of U.S. Provisional Application Nos. 60/951,879, filed Jul. 25, 2007; 60/952,140, filed Jul. 26, 2007; 60/978,330, filed Oct. 8, 2007; and 60/985,526, filed Nov. 5, 2007; the entire content of each of these applications is hereby incorporated by reference herein.

FIELD

The invention pertains to controlled release interferon drug products as well as to the treatment of HCV (hepatitis C virus) infection by interferon therapy.

BACKGROUND

With an estimated 170 million people worldwide infected with the hepatitis C virus (HCV), chronic hepatitis C infection is an important global health problem. HCV infection is the principal cause of chronic liver disease and hepatocellular carcinoma and the leading indication for liver transplantation in the United States and Western Europe. The only marketed products that have shown to eradicate HCV are interferons, either in mono- or in combination therapy.

The hepatitis C virus is unique in that it is a single-stranded, RNA-based virus that targets hepatocytes for infection and replication of new virions. About 4-8 weeks after the initial HCV infection, acute elevations of hepatic transaminase levels in serum are often noted, signalling that inflammation in the liver is occurring. Approximately 80% of patients with HCV infection progress to more chronic liver disease. Further progression of the disease leads to scarring or fibrosis, and cirrhosis in the affected regions of the liver in approximately 20 to 50% of infected patients between 10 to 20 years after the initial infection. A number of patients with chronic HCV infection may also progress to primary hepatocellular carcinoma.

Human recombinant IFNα2b is approved in many countries for the treatment of hepatitis B and C infection, either as a monotherapy or in combination with ribavirin. In addition, it is also approved in many countries for treating patients with cancer. IFNα2b is available as Intron® A (Schering), which needs to be administered three times a week due to the relatively short half life of 2-3 h after subcutaneous (SC) injection. A longer-acting version of IFNα2b has been developed, by polyethylene glycol modification of the molecule. Pegylated IFNα2b (PEGIntron®) is only approved for the treatment of hepatitis C. Its half-life is about 40 h and it is administered once weekly by SC injection. However, PEGIntron®, being a modified IFNα2b molecule, compared to unpegylated INFα2b, it has reduced affinity for the IFNα2b receptor, distributes differently in the body and hence its safety and efficacy are not necessarily comparable to IFNα2b.

Other long-acting INF therapies are under development. Like PEG-Intron these are not based on controlled release of INF, but on a prolonged half-life owing to delayed clearance.

In current methods of treating HCV infection, the goal is SVR (sustained viral response), which is defined as finding no detectable HCV 24 weeks after completion of therapy. It is recognized that predictive factors for SVR are EVR (early viral response), which may be described as at least a 2 log drop in serum HCV RNA level compared to baseline (pre-treatment level) after 12 weeks of treatment, and, increasingly, RVR (rapid viral response), which is defined as no detectable HCV after 4 weeks of treatment. Additionally, these predictive factors are important per se, as not all patients respond to INF (combined) therapy, and it is therefore preferred to have an indication of response at an early point in time during therapy, e.g. to avoid the adverse events and expense of futile therapy.

INF therapy, particularly at higher doses as is known from cancer treatment, is frequently accompanied by uncomfortable or even inhibitory side effects.

Desires in HCV infection therapy are, inter alia, obtaining an improved RVR and/or EVR, a better side effect profile, and/or a better ratio between therapeutic effect and side effects.

SUMMARY

This invention relates to controlled release formulations comprising a microparticle comprising a biodegradable polymer and one or more interferon compounds and methods of using the formulation to treat hepatitis C. In one embodiment, the one or more interferon compounds are released from the microparticle in a sigmoidal pattern. In another embodiment, the microparticle is a microsphere. In certain embodiments, the one or more interferon compounds are encapsulated by or dispersed in the biodegradable polymer. The biodegradable polymer may be a block copolymer comprising a poly(ethylene glycol terephthalate) segment and a poly(butylene terephthalate) segment wherein the block copolymer may comprise about 50 wt % to about 85 wt % poly(ethylene glycol terephthalate) comprising polyethylene glycol segments having 100-10,000 g/mole weight average molecular weight. In certain embodiments, the glycol segments have 400-5,000 g/mole, 1,000-2,000 g/mole, or about 1,500 g/mole weight average molecular weight. In other embodiments, the block copolymer comprises about 70 wt % to about 85 wt % poly(ethylene glycol terephthalate). In aspect, the block copolymer comprises about 77 wt % poly(ethylene glycol terephthalate) comprising polyethylene glycol segments having about 1,500 g/mole weight average molecular weight. In further embodiments, the one or more interferon compounds is interferon-α2b present in an amount of about 100 µg to about 1000 µg per dose or it may constitute about 0.2 wt % to about 10 wt %, about 0.2 wt % to about 5 wt %, or about 2-6 wt % of the microparticle.

Further aspects of the invention include a method of preventing adverse events induced by or associated with administration of interferon to a human infected with hepatitis C comprising administering to said human a controlled release formulations of the present invention. In one aspect, the invention involves a method of treating acute or chronic hepatitis C comprising administering to a subject in need thereof a controlled release formulation of the present invention. In another aspect, the adverse event is a flu-like symptom. In a further aspect, the flu-like symptom is arthralgia, chills, pyrexia, headache or myalgia.

In some aspects, the Cmax of the one or more interferon compounds in the blood plasma is reached after about 48 hours after initial administration of the formulation. In other aspects, the one or more interferon compounds are released from the microparticle in a sigmoidal pattern. In further aspects, the formulation may be administered no more than once every two weeks.

In some embodiments, the interferon-α2b is a C-terminally truncated interferon. In other embodiments, less than 5% of the subjects experience adverse severe events. In further embodiments, greater than 80% of the flu-like symptoms that occur in the subjects are mild. In one embodiment, pyrexia occurs in less than 25% of the subjects. In another embodiment, at least 80%, at least 90%, at least 95%, at least 98%, or at least 99% of the subjects exhibit more than two log reduction in HCV RNA 12 weeks after initial administration.

In certain embodiments, the formulation may be administered in combination with one or more additional therapeutic agents, for example, a nucleoside antimetabolite drug or analogue, a reverse transcriptase inhibitor, a viral polymerase inhibitor, a viral protease inhibitor, an internal ribosome entry site (IRES) inhibitor, a viral helicase inhibitor, a viral fusion inhibitor, a viral entry inhibitor, an integrase inhibitor, an antisense compound, an RNA interference agent, a ribozyme, a cytochrome P450 monooxygenase inhibitor, a hematopoietin, a therapeutic vaccine, a monoclonal or polyclonal antibody, a non-nucleoside inhibitor, an alpha-glucosidase inhibitor, an interferon enhancer, an interleukin, a glucocoritoid, an anti-inflammatory, a cyclophilin inhibitor, a P7 protein inhibitor, a tubulin inhibitor, a TNF agonist, a TLR agonist, an immunosupressant, immunomodulatory compound, or any combination thereof. In further embodiments, the formulation may be administered in combination with one or more additional therapeutic agents, for example, ribavirin, Levovirin, VP-50406, ISIS 14803, VX 497, Thymosin, Maxamine™, mycophenolate mofetil, Telaprevir, Valopicitabine, Boceprevir, IC41 Therapeutic vaccine, AVI-4065 Antisense, VGX-410C IRES inhibitor, INN-0101 Therapeutic vaccine, R1626 Polymerase inhibitor, XTL-6865 ab86-ab65 monoclonal antibody, HCV-796 Non-Nucleoside Polymerase inhibitor, GS9132/ACH806 Protease inhibitor, GI 5005 Therapeutic vaccine, Hemopurifier, XTL-2125 Non-Nucleoside Polymerase inhibitor, SIRNA-034, RNA interference TT033, R7128 nucleoside polymerase inhibitor, A-831 NS5A inhibitor, therapeutic vaccine ED-002, NV-08, Protease inhibitor ITMN0191, BCX-4678, GL59728 non-nucleoside and nucleoside polymerase inhibitor, GL60667 non-nucleoside and nucleoside polymerase inhibitor, Hepavaxx C, HuMax-HepC, A-689 NS5a Inhibitor, Pradefavir, N-nucleoside polymerase inhibitor, small molecule polymerase inhibitor, IRES inhibitor, helicase inhibitor, Fuzeon, protease/polymerase inhibitor, N3 3/4A protease inhibitor, polymerase inhibitor, protease inhibitor, small molecules, small molecule compounds, RNAi compounds, entry inhibitor, ACH-1095 protease inhibitor, ANA598 Non-nucleoside polymerase inhibitor, MX3235 Celgosivir alpha-glucosidase I inhibitor, Actilon CPG-TLR9 Agonist, Civacir, Suvus, IET Interferon Enhancing Therapy, Alinia, KPE02003002, ANA975 prodrug of TLR7 antagonist, Bavituximab, ECH18 Immune Regulator, Immu 105, Nov-205, IMO-2125, KPE00001133, AN 025-1, JKB-122, Mito-Q, oral Belerofon, Debio 025, protease inhibitor, BILN2061 protease inhibitor, Therapore immuno-therapy, Heptazyme, ISIS-14803 antisense, VP50406, translation inhibitor, Gene Regulating targets, R803, UT231B, R1479, IMPDH inhibitor VX497, IDN-6556, or any combination thereof.

BRIEF DESCRIPTION OF THE DRAWINGS/FIGURES

FIGS. 1A-1C show individual HCV RNA log reduction for 32 study subjects. FIG. 1D shows Kaplan-Meier analysis of first times ≧2 log10 reduction in HCV RNA level for the four dose groups. FIG. 1E shows Kaplan-Meier analysis of first times to HCV RNA eradication for the four dose groups.

Figure 9A:
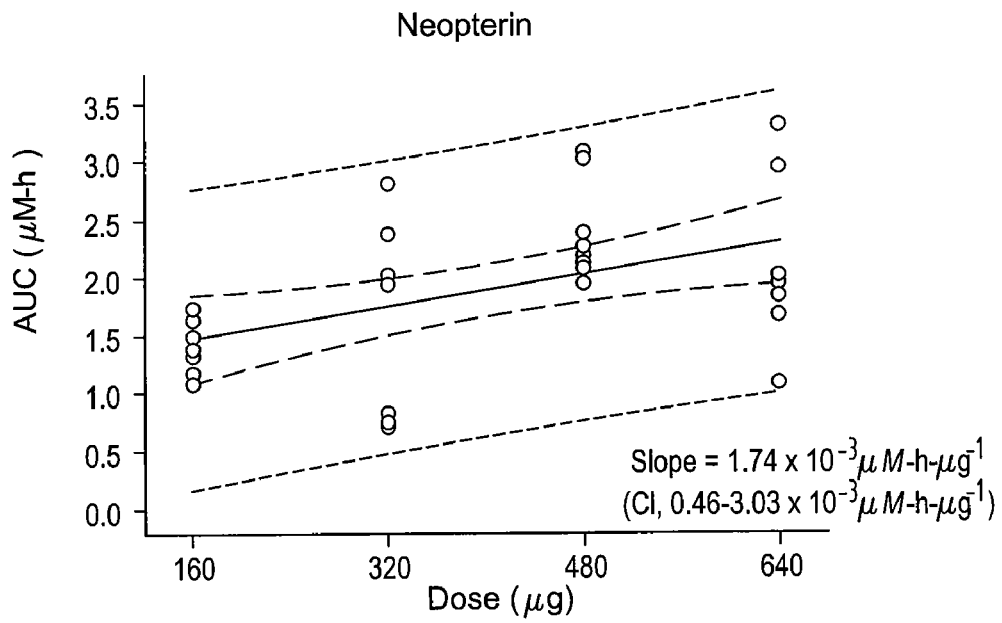
Figure 9B:
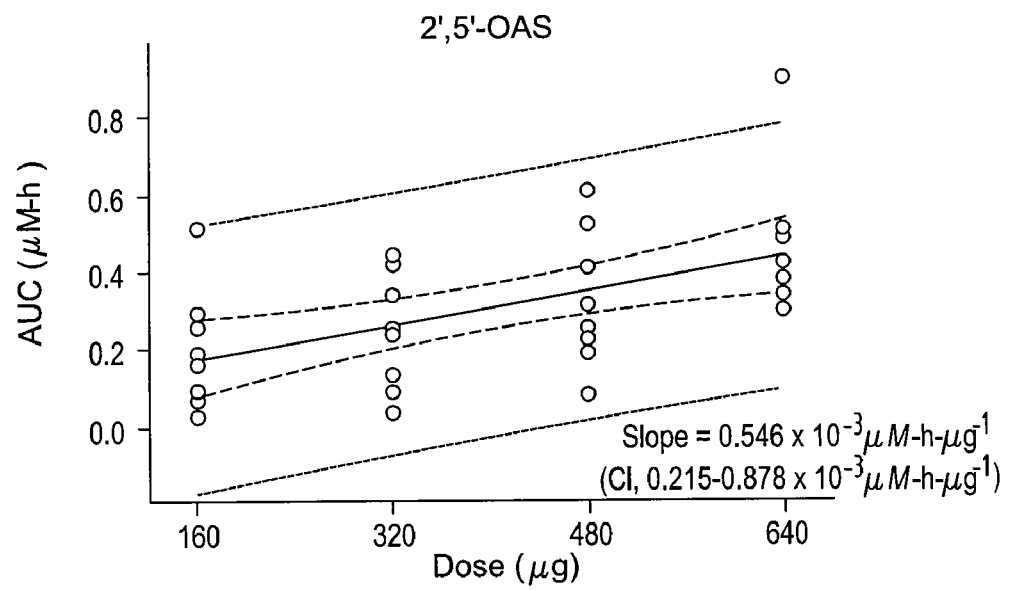

FIGS. 9a and 9b show linear regression analysis of (a) neopterin and (b) 2,5-OAS AUC as a function of LOCTERON dose. Data points depict individual patient AUC values. Dashed lines indicate the 95% confidence intervals of the regressions and dotted lines the 95% prediction intervals for new observations. Abbreviations: AUC, area under the time-concentration curve; CI, 95% confidence interval.

Figure 10:
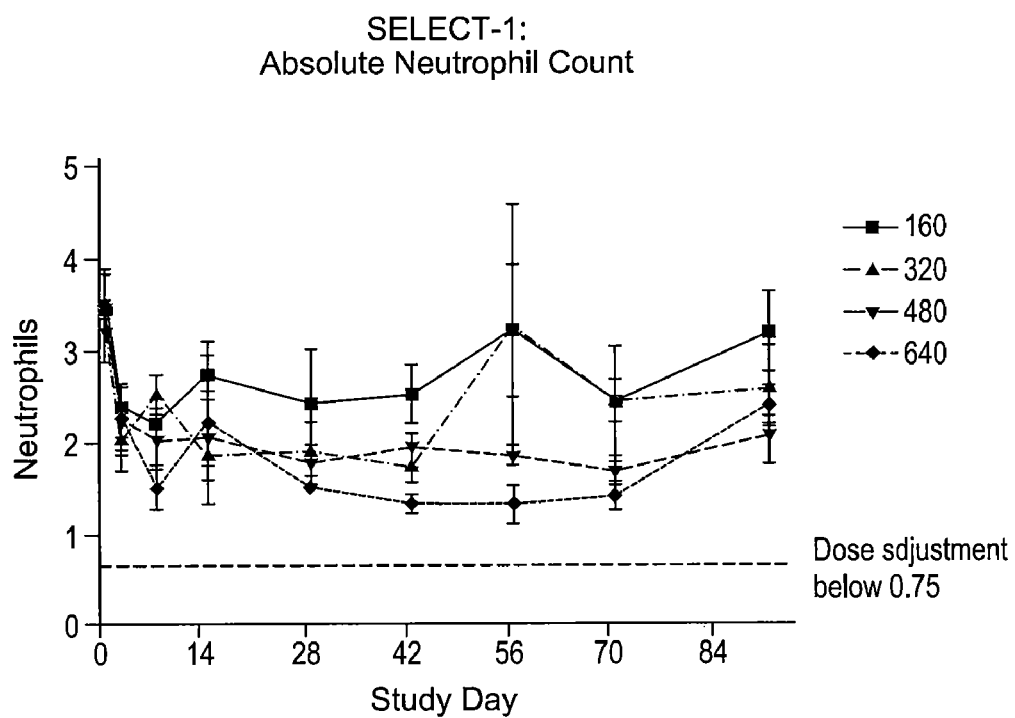

FIG. 10 shows absolute neutrophil count for the treatment group.

Figure 11:
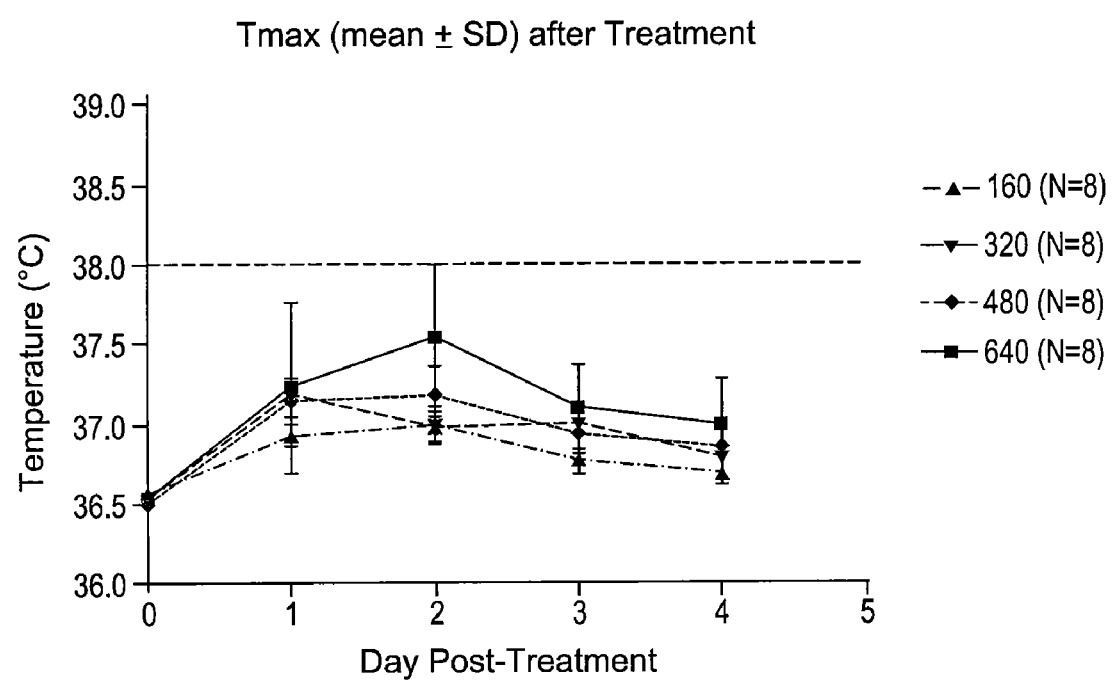
Figure 12:
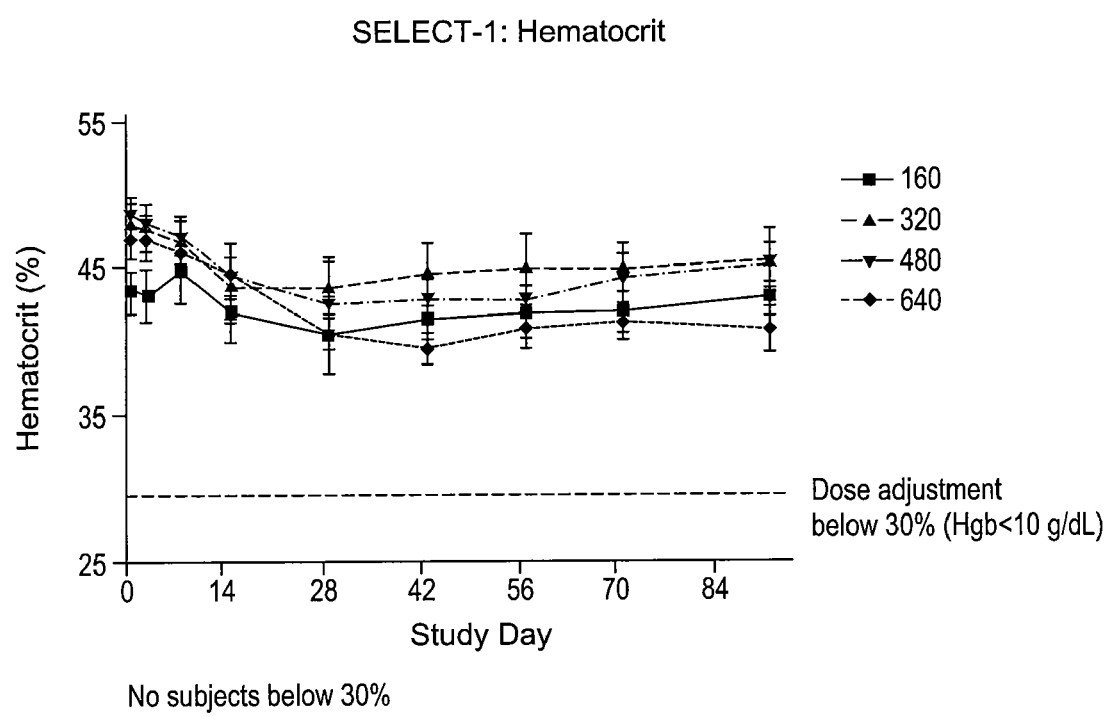

FIG. 11 shows mean body temperature for the four cohorts during the first few days after initial administration of LOCTERON FIG. 12 shows hematocrit for study cohorts. No subject fell below 30%.

Figure 13:
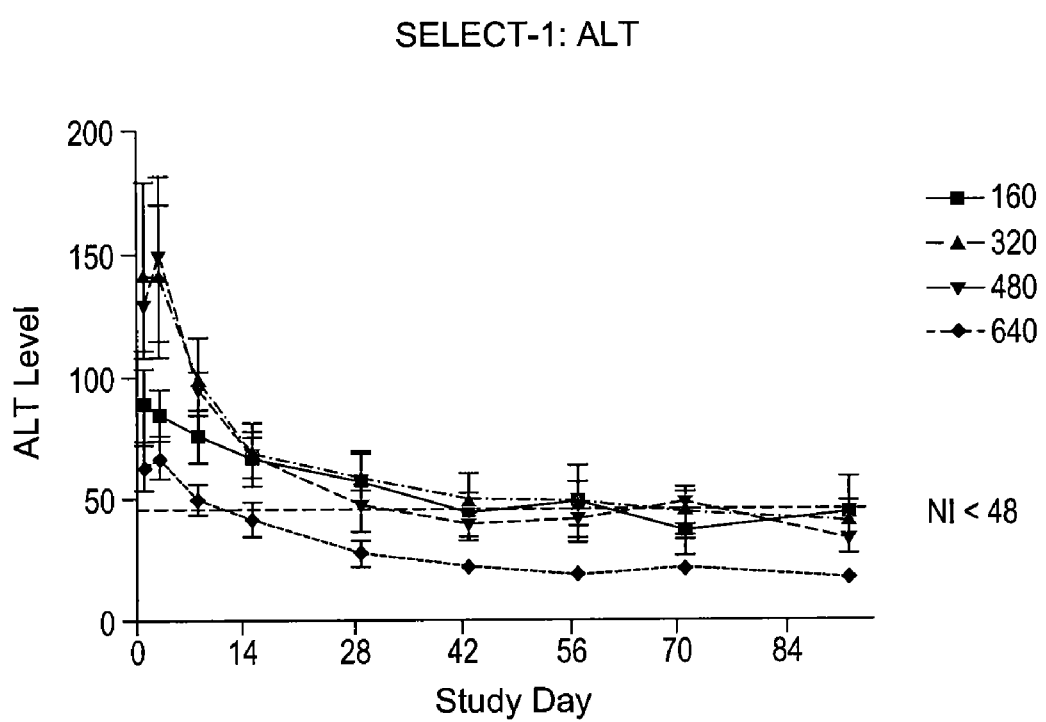

FIG. 13 shows ALT level for study groups.

Figure 14A:
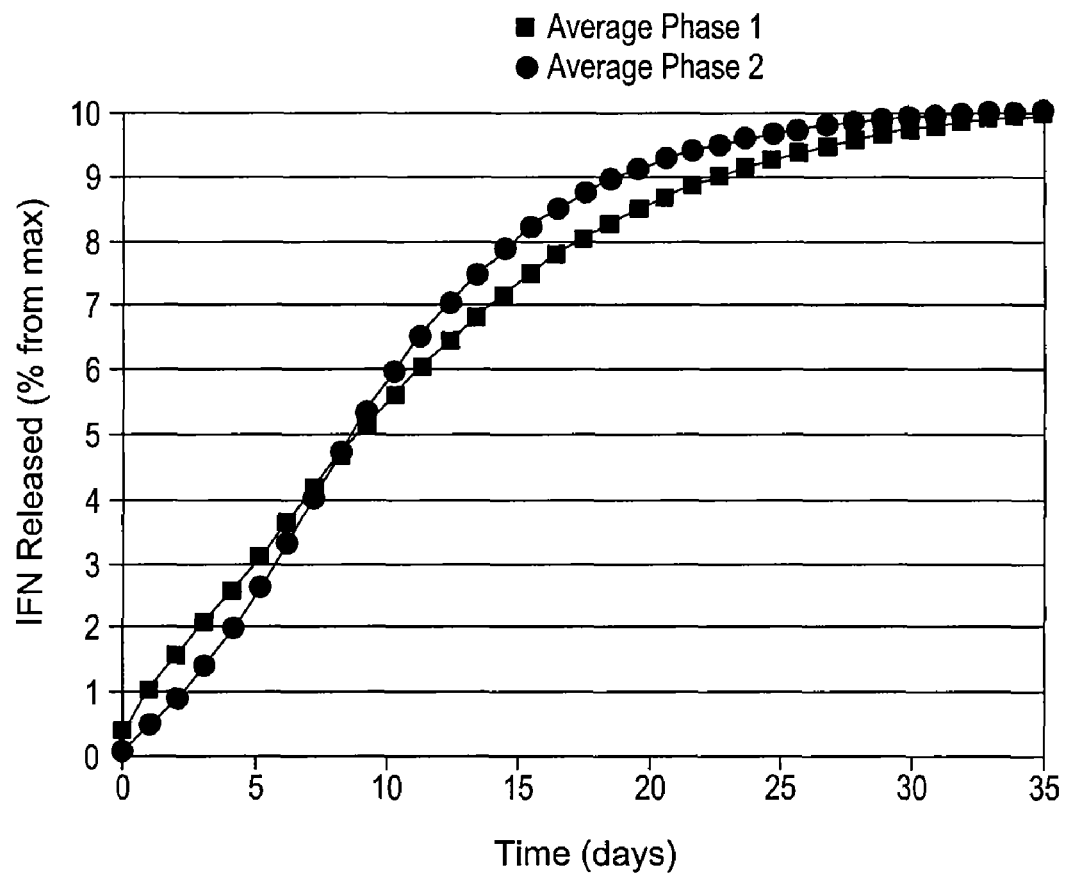
Figure 14B:
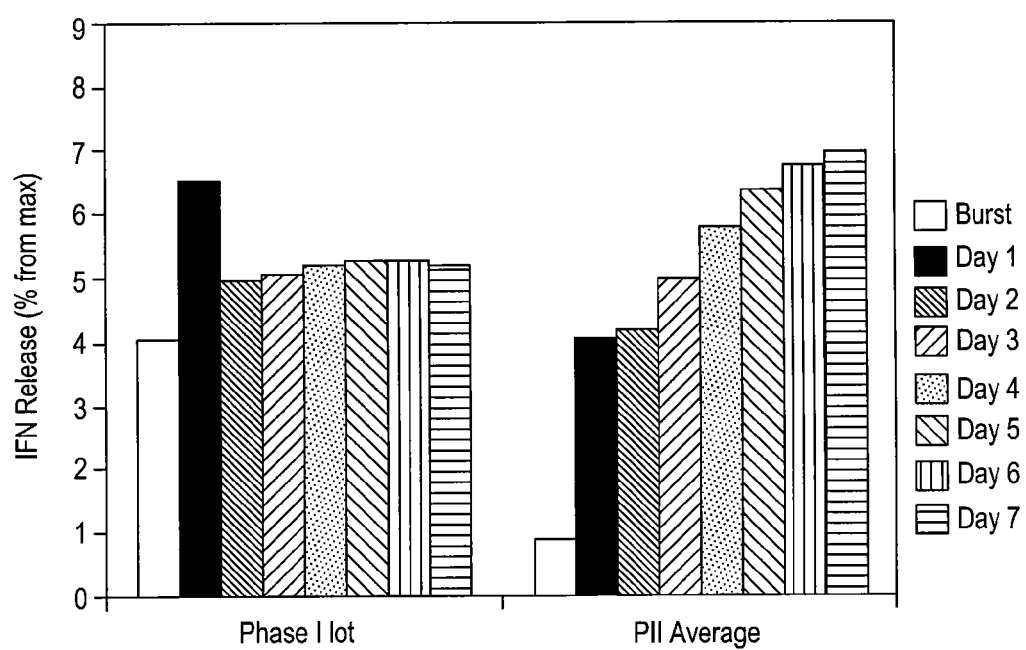

FIGS. 14A and 14B show (14A) cumulative in vitro release and (14B) daily release of Phase I vs. Phase II.

Figure 15:
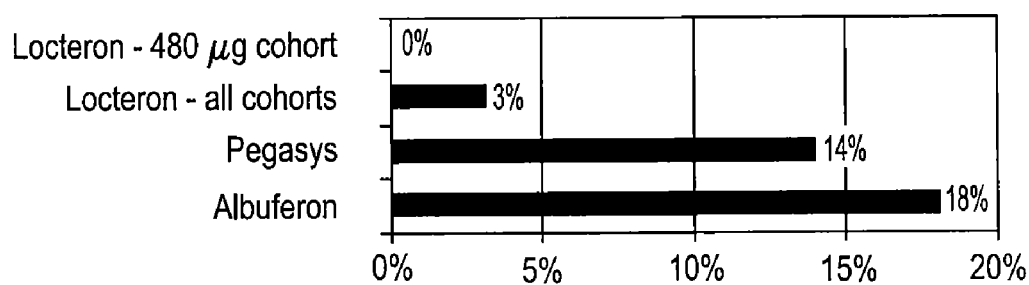

FIG. 15 shows LOCTERON Phase II Clinical Trial Adverse Events Rated as Severe and severe adverse events (from literature) associated with commercially available Pegasys and Albuferon.

Figure 16:
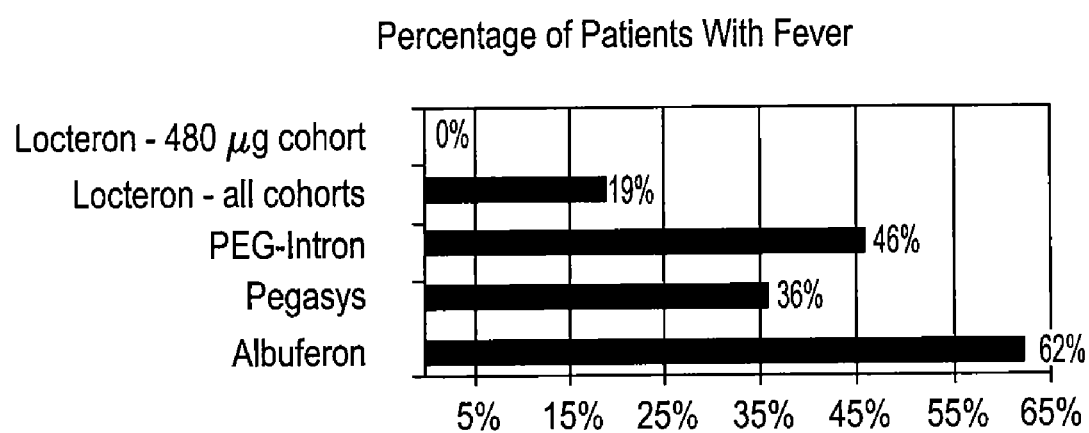

FIG. 16 shows incidence of Fever or pyrexia in Locteron Clinical Trials and in Published Results for Pegasys and Albuferon.

DETAILED DESCRIPTION

In one aspect, the controlled release interferon formulations of the present invention is administered to a human such that adverse events associated with the administration of such compounds are prevented. Without being limited by theory, it is believed that slower attainment of peak interferon serum levels in subjects using the controlled release interferon formulations described herein allow higher doses of interferon to be administered with surprisingly lower occurrence, severity, frequency, and/or duration of adverse events than without the controlled release formulations (e.g., with immediate-release interferon formulations). Such controlled release formulations thus allow a higher area under the curve of serum interferon concentration versus time to be achieved.

In one aspect, the interferon compound of the present invention is administered to a human such that adverse events associated with the administration of such compounds are prevented.

A further aspect of the invention is a method of preventing adverse events induced by or associated with the administration of such compounds. Adverse events include, but are not limited to, hemolytic anemia, musculoskeletal and connective tissue disorders, arthralgia, myalgia, disorders related administration site, asthenia, pyrexia, irritability, nervous system disorders, headache, skin and subcutaneous tissue disorders, dry skin, blood and lymphatic system disorders, neutropenia, leucopenia, metabolism and nutrition disorders, decreased appetite, neutrophil count, decreased white blood cell count, decreased red blood cell count, decreased haemoglobin, decreased gastrointestinal disorders, dry mouth, psychiatric disorders, dyssomnia, respiratory, thoracic and mediastinal disorders, cough, vascular disorders, and hyperaemia. Thus, one aspect of the present invention is a method of preventing a hemolytic anemia comprising administering the interferon compound in a formulation where the compound is released in a sigmoidal pattern.

In one embodiment, the interferon compound is formulated as a controlled release preparation such that the compound is released in a sigmoidal pattern. In one aspect, a method of treating hepatitis C virus (HCV) infection in a subject in need thereof is provided comprising administering, to a subject having an HCV infection, a first administration of a controlled release formulation of an interferon compound (e.g., interferon alpha) comprising at least 100 MIU of the interferon. The controlled release formulation may be formulated such that it releases interferon (e.g., interferon alpha) for a time period of, for example, at least one week, at least two weeks, two weeks, four weeks, etc.

In embodiments for treating subjects for HCV infection with the controlled release formulation, the subjects may be subjects having chronic or acute HCV infection and may be interferon-treatment naïve patients or interferon-treatment experienced subjects. As used herein, an "interferon-treatment naïve" subject is a subject that has never been treated with interferon for HCV infection. An "interferon-treatment experienced" subject is a subject that at least started treatment with interferon for HCV infection. "Interferon-treatment experienced" subjects include, but are not limited to, partial responders, non-responders, null responders, relapsers, and non-completers. Subjects treated for HCV infection with a controlled release interferon formulation described herein may be subjects infected with one or more genotypes of HCV (e.g., genotype 1, genotype 2, genotype 3, genotype 4, genotype 5, and/or genotype 6), and the subjects may also be co-infected with other viruses (e.g., hepatitis C virus, human immunodeficiency virus (HIV), etc.).

In another aspect, the controlled release preparations may be formulated such that the subject being treated for HCV infection experiences at least one adverse event (e.g., pyrexia) at a reduced severity and/or reduced frequency as compared to (1) a subject receiving the same dosage/amount of interferon (e.g., interferon alpha) that is not released in a sigmoidal pattern and/or (2) a subject receiving a dosage/amount of an immediate release interferon (e.g., interferon alpha, pegylated interferon alpha, or albumin-interferon alpha) required to achieve the same or similar level of efficacy as the controlled release formulation of the present invention.

In a further aspect, the controlled release formulation of the present invention may be used to administer an interferon compound to a subject over periods of time such as 20-60 weeks, 24 weeks, 48 weeks, 40-50 weeks, etc. by using multiple administrations. In certain embodiments, the controlled release formulation of the present invention may be administered at various intervals (e.g., every week, every two weeks, or every four weeks).

In certain embodiments, the controlled release formulation of the present invention may comprise at least 100 MIU of an interferon compound, at least 200 MIU of an interferon compound, from 100-1000 MIU of an interferon compound, as well as greater or lesser (e.g., 62.5 MIU of an interferon compound) amounts. Depending on the potency of the interferon, certain embodiments may comprise from 5 to 1000 MIU, from 50 to 900, from 50 to 800, from 50 to 700, from 50 to 650, from 50 to 600, from 50 to 550, from 50 to 500, from 50 to 450, from 50 to 400, from 50 to 350, from 50 to 300, from 50 to 280, from 50 to 260, from 50 to 240, from 50 to 220, from 50 to 220, from 50 to 200, from 50 to 190, from 50 to 180, from 50 to 170, from 50 to 160, from 50 to 150, from 50 to 140, from 50 to 130, from 50 to 120, from 50 to 110, about 60, about 70, about 80, about 90, or about 100 MIU. Other embodiments may comprise about 5, about 10, about 15, about 20, about 25, about 30, about 35, about 40, about 45, or about 50. For example, a method of treating hepatitis C virus (HCV) infection in a subject in need thereof is provided comprising (1) administering, to a subject having an HCV infection, a first administration of a controlled release formulation of interferon alpha comprising at least 62.5 MIU of interferon alpha; and (2) administering to the subject a second administration of the controlled release formulation comprising at least 62.5 MIU of interferon alpha, the second administration being at least two weeks after the first administration, wherein the subject experiences at least one adverse event at a reduced severity and/or reduced frequency as compared to a subject receiving the same amount of interferon alpha that is not in the controlled release formulation.

In certain aspects, the controlled release formulation of the interferon may be administered in a monotherapy or may be administered in combination therapy (e.g., dual combination, triple combination, etc.) with a therapeutically effective amount of one or more therapeutic agents. In one aspect, the present invention is a method of treating hepatitis C comprising administering a composition comprising an interferon compound and one or more therapeutic agents. Thus, in one embodiment, the one or more therapeutic agents administered with the interferon compound are one or more additional antiviral and/or immunomodulatory agents. Examples of antiviral and/or immunomodulatory agents suitable for the formulations and methods of the present invention include, but are not limited to, nucleoside antimetabolite drugs, reverse transcriptase inhibitors, viral polymerase inhibitors, viral protease inhibitors (e.g., NS2-NS3 protease inhibitors, NS3 protease inhibitors, etc), internal ribosome entry site (IRES) inhibitors, viral helicase inhibitors, viral fusion inhibitors, viral entry inhibitors, integrase inhibitors, antisense compounds, RNA interference agents, ribozymes, cytochrome P450 monooxygenase inhibitors, hematopoietins, therapeutic vaccines, monoclonal and polyclonal antibodies, nucleoside analogues, non-nucleoside inhibitors, alpha-glucosidase inhibitors, interferon enhancers, interleukins, glucocoritoids, anti-inflammatories, cyclophilin inhibitors, P7 protein inhibitors, tubulin inhibitors, TNF agonists, TLR agonists, immunosupressants, and immunomodulatory compounds. Examples of the antiviral and/or immunomodulatory agents for use in combination with the controlled release formulations of interferon described herein include, but are not limited to, ribavirin (from Schering-Plough Corporation, Madison, N.J.), Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), Telaprevir (VX-950) (from Vertex Pharmaceuticals, Cambridge, Mass.), Valopicitabine (from Idenix Pharmaceuticals, Inc. Cambridge, Mass.), Boceprevir (from Schering-Plough Corporation, Madison, N.J.), IC41 Therapeutic vaccine (from Intercell, Vienna Austria), AVI-4065 Antisense (from AVI BioPharma, Portland, Oreg.), VGX-410C IRES inhibitor (from VGX Pharmaceuticals, Inc., Blue Bell, Pa.), INN-0101 Therapeutic vaccine (from Innogenetics, Gent, Germany), R1626 Polymerase inhibitor (from Hoffmann La-Roche, Basel, Switzerland), XTL-6865 ab86-ab65 monoclonal antibody (from XTL Bio, Valley Cottage, N.Y.), HCV-796 Non-Nucleoside Polymerase inhibitor (from ViroPharma, Inc., Exton, Pa.), GS9132/ACH806 Protease inhibitor (from Gilead Sciences, Foster City, Calif.), GI 5005 Therapeutic vaccine (from GlobeImmune, Inc. Louisville, Colo.), Hemopurifier (from Aethlon Medical, Inc. San Diego, Calif.), XTL-2125 Non-Nucleoside Polymerase inhibitor (XTL Bio, Valley Cottage, N.Y.), SIRNA-034 (RNA interference) (from Sima Therapeutics (acquired by Merck & Co., Inc.), Whitehouse Station, N.J.), therapeutic vaccines from Tripep/Inovio Biomedical Corp (Huddinge, Sweden and San Diego, Calif.), RNA interference TT033 (from Benitec, Melbourne, Australia/Tacere Therapeutics, Inc. San Jose, Calif.), R7128 nucleoside polymerase inhibitor (from Hoffman-LaRoche, Nutley, N.J. and Pharmasset Inc., Princeton, N.J.), A-831 NS5A inhibitor (from Arrow Therapeutics, Ltd., London, England), Therapeutic vaccine ED-002 (from Innogenetics, Gent, Germany), NV-08 (from Idenix Pharmaceuticals, Inc. Cambridge, Mass.), Protease inhibitor ITMN0191 (from InterMune, Inc./Roche, Brisbane, Calif.), BCX-4678 (Protease Inhibitor) (from Biocryst Pharmaceuticals, Birmingham, Ala.), GL59728 and GL60667 non-nucleoside and nucleoside polymerase inhibitors (from Genelabs Technologies Inc., Redwood City, Calif.), Hepavaxx C (therapeutic vaccine) (from ViRex Medical Corp, Alberta, Canada), therapeutic vaccine (from GenPhar, Inc., Mount Pleasant, S.C.), HuMax-HepC (antibody) (from Genmab A/S, Copenhagen, Denmark), A-689 NS5a Inhibitor (from Arrow Therapeutics, Ltd., London, England), Pradefavir (from Rigel Pharmaceuticals, Inc., South San Francisco, Calif.), N-nucleoside polymerase inhibitor (from Migenix, Inc., Vacover, Canada), small molecule polymerase inhibitor (from Merck/Metabasis, Whitehouse Station, N.J.), IRES inhibitor (from PTC Therapeutics, Inc., South Plainfield, N.J.), helicase inhibitor (from Vertex Pharmaceuticals, Inc. Cambridge, Mass.), Fuzeon™ (from Trimeris, Inc. Morrisville, N.C.), protease/polymerase inhibitor (from Gilead Sciences, Foster City, Calif.), N3 3/4A protease inhibitor (from Medivir AB/Tibotec, Huddinge, Sweden), polymerase inhibitor (from Medivir/Roche, Huddinge, Sweden), protease inhibitor (from Chiron/Enanta Pharmaceuticals, Inc., Watertown, Mass.), small molecules (from Cetek Corp., Marlborough, Mass.), small molecule compounds (from Immusol, Inc., San Diego, Calif.), therapeutic vaccines (from Argos Therapeutics Inc., Durham, N.C.), polymerase and protease inhibitors (from Tibotec Pharmaceuticals Ltd. Mechlen, Belgium), RNAi compounds (from Alnylam Pharmaceuticals, Cambridge, Mass.), ISS compounds (from Dynavax Technologies Corp., Berkeley, Calif.), RNAi compounds (from CombiMatrix Corp., Mukilteo, Wash.), entry inhibitor (from Progenics Pharmaceuticals, Inc., Tarrytown, N.Y.), ACH-1095 protease inhibitor (from Gilead Sciences/Achillion Pharmaceuticals, Inc. New Haven, Conn.), nucleoside analogues (from Boehringer Ingelheim/Biota Holdings Ltd. Victoria, Australia), ANA598 Non-nucleoside polymerase inhibitor (from Anadys Pharmaceuticals, Inc., San Diego, Calif.), MX3235 Celgosivir alpha-glucosidase I inhibitor (from Migenix, Inc., Vancover, Canada), Actilon CPG-10101 TLR9 Agonist (from Coley Pharmaceuticals Group, Wellesley, Mass.), Civacir (from Nabi Biopharmaceuticals, Boca Raton, Fla.), Suvus™ (from Bioenvision, Inc., New York, N.Y.), IET Interferon Enhancing Therapy (from Transition Therapeutics, Inc., Ontario, Canada), Alinia (from Romark Laboratories L.C., Tampa, Fla.), KPE02003002 (from Kemin Pharmaceuticals, Des Moines, Iowa), ANA975 prodrug of TLR7 antagonist (from Anadys Pharmaceuticals, Inc., San Diego, Calif.), Bavituximab (from Peregrine Pharmaceuticals, Inc., Tustin, Calif.), ECH18 Immune Regulator (from Enzo Biochem, New York, N.Y.), Immu 105 (from Immunomedics, Inc., Morris Plains, N.J.), Nov-205 (from Novelos Therapeutics, Inc., Newton, Mass.), IMO-2125 (from Idera Pharmaceuticals, Cambridge, Mass.), KPE00001133 (from Kemin Pharmaceuticals, Des Moines, Iowa), AN 025-1 (from Andys Pharmaceuticals, Inc., San Diego, Calif.), JKB-122 (from Jenkin Biosciences, Inc., Research Triangle Park, N.C.), Mito-Q (from Antipodean Pharmaceuticals, Inc., San Francisco, Calif.), oral Belerofon (from Nautilus Biotech, Evry, France), Debio 025 (from Debiopharm S. A., Lausanne, Switzerland), protease inhibitor (from Axys Pharmaceuticals/Bristol-Myers Squibb, South San Francisco, Calif.), BILN2061 protease inhibitor (from Boehringer Ingelhiem, Ingelheim, Germany), Therapore immuno-therapy (from Avant Immunotherapeutics, Needham, Mass.)), Heptazyme (from Sirna Pharmaceuticals, (now owned by Merck), Whiteplain Station, N.J.)), ISIS-14803 antisense (from Isis Pharmaceuticals, Inc., Carlsbad, Calif.), VP50406 (from ViroPharma/AHP, Exton, Pa.), therapeutic vaccine (from Epimmune (now IDM Pharma, Inc.), Irvine, Calif.), protease inhibitor (from Corvas/Schering-Plough, Kenilworth, N.J.), translation inhibitor (from Ribogene, Inc., Hayward, Calif.), protease inhibitor (from Agouron Pharmaceuticals, Inc., San Diego, Calif.), Gene Regulating targets (from Signal Pharmaceuticals, LLC/DuPont, San Diego, Calif.), R803 (from Rigel Pharmaceuticals, Inc., South San Francisco, Calif.), UT231B (from United Therapeutics, Silver Spring, Md.), antisense compounds (from Idera Pharmaceuticals, Inc., Cambridge, Mass.), R1479 (from Hoffman-LaRoche, Nutley, N.J.), IMPDH inhibitor VX497 (from Vertex Pharmaceuticals, Inc., Cambridge, Mass.), and IDN-6556 (from Idun Pharmaceuticals, Inc., San Diego, Calif.). In one aspect, the controlled release formulations of interferon may be administered in combination with a therapeutically effective amount of ribavirin. In another aspect, the controlled release formulations of interferon may be administered in combination with a therapeutically effective amount of ribavirin and a therapeutically effective amount of one or more additional antiviral and/or immunomodulatory agents. In one aspect, the method of treating hepatitis C comprises administering a controlled release formulation comprising interferon-α2b wherein the interferon compound is released in a sigmoidal pattern.

Such combinations may be administered in any sequence and dose form and for the same or different lengths of time as treatment with the controlled release interferon formulation, including time periods before, during, or after treatment with the interferon formulation. For example, the various additional therapeutic agents may be administered concurrently with the interferon formulation, sequentially, or in staggered regimens (e.g., the additional therapeutic agent(s) may be administered for the same period of administration of the controlled release interferon formulation, for only a portion of the administration period of the controlled release interferon formulation, for an overlapping period, or for any period before, during, or after treatment with the controlled release interferon formulation). Thus, the additional therapeutic agent administered in such combinations may be formulated together with, or separately from, the controlled release interferon formulations of the present invention. Also, separate route of administration may be used for each additional therapeutic agent used in such combinations.

In certain embodiments, the interferon compound described with reference to controlled release preparations of the present invention may be any interferon compound known to those skilled in the art. In one embodiment, the interferon compound is that of the alpha-interferons (IFN-alfa or IFN-alpha). Examples of alpha-interferons include a number of native and modified proteins with similar molecular weight and functionality (see D. J. A. Crommelin et al., Pharmaceutical Biotechnology, Harwood Academic Publishers (1997), 219-222). In further embodiments, the alpha-interferon may be any native subtype or modified versions of IFN-alfa known to those skilled in the art, some of which are available in pharmaceutical products. For example, a mixture of several native IFN-alfa subtypes derived from pooled infected human leukocytes may be used. Members of the IFN-alfa group include the recombinant variants of IFN-alfa-2a, IFN-alfa-2b, and IFNalfacon-1.

Without being held to any particular mechanism, it is believed that the basic function of interferons is to upregulate the immune system by stimulating the immunological cells and by directly or indirectly destroying cancer cells or viruses. Among the therapeutic indications for alfa-interferons are (chronic) hepatitis B, (chronic) hepatitis C, hairy cell leukaemia, (chronic) myelogenous leukemia, multiple myeloma, follicular lymphoma, carcinoid tumor, malignant melanoma, genital warts, bladder carcinoma, cervical carcinoma, renal cell carcinoma, laryngeal papillomatosis, mycosis fungeoides, condyloma acuminata, SARS, and (AIDS-related) Kaposi's sarcoma.

The native members of the alfa-interferons have molecular masses between 19-26 kDa and consist of proteins with lengths of 156-166 and 172 amino acids. All IFN-alpha subtypes possess a common conserved sequence region 5 between amino acid positions 115-151 while the amino-terminal ends are variable. Many IFN-alpha subtypes differ in their sequences at only one or two positions. Naturally occurring variants also include proteins truncated by 10 amino acids at the carboxy-terminal end.

In certain embodiments, the controlled release formulation of the present invention comprises an interferon compound selected from the group consisting of IFN-alfa, IFN-alfa-2a, IFN-alfa-2b, IFN-alfacon-1, pegylated IFN-alfa-2a, pegylated IFN-alfa-2b, truncated IFN-alfa-2a, truncated IFN-alfa-2b, fusion proteins of IFN-alpha and albumin, and a functional derivative thereof gives very good properties. In other embodiments, the alfa-interferon may also represent a mixture of various alfa-interferon variants, such as a mixture of native or recombinant alfa-interferons which are difficult or unnecessary to separate and purify. The interferon compound may be extracted from living organisms or isolated cells or cell cultures. The cells and/or organisms from which the interferon is obtained may be modified, such as by infection, in order to produce the desired interferon. In certain embodiments, the interferon is a recombinant interferon produced from genetically engineered cells or organisms, wherein the cells or organisms are selected from mammalian, insect, bacteria, yeasts, fungi and higher plant cells or organisms. A suitable interferon for carrying out the invention is a C-terminally truncated version of IFN-alfa-2b or a mixture of more than one C-terminally truncated versions of IFN-alfa-2b. For example, molecules comprising the IFN-alfa-2b amino acid sequence in which 5 to 10 amino acids of the C-terminus have been deleted can be prepared by the currently available methods of genetic engineering. In a further embodiment, variants of IFN-alfa-2b which are truncated by 7, 8, or 9 C-terminal amino acids may be used in certain embodiments. In one embodiment, IFN-alpha-2b having 157 amino acids (i.e., truncated by 8 C-terminal amino acids as compared to the full length human IFN-alpha-2b protein) is used either alone or in combination with other interferons (e.g., in a mixture with a C-terminally truncated IFN-alpha-2b having 156 amino acids).

As used herein, the terms "interferon molecule" and "interferon" include naturally-occurring, non-naturally occurring, and recombinant interferons; biologically active fragments and variants thereof (including polypeptides having one or more amino acid additions, deletions, or substitutions as compared to a naturally-occurring interferon); interferons conjugated with other proteins or polymers (e.g., albumin or polyethylene glycol); and mixtures thereof. The terms "alpha interferon," "INF-α," "interferon-alpha," and "interferon-alfa" as used herein, include naturally-occurring, non-naturally occurring, and recombinant alpha interferons; biologically active fragments and variants thereof (including polypeptides having one or more amino acid additions, deletions, or substitutions as compared to a naturally-occurring alpha interferon); alpha interferons conjugated with other proteins or polymers (e.g., albumin or polyethylene glycol); and mixtures thereof. Thus, for example, alpha interferons include, but are not limited to, Intronn-A interferon (Schering Corporation), consensus alpha interferons, Infergen interferon alphacon-1, Belerofon interferon (Nautilus Biotech), and Maxy-alpha interferon (Maxygen).

The term "beta-interferon," as used herein, includes naturally-occurring, non-naturally occurring, and recombinant beta-interferons; biologically active fragments and variants thereof (including polypeptides having one or more amino acid additions, deletions, or substitutions as compared to a naturally-occurring beta-interferon); beta-interferons conjugated with other proteins or polymers (e.g., albumin or polyethylene glycol); and mixtures thereof. Examples of beta-interferons (IFN-beta) include IFN-beta-1a and IFN-beta-1b. These interferons are used, e.g., in the management of certain forms of multiple sclerosis, in particular relapsing forms of multiple sclerosis, to slow the accumulation of physical disability and decrease the frequency of clinical exacerbations. Patients with multiple sclerosis in whom efficacy has been demonstrated include patients who have experienced a first clinical episode and have MRI features consistent with multiple sclerosis.

In certain embodiments, the controlled release formulation of the present invention comprises a gamma-interferon (IFN-gamma). These interferons have antiviral, antiproliferative and immunomodulatory activities. An example of a gamma-interferon suitable for the controlled release formulation of the present invention is IFN-gamma-1b, which is currently marketed for the management of serious infections associated with chronic granulomatous disease.

In other embodiments, the controlled release formulation of the present invention comprises IFN-epsilon, IFN-kappa, IFN-lambda (see P. Kontsek et al., Acta Virol. 2003; 47(4): 201-15), or IFN-omega. Any interferon compound known in the art may be suitable for the controlled release formulation of the present invention.

As used herein, the terms "prevent," "preventing," and "prevention" are intended to refer to a decrease in the occurrence, severity, frequency, and/or duration of the adverse event. The prevention may be complete, e.g., the total absence of the adverse event. The prevention may also be partial, such that the severity, frequency, and/or duration of the adverse event is less than that which would have occurred without the present invention. For example, the severity, frequency, and/ or duration of the adverse event using the methods of the present invention may be at least 10%, at least 20%, at least 30%, at least 40%, at least 50%, at least 60%, at least 70%, at least 80%, at least 90%, or at least 100% less than the severity, frequency, and/or duration of the adverse event that would have occurred without the present invention.

As used herein, the degree of severity of adverse events that actually occur in subjects is discussed in terms of "mild", "moderate", "severe", and "serious". A "mild" adverse event means that the adverse event was noticeable by the subject, but that the adverse event was easily tolerated and had no impact on daily activities of the subject. A "moderate" adverse event means that the adverse event caused sufficient discomfort to interfere with the subject's daily activities, but that daily activities of the subject could still be performed and were not disrupted. A "severe" adverse event means that the adverse event is incapacitating and prevented the subject from performing some of their daily activities. A "serious" adverse event is one that results in death, a life-threatening situation, or a need for hospitalization.

As used herein, the term "adverse events induced by or associated with" an interferon compound refer to any adverse event that a patient develops during, or at the end of treatment with an interferon compound. The term is also intended to include any adverse event that a patient develops during, or at the end of treatment with an interferon compound in combination with another therapeutic agent (e.g., an-antiviral drug such as ribavirin). Thus, the term is intended to include all adverse events a patient suffers during or just after the end of the administration of an interferon compound alone or in combination with another therapeutic agent (e.g., an antiviral and/or immunomodulatory agent e.g., ribavirin) regardless of whether a direct or indirect causal link between the interferon compound and the adverse event can be demonstrated. In one embodiment, adverse events developed within five weeks after the end of administration of an interferon compound are included in "adverse events induced by or associated with" the interferon compound.

The terms "sigmoidal", and "sigmoid" as used herein refer to an in vitro release pattern that is more or less an s-shaped curve (i.e., the release pattern that is generally curved in two directions like the letter S). That is, a "sigmoidal" release pattern involves an initial lag time during which no drug, or very little drug is released, followed by a phase where the rate of drug release increases, followed by a phase where the rate of drug release decreases toward zero.

The term "microparticle" as used herein means a polymeric particle which contains an active agent (e.g., in solution or solid form). The term "microparticles" includes "microspheres" and "microcapsules". A "microsphere refers to a type of formulation in which the active drug molecule (or pockets of drug molecules) are dispersed in the polymeric matrix. A "microcapsule refers to a formulation in which a drug core is surrounded by a polymeric layer or shell.

As used herein, the terms "microencapsulate," microencapsulation," "encapsulate" and "encapsulation" refer to a process in which a small (e.g., microscopic) droplet comprising one or more drug compounds is incorporated into a particle (e.g., microparticle or microsphere). Thus, the terms are intended to include situations where a solution of the drug compound or the drug compound itself is surrounded by the biodegradable polymer. The terms also include situations where the one or more drug compounds are distributed uniformly in the biodegradable polymer which is essentially inert and serves to isolate, protect or retard the release of the drug compound. The drug compound may be released from the polymeric matrix through either diffusion or permeation of the drug compound through the polymer matrix or through erosion or rupture of the matrix. Variation in the size, choice of the biodegradable polymer and the method by which the microparticles are prepared determine the rate and the release pattern of the drug compound.

The controlled release formulation of the invention may be formulated so as to be suitable for a variety of modes of administration, such as topical, oral, rectal, vaginal, or parenteral administration. It is to be understood that parenteral administration is intended to include any invasive route of administration, such as subdermal, intradermal, subcutaneous, intramuscular, locoregional, intratumoral, intraperitoneal, interstitial, intralesional, intravenous, and intraarterial. In one embodiment, the route of administration of the controlled release formulation is subcutaneous, intramuscular injection or implantation.

The controlled release formulation of the present invention suitable for parenteral administration may comprise excipients that are safe and tolerable for parenteral administration. In one aspect, the controlled release formulation is formulated to have an osmolality in a range from about 150 to 500 mθsmol/kg or from about 250 to 400 mθsmol/kg. In certain embodiments, the pH of the controlled release formulation of the present invention may be approximately in the physiological range. In certain embodiments, the pH of the controlled release formulation of the present invention is about 4 to 8.5, about 5.0 to 8.0, or about 5.5 to about 7.5.

It should be understood that the microparticles may be solid or semisolid particles having a diameter in the region of about 0.1 to about 500 µm, regardless of their shape or internal structure, and includes microspheres and microcapsules. In one embodiment, the microparticles may have a diameter from about 1 to about 300 µm, about 10 to about 250 µm, about 50 to about 200 µm, or about 75 to about 150 µm. The microparticles may have a volume-average diameter of about 10 to about 400 µm, about 10 to about 250 µm, about 50 to about 200 µm, or about 75 to about 150 µm as measured by photon correlation spectroscopy. In some embodiments, the average diameter is in the range from about 50 to about 150 µm.

The controlled release formulation of the present invention comprising an interferon compound and one or more therapeutic agents may be prepared by encapsulating one or more of the drugs in a microparticle comprising a biodegradable polymer. The biodegradable polymers suitable for the present invention may be resorbable or bioerodable biocompatible polymers including both natural and synthetic polymers. Natural polymers are typically absorbed by enzymatic degradation in the body, while synthetic resorbable or bioerodable polymers typically degrade by a hydrolytic mechanism and by enzymatic degradation. In certain embodiments, the biodegradable polymer is a block copolymer comprising one or more poly(ethylene glycol terephthalate) segments and or more poly(butylene terephthalate) segments. The particle size of the microparticles may be 20-500 µm. In certain embodiments, the particle size is 20-140 µm. In other embodiments, the particle size is about 30 to about 120 µm, or about 50 to about 100 µm.

In one embodiment, the biodegradable polymer may be a homopolymer or a copolymer (including block copolymer) comprising poly(ethylene glycol terephthalate), poly(butylene terephthalate), ethylenevinylacetate, polyglactin, polyglactic acid, polyaldonic acid, polyalkanoates, poly(L-lactide) (PLLA), poly(D,L-lactide) (PDLLA), polyglycolide (PGA), poly(caprolactone), and/or poly(1,3-trimethylene carbonate). Other biocompatible, biodegradable polymers may include, for example, poly(lactide-co-glycolide)s, poly (glycolic acid)s, poly(lactic acid-co-glycolic acid)s, polycarbonates, polyesteramides, polyanhydrides, poly(amino acid)s, poly(ortho ester)s, polyacetals, polycyanoacrylates, polyamides, polyacetals, poly(ether ester)s, copolymers of poly(ethylene glycol) and poly(ortho ester)s, poly(dioxanone)s, copolymers of polyethylene glycol and polyorthoester, poly(alkylene alkylate)s, biodegradable polyurethanes, poly-D,L-lactic acid, poly-L-lactic acid, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and blends or copolymers thereof.

The choice of a particular polymer or copolymer is not important so long as a sigmoidal release profile is maintained and none of the degradation by products is either toxic to the subject or interferes with the release of any of the active ingredients.

In certain embodiments, the one or more therapeutic agent may be formulated separately. In one embodiment, The one or more therapeutic agent is formulated in a pharmaceutical composition wherein comprising additional components or ingredients that are themselves pharmaceutically acceptable, e.g., where oral administration is foreseen, acceptable for oral use; where topical administration is foreseen, topically acceptable; and where intravenous administration is foreseen, intravenously acceptable. For example, when the one or more therapeutic agent is an antiviral agent such as ribavirin, such agent may be formulated as an oral pharmaceutical composition. Where the one or more therapeutic agent is suitable for intravenous administration, such agent may be formulated as a pharmaceutical composition suitable for intravenous administration.

In one embodiment, each of the one or more interferon compounds and the one or more therapeutic agents is microencapsulated separately. In this embodiment, a controlled release formulation comprising an interferon compound encapsulated in a block copolymer comprising one or more poly(ethylene glycol terephthalate) segments and or more poly(butylene terephthalate) segments is prepared. Separately, a controlled release formulation comprising one or more therapeutic agents encapsulated in a block copolymer comprising one or more poly(ethylene glycol terephthalate) segments and or more poly(butylene terephthalate) segments is prepared. Suitable proportions of the two separately pre-prepared microencapsulated drugs (one containing an interferon compound and one containing one or more therapeutic agents) are either mixed or separately administered to a subject.

Alternatively, both the one or more interferon compounds and the one or more therapeutic agents may be encapsulated together. In this embodiment, aqueous solutions of the one or more interferon compound and of the one or more therapeutic agents may first be pre-mixed together before the water-in-oil-in-water emulsion is prepared (see experimental section for detail). In certain embodiments, two aqueous solutions, one comprising one or more interferon compounds and one comprising one or more therapeutic agents, may simultaneously or sequentially be added to the stirred solution containing the microencapsulation polymer (a block copolymer comprising one or more poly(ethylene glycol terephthalate) segments and or more poly(butylene terephthalate) segments). In either embodiment, the proportion of the one or more interferon compounds and the one or more therapeutic agents may be controlled by choosing appropriate amounts of aqueous solutions containing known amounts of respective active agents.

If more than one interferon compound is to be encapsulated in the controlled release microparticle dosage of the present invention, the interferon compounds may either be pre-mixed in an aqueous solution prior to microencapsulation or two or more solutions each containing an interferon compound may simultaneously or sequentially be added into a stirred solution of the microencapsulation polymer. Similarly, if more than one other therapeutic agent are to be encapsulated in the controlled release microparticle dosage of the present invention, the one or more therapeutic agents may either be pre-mixed in an aqueous solution prior to microencapsulation or two or more solutions each containing a therapeutic agent may simultaneously or sequentially be added into a stirred solution of the microencapsulation polymer. As can be seen, a person skilled in the art can design any desired combination of an interferon compound and one or more therapeutic agents and prepare controlled release microparticle dosage of the present invention.

As described herein, the controlled release interferon formulations have improved tolerability (i.e., patients experience one or more adverse events at a reduced severity and/or reduced frequency) and may have reduced toxicity as compared to (1) the same dosage/amount of interferon (e.g., interferon alpha) that is not in the controlled release formulation and/or (2) a dosage/amount of an interferon that is not in the controlled release formulation (e.g., interferon alpha, pegylated interferon alpha, or albumin-interferon alpha) required to achieve the same or similar level of efficacy as the controlled release formulation. The controlled release interferon formulations may improve the tolerability/reduce the toxicity of treatments involving monotherapy with the interferon formulations as well as combination therapy with the interferon formulations (i.e., in combination with ribavirin and/or one or more therapeutic agents such as antiviral and/or immunomodulatory agents). Additionally, the controlled release interferon formulations described herein may reduce drug-drug interactions of interferon (e.g., interferon alpha) with one or more other therapeutic agents such as, for example, one or more other antiviral and/or immunomodulatory agents (e.g., ribavirin) as compared to the drug-drug interactions occurring when combination therapy is conducted using (1) the same dosage/amount of interferon (e.g., interferon alpha) that is not in the controlled release formulation and/or (2) a dosage/amount of an interferon that is not in the controlled release formulation (e.g., interferon alpha, pegylated interferon alpha, or albumin-interferon alpha) required to achieve the same or similar level of efficacy as the controlled release formulation. Thus, the controlled release interferon formulations described herein may reduce the overall side effects and/or toxicity in patients receiving combination therapy involving one or more antiviral and/or immunomodulatory agents in addition to the controlled release interferon. As also described herein, such controlled release interferon formulations may be administered in mono- or combination therapy to reduce the occurrence of interferon nadirs in such therapies, which may improve the likelihood of SVR in patients receiving the therapies.

The controlled release formulations may also be "Sustained Release" formulations. The concept of "Sustained Release" as used herein refers to administration systems which do not provide immediate release of interferon, but which are capable of releasing a controlled amount of interferon over a period of time (the "Administration Interval"). The Administration Interval preferably is more than one week, e.g. 2-4 weeks, and most preferably it is 2 weeks, 4 weeks, or 1 month. The Administration Interval typically corresponds with the period of time between two sequential single administrations in a method of treatment or between the last administration and the time point designated as the end of treatment for the method.

In one aspect, an interferon, preferably an alpha-interferon, drug product is provided for use in the treatment of hepatitis C virus (HCV) infection, wherein the product is a Sustained Release preparation of interferon which, upon a single administration, releases interferon during an Administration Interval of at least one week, preferably two weeks, wherein the release follows a pattern comprising an Early Release, preferably during days 1-3 after administration, below Plateau Daily Release, preferably below Theoretical Daily Release, and most preferably below Average Daily Release.

"Theoretical Daily Release" indicates the amount of drug incorporated into a single dosage, divided by the number of days of the Administration Interval.

"Plateau Daily Release" indicates the daily release associated with a period of more or less constant highest release rate exhibited during the part of the Administration Interval between the period of Early Release, and before (if applicable) a period of declined release during a terminal portion of the Administration Interval.

The "Average Daily Release" indicates the total amount of drug released during the Administration Interval, divided by the number of days of the Administration Interval. If all of the drug administered is released within the Administration Interval, the Average Daily Release will be equal to the Theoretical Daily Release. If not all of the drug administered is released within the Administration Interval, the Average Daily Release will be lower than the Theoretical Daily Release. In the latter case, the quantity of drug not released within the Administration Interval is referred to as a "Remaining Load."

The Sustained Release preparation may have a release pattern that is sigmoidal. Sustained Release preparations of interferon may have a sigmoidal pattern over an Administration Interval between a first and a second administration, wherein the system provides for a Remaining Load of interferon at the end of the Administration Interval.

The preparation is not limited to any specific system for the Sustained Release of INF, as long as it satisfies the criteria which are believed to be responsible for the results obtained with respect to RVR, EVR, and adverse effects/side effects (AE). In theory, the required Sustained Release can be attained by delivery systems which might not be properly characterized as Sustained Release, e.g. systems which provide immediate release of the total dosage amount of INF and which provide prolonged action by prolonged clearance of INF, as long as the system leads to circulating INF.

Preferably, the system used is based on microparticle technology as described in WO 2006/085747; this disclosure is referred to rather than repeated here, and the entire content thereof is incorporated herein by reference.

Most preferably, the system employed provides for a more or less constant release, over the period of the Administration Interval after the below-discussed Early Release. The system may provide for a more or less constant release over the entire Administration Interval, i.e. between two sequential administrations, and it is also possible to use a system which, after Early Release, provides for a period of Stationary Release at more or less constant level, after which at the end of the Administration Interval, e.g. during the last 4 days of a 2-week interval, a slight decline occurs.

The concept of "Early Release" relates to the first 1-4 days, and preferably the first 3 days, after administration. It has now been found, that—besides the ongoing preference to avoid burst release—a relatively low Early Release seems to positively affect the occurrence of adverse events such as fever.

Release can be determined in various ways known in the art, and for generally used interferons, appropriate in vitro release determinations exist. An example of determination of in vitro release is illustrated in the Examples below.

As is further preferred, the system may provide for a "Remaining Load". This refers to systems still capable of releasing interferon at the end of the Administration Interval. The Remaining Load can be provided for by selecting the duration of the Administration Interval such as to be shorter than the period of time during which all of the interferon is released. The Remaining Load may also be provided for by formulating the Sustained Release preparations in such a way as to avoid that all of the drug releasable therefrom will in fact be released over the period of time of the Administration Interval.

The Remaining Load enables treating HCV infection in such a way as to administer to a patient in need thereof a first dose of the interferon product, and later in time administering a second dose of the interferon product, wherein the second dose is administered at a moment in time before the interferon serum level resulting from the first dose reaches its nadir, wherein the interferon product is a Sustained Release preparation of interferon, and the second dose is administered on a day on which the first dose still releases interferon. It is believed that reducing the occurrence of interferon nadirs may improve the likelihood of SVR, which a sizeable percentage of patients fail to achieve under current interferon therapy regimens. Such treatment may also be preceded by one or more administrations of a controlled release formulation of interferon that does not result in a Remaining Load (i.e., a formulation that releases all of the interferon in the formulation by the end of the Administration Interval and possibly at some time point before the end of the Administration Interval).

At the point in time of a second (or further) administration, the Remaining Load of the first (or previous) administration will serve to complement the Early Release of said second or further administration, so as to reach a desired level of combined release. The Early Release of the second (or further) administration, in combination with the Remaining Load of the first (or previous) administration as described, serves to provide a more constant release over a multitude of repeated administrations. In addition to providing a more constant release pattern over multiple administrations, such formulations may provide a benefit in obtaining more constant levels (as determined in serum or tissue, as applicable) of the interferon administered. Particularly, the difference between peak and trough levels for the tissue or blood compartment interferon concentration may be substantially decreased (and potentially eliminated) as a result of multiple administrations using systems with a Remaining Load. As stated above, the multiple administrations may include one or more initial administrations of a controlled release formulation of interferon that does not result in a Remaining Load (i.e., a formulation that releases all of the interferon in the formulation by the end of the Administration Interval and possibly at some time point before the end of the Administration Interval).

Preferably, the Remaining Load (RL) is given by a percentage of at most 30% of the interferon load still present at the end of the Administration Interval (i.e. when a next administration is given) and, more preferably a percentage of from 10 to 20%. In such preferred systems, the Average Daily Release can be defined as follows in the case of a dosage strength of X µg, and an Administration Interval of 14 days: $(X-\% RL)/14$. E.g. if the dose is 200 µg, and the Remaining Load is 15%, the Average Daily Release is 85% of 200 µg released over 14 days, which amounts to about 12 µg (12.1 µg) per day of interferon. Analogous calculations can be made for different dosages, different percentages of Remaining Load, and different Administration Intervals.

The dosage amounts of interferon are preferably about 100 μg to 800 μg per 2-weeks administration, typically about 200 μg to 600 μg (preferably about 300 μg to 500 μg), but also e.g. about 500 μg to 700 μg. Expressed in MIU, this means about 30 MIU to about 240 MIU, typically about 60 MIU to about 200 MIU. Expressed in weekly dosage this refers to about 50-400 μg, typically about 100-300 μg.

With a preferred Administration Interval of 14 days, the various daily release values for a few exemplified dosages within the preferred range are as follows.

| Dosage in μg | Theoretical Daily Release in μg | Average Daily Release in μg if Remaining Load is 20% | Average Daily Release in μg if Remaining Load is 10% |
|---|---|---|---|
| 100 | 7.1 | 5.7 | 6.4 |
| 200 | 14.3 | 11.4 | 12.9 |
| 320 | 22.9 | 18.3 | 20.6 |
| 400 | 28.6 | 22.9 | 25.7 |
| 480 | 34.3 | 27.4 | 30.9 |
| 600 | 42.9 | 34.3 | 38.6 |
| 640 | 45.7 | 36.6 | 41.1 |

The controlled release formulations and Sustained Release systems described herein may lead to favourable effects on RVR and EVR, as well as on AE.

As to the latter, an improved benefit to risk ratio can be obtained, in terms of high end HCV response in combination with low end AE frequency and severity. It is remarkable that this improved benefit to risk ratio results in a regimen of administration involving repeated dosing.

The compositions described herein may be put to use for a duration of the administration commensurate with current interferon therapy, viz. 24 or 48 weeks.

The invention is illustrated with reference to the following, non-limiting Examples.

Example 1

In-Vitro Release (IVR) Profile of Locteron™

To monitor the amount of IFNα-2b (BLX 883) that is released in vitro from LOCTERON, freeze dried LOCTERON drug product is reconstituted with 2 mL of 0.01% Tween-80 and 0.01% sodium azide in PBS (phosphate buffer saline) for the determination of the in vitro release profile. The Locteron™ microspheres containing IFNα-2b are immersed in eppendorf tubes containing 2 mL PBS reconstitution solution and incubated at 37° C. under constant agitation (75 rpm). The release of IFNα-2b is periodically monitored by extracting 1.7 mL aliquots after 6 hrs, 1 day, 4, 7 or 9, 11, 14 and 17 days. The eppendorf tube is replenished with 1.7 mL of reconstitution solution. The concentration of IFNα2b is monitored using HP-SEC analysis as described below. All in-vitro release studies have been conducted in multi fold (independently prepared) and mean values and standard deviations have been calculated.

Protein Concentration by HP-SEC

The protein level in the different in-vitro release (IVR) samples is determined by High Performance Size Exclusion Chromatography (HP-SEC). With a reference standard a calibration curve is prepared, with which the concentrations in the release samples can be calculated.

20 μl of sample is applied to a Tosoh Bioscience TSK-GEL G2000 SWXL (7.8 mm ID×300 mm, 125 Angstrom, 5 μm) column. IFN is eluted isocratically in 0.01% Tween-80 in PBS with 0.01% sodium azide, pH 7.4 at a flow rate of 0.8 mL/min at room temperature. Protein is detected with a fluorescence detector at 280 nm excitation and 333 nm emission.

Calculation of In-Vitro Release (IVR) Profiles

The IFN concentrations of the samples at different timepoints are filled in, in a validated excel sheet. In this sheet the cumulative release is calculated based on the protein concentrations found in the different release samples. The protein concentrations are corrected for the amount of buffer that is refreshed at each timepoint. When the release has ended the total amount released per LOCTERON vial, speed of release and release duration can be calculated.

Example 2

Preparation of Sustained Release Dosage Form

Biolex's IFNα-2b (BLX-883)

Biolex's IFNα-2b is produced by Biolex Inc., Pittsboro, N.C., USA, using a transgenic *Lemna minor* plant line, transformed using *Agrobacterium* transfected with a plasmid containing a codon optimized interferon alpha 2b gene.

BLX-883 is an aglycosylated product mixture with 2 major components. The predominant species consists of a C-terminally truncated version of IFNα-2b having 158 amino acids. The minor species consists of a C-terminally truncated version of IFNα-2b having 157 amino acids. Native human IFNα-2b is a 165 amino acid protein with O-glycosylation.

PolyActive™ 1500PEGT77PBT23

PolyActive™ is a copolymer of poly(ethylene glycol)-terephthalate (PEGT) and poly(butylene terephthalate) (PBT). Polyactive™ is available in a broad range of the weight ratios of the two blocks (PEGT and PBT), and molecular weights of polyethylene glycol (PEG) ranging from 300-4000 g/mole. The specific PolyActive™ composition in the Example contains PEG segments of 1500 g/mol, 77 wt % PEGT, and 23 wt % PBT (1500PEGT77PBT23). The polymer is formed into microspheres.

The encapsulation of IFNα-2b (BLX-833) in the microspheres occurs in situ, when the microspheres are formed. In short, an aqueous solution of IFNα-2b is emulsified in a dichloromethane (DCM) solution of PolyActive™ 1500PEGT77PBT23. The emulsion is then dispersed in an aqueous solution of polyvinyl alcohol in PBS, to form a water-in-oil-in-water (W/O/W) emulsion. The dichloromethane is subsequently evaporated, thus encapsulating the drug. Finally, the microspheres are filtered, washed with a mannitol solution (to wash out PBS and PVA), collected by filtration and lyophilized with mannitol as bulking agent.

Once the drug substance (IFNα-2b (BLX 883)) is encapsulated into the PolyActive™ microspheres, the key physicochemical characteristics that can influence the performance of the Locteron™ drug product are the pH and temperature.

Thus, two products were made. Products (A) and (B) which differ in release characteristics as follows (expressed as percentages of dose incorporated into the microspheres):

| Point in time | Product (A) | Product (B) |
|---|---|---|
| T = 0 (by extrapolation) | 2-6% | 0-3% |
| 1 day | 11% | 1-6% |
| 2 days (interpolation) | 16% | 7-11% |

-continued

| Point in time | Product (A) | Product (B) |
|---|---|---|
| 3 days (interpolation) | 20% | 9-15% |
| 4 days (interpolation) | 27% | 16-25% |
| 7 days | 42% | 35-45% |

Product (B)

Product (B) in the Examples herein was prepared as follows:

The encapsulation of IFNα2b (BLX-833) in the microspheres occurs in situ, when the microspheres are formed.

An amount equivalent to 120 mg of an aqueous solution of 20 mg/ml IFNα2b in phosphate buffered saline (PBS) buffer is emulsified in a solution of 6 g PolyActive 1500PEGT77PBT23 in 55 g dichloromethane with a high shear mixer (Ultraturrax).

The emulsion formed is then dispersed in 500 g of an aqueous solution of 4 weight % polyvinyl alcohol (PVA) solution in phosphate buffered saline to form a water-in-oil-in-water (W/O/W) emulsion. For the formation of the microspheres, the emulsion is poured into a 1250 RPM stirred PVA solution, thus encapsulating the protein.

A sigmoidal release pattern may be achieved by delaying the release rate of the interferon, e.g., by using larger particles or a more dense polymer network. For example, a sigmoidal release pattern may be achieved by changing the solvent removal rate. The slower the solvent removal rate, the more the release pattern shifts to a sigmoidal release pattern.

The dichloromethane is subsequently removed through the outer phase of the secondary emulsion, and hardening of the microspheres takes place. To further induce hardening of the microspheres, an additional 500 g PBS is pumped into the vessel after transferring the emulsion to that vessel and the stirring speed is decreased to 500 rpm. In addition, nitrogen gas is blown over the water-air interface for approximately 5 hours (30 L/min). Subsequently, the nitrogen flow is reduced to 7 L/min for another 17 hours.

After hardening, large particles and agglomerates are removed by pumping the microsphere solution through a 180 μm Mesh filter screen. The microspheres are collected using a dead end filter (20 μm) and washed with a mannitol solution of 35 g/L. This step is repeated, in total, 5 times. Between the steps, the microspheres are released from the filter. At the end the microspheres are collected in a 500 mL filling vessel.

Finally the microsphere suspension is filled in vials and transferred to a freeze dryer. Lyophilization of the microsphere product is followed by complete closing and capping of the vials.

Example 3

Phase I, Dose Escalation Study; Product Used: (A)

This phase I clinical trial was a randomized, double-blind, active- and placebo-controlled, dose-escalation study evaluating a single subcutaneous dose of LOCTERON. Subjects eligible for study entry were healthy male volunteers 21-50 y of age with a body mass index of 20-28 kg·m-2.

Study subjects were admitted to the study center on the afternoon before treatment, at which time the following baseline assessments were performed: vital signs and body temperature; physical examination; electrocardiogram (ECG); biochemistry and hematology; urinalysis; drug and alcohol screening and serology; serum free or pegylated IFN-α2b; biomarkers; and immunogenicity. At 0800-1000 h the following day the subjects received by subcutaneous injection: 20, 80 or 320 μg LOCTERON, 80 μg pegylated IFN-α2b (PEG-Intron®, Schering Corp., Kenilworth, N.J.), 2, 8 or 32 mg PolyActive™ microspheres not containing IFN-α2b, or 10% hydroxyethyl starch placebo (Hemohes®, B. Braun, Melsungen, Germany). LOCTERON is composed of PolyActive™ microspheres containing 1% (w/w) IFN-α2b, and LOCTERON doses are expressed in terms of IFN-α2b content rather than microsphere mass. Thus, the 2, 8 and 32 mg doses of control PolyActive microspheres provided the same microsphere quantities as the corresponding 20, 80 and 320 μg LOCTERON doses.

The 20 μg LOCTERON and 2 mg PolyActive™ microsphere doses were administered in 0.2 mL volumes per injection site, while the higher doses were injected in 0.4 mL per site. The 320 μg LOCTERON and 32 mg PolyActive™ microsphere doses were divided between 4 injections sites, whereas lower doses were injected at a single site.

Results:

The study having been conducted in healthy volunteers, results are limited to safety and tolerability, and pharmacokinetics and pharmacodynamics, with biomarker effects in these healthy male volunteers also tested. The product is well tolerated in the dose range of 20-320 μg. It has an AE profile similar to PEG-Intron®, and the intensity of AEs of the product (320 μg) is similar to or less than PEG-Intron®.

As to influenza-like illness (with fever being one of the symptoms monitored therein), PEG-Intron® (80 μg, i.e. 5 MIU) exhibited a 100% score of 6 out of 6 subjects meeting the criteria for this AE. No subjects (0/4) receiving Product A exhibited influenza-like illness at doses 6.25 MIU (20 μg) and 25 MIU (80 μg), while 75% (3 out of 4) subjects receiving Product A at 100 MIU (320 μg) exhibited influenza-like illness.

Example 4

Phase II Clinical Trial; Product Used: (B)

This Phase II, multicentre, single country, European, open-label, randomised study with four treatment arms in subjects with chronic HCV infection was conducted using Product B described above, referred to in this Example as Locteron.

The primary efficacy endpoint in the study was the log decrease in HCV RNA at 4 weeks compared to baseline. Secondary efficacy endpoints were the proportion of subjects in each arm of the study showing a 2 log or greater drop in HCV RNA after 12 weeks of treatment compared to baseline, the proportion of subjects with HCV RNA eradication (levels below LLQ 28 IU/mL; Roche Taqman) after 12 weeks of treatment, log decrease of HCV RNA levels, profiles of serum levels of neopterin, 2',5'-OAS and exposure to IFNα2b (as measured by ELISA).

Abstract of Study

One approach of potentially increasing SVR rates and improving treatment convenience and tolerability is through controlled release of unmodified IFN-α. Some potential advantages are preserving the full activity of the IFN-α molecule, maintaining therapeutic IFN-α levels in circulation longer, avoiding concentration nadirs that may limit effectiveness as well as spikes that may reduce tolerability, and permitting less frequent dosing schedules.

Locteron® is a controlled release formulation containing 2% (w/w) unmodified recombinant IFN-α2b (Biolex Therapeutics, Pittsboro, N.C., USA) in poly(ether-ester) microspheres (PolyActive™, OctoPlus N.V., Leiden, The Netherlands). The biodegradable and biocompatible microspheres continuously release free unpegylated IFN-α2b over a period of 2 weeks. The recombinant IFN-α2b component of Locteron is synthesized without glycosylation in a Lemna aquatic plant expression system and, due to post-translational cleavage, consists of a mixture of molecules with either 7 or 8 amino acids removed from the C terminus. The antiviral and antiproliferative activities of the Lemna-derived IFN-α2b in vitro are indistinguishable from those of standard *E. coli*-derived IFN-α2b.

The Locteron controlled release formulation of free (unpegylated) recombinant IFN-α2b in poly(ether-ester) microspheres (Locteron) was injected at doses of 160, 320, 480 or 640 μg every 2 weeks for 12 weeks with concomitant weight-based ribavirin in 32 treatment-naïve patients with chronic HCV genotype 1. Treatment was well-tolerated, with 31 patients (97%) successfully completing the study. Full Locteron doses were administered on 96% of scheduled treatment occasions. Episodes of flu-like symptoms were generally mild, brief and early in the treatment course. The antiviral activity of the highest three Locteron doses was similar, while the 160 μg dose was less potent. In the 320, 480 and 640 μg dose groups, 62-75% of patients achieved a ≧2 log10 HCV RNA reduction by 4 weeks and 88-100% by 12 weeks. For those three dose groups the pooled median time to ≧2 log10 reduction was 11 days (95% confidence interval, 7-35 days). In those groups viral eradication was accomplished in 25% of patients by 4 weeks and in 62% by 12 weeks. After Locteron injection, stable plateau levels of serum IFN-α2b were generally reached within 72 h. Mean trough IFN-α2b concentrations exceeded 5 pg·mL-1 in the 160 and 320 μg dose groups and 10 and 15 pg·mL-1 in the 480 and 640 μg groups, respectively. Linear dose responses were observed between Locteron and the pharmacodynamic markers neopterin and 2',5'-oligoadenylate synthetase.

Detailed Report of Phase II Clinical Trial

Study Patients

A total of 54 patients were screened at 3 centres in one country, i.e. Ukraine. Of these, 22 patients were not randomised as they either did not meet the criteria, in various instances because of normal alanine aminotransferase (ALT) at screening, or met the criteria for exclusion. Therefore, a total of 32 patients were included in the Safety Population and randomised into one of four treatment groups. The disposition of patients is summarised in Table 1.

Dose Reductions

A small number of dose reductions were observed during the study. Table 3 below displays the actual doses of Locteron™ administered during the study, by individual patient.

TABLE 3

LOCTERON ™ doses administered by individual patient (Safety Population; N = 32)

| Patient | Dose | Day 1 1st dosing | Day 15 2nd dosing | Day 29 3rd dosing | Day 43 4th dosing | Day 57 5th dosing | Day 71 6th dosing |
|---|---|---|---|---|---|---|---|
| 01/10 | 160 μg | 160 | 160 | 160 | 160 | 160 | 160 |
| 01/16 | 160 μg | 160 | 160 | 160 | 160 | 160 | 160 |
| 01/21 | 160 μg | 160 | 160 | 160 | 160 | 160 | 160 |
| 01/09 | 320 μg | 320 | 320 | 320 | 320 | 320 | 320 |
| 01/14 | 320 μg | 320 | 160 | 320 | 320 | 320 | 320 |
| 01/01 | 480 μg | 480 | 480 | 480 | 480 | 480 | 480 |
| 01/03 | 480 μg | 480 | 480 | 480 | 480 | 480 | 480 |
| 01/17 | 480 μg | 480 | 480 | 240 | 240 | 240 | 240 |
| 01/02 | 640 μg | 640 | 320 | 640 | 640 | 160 | 0 |
| 01/08 | 640 μg | 640 | 640 | 640 | 640 | 640 | 640 |
| 01/13 | 640 μg | 640 | 640 | 640 | 640 | 640 | 640 |
| 02/06 | 160 μg | 160 | 160 | 160 | 160 | 160 | 160 |
| 02/07 | 160 μg | 160 | 160 | 160 | 160 | 160 | 160 |
| 02/04 | 320 μg | 320 | 320 | 320 | 320 | 320 | 320 |
| 02/15 | 320 μg | 320 | 320 | 320 | 320 | 320 | 320 |
| 02/01 | 480 μg | 480 | 480 | 480 | 480 | 480 | 480 |
| 02/11 | 480 μg | 480 | 480 | 480 | 480 | 480 | 480 |
| 02/03 | 640 μg | 640 | 640 | 640 | 640 | 640 | 640 |
| 02/13 | 640 μg | 640 | 640 | 640 | 640 | 640 | 640 |
| 03/07 | 160 μg | 160 | 160 | 160 | 160 | 160 | 160 |
| 03/08 | 160 μg | 160 | 160 | 160 | 160 | 160 | 160 |
| 03/11 | 160 μg | 160 | 160 | 160 | 160 | 160 | 160 |
| 03/05 | 320 μg | 320 | 320 | 320 | 320 | 320 | 320 |
| 03/06 | 320 μg | 320 | 320 | 320 | 320 | 320 | 320 |
| 03/15 | 320 μg | 320 | 320 | 320 | 320 | 320 | 320 |
| 03/17 | 320 μg | 320 | 320 | 320 | 320 | 320 | 320 |
| 03/02 | 480 μg | 480 | 480 | 480 | 480 | 480 | 480 |
| 03/04 | 480 μg | 480 | 480 | 480 | 480 | 480 | 480 |
| 03/12 | 480 μg | 480 | 480 | 480 | 480 | 480 | 480 |

TABLE 1

Disposition of patients (All Patients; N = 32)

| | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|
| Completed study | 8 (100.0) | 8 (100.0) | 8 (100.0) | 7 (87.5) | 31 (96.9) |
| Withdrew from study | 0 (0.0) | 0 (0.0) | 0 (0.0) | 1 (12.5) | 1 (3.1) |

Data Sets Analysed

Patients were randomised into one of four treatment groups. A total of 32 patients were included in the Safety Population and 31 were included in the per protocol set (PPS) Population, as summarized in Table 2.

TABLE 2

Analysis populations by treatment group (All Patients; N = 32)

| | LOCTERON ™ 160 μg N (%) | LOCTERON ™ 320 μg N (%) | LOCTERON ™ 480 μg N (%) | LOCTERON ™ 640 μg N (%) | Total N (%) |
|---|---|---|---|---|---|
| Safety Population[1] | 8 (100) | 8 (100) | 8 (100) | 8 (100) | 32 (100) |
| PPS Population[2] | 8 (100) | 8 (100) | 8 (100) | 7 (87.5)* | 31 (96.9) |

*One patient was not included in PPS Population as a result of being withdrawn from the study due to an adverse event (AE)
[1] The Safety Population was defined as all patients who received at least one dose of study treatment
[2] The PPS Population was defined as all randomised patients who completed the study without any major protocol violations TABLE 3-continued LOCTERON ™ doses administered by individual patient (Safety Population; N = 32)

| Patient | Dose | Day 1 $1^{st}$ dosing | Day 15 $2^{nd}$ dosing | Day 29 $3^{rd}$ dosing | Day 43 $4^{th}$ dosing | Day 57 $5^{th}$ dosing | Day 71 $6^{th}$ dosing |
|---|---|---|---|---|---|---|---|
| 03/01 | 640 μg | 640 | 640 | 640 | 640 | 640 | 640 |
| 03/03 | 640 μg | 640 | 640 | 640 | 640 | 640 | 640 |
| 03/10 | 640 μg | 640 | 640 | 640 | 640 | 640 | 640 |

Regarding safety laboratory results in the three lower treatment groups, only 1 patient had a platelet count fall below $100\times10^9$/L, with a minimum value of $50\times10^9$/L. This patient (Patient 01/17) had been randomized to a dose of 480 μg of Locteron™ and had the dose reduced to 240 μg as from the $3^{rd}$ dose. This patient's initial platelet count was $120\times10^9$/L and the platelet count remained between 70 and $90\times10^9$/L following dose reduction. In 2 patients the absolute neutrophil count fell below $0.75\times10^9$/L. One patient (Patient 01/14), randomized to 320 μg, had a nadir count of $0.51\times10^9$/L on Day 3. After reducing the $2^{nd}$ dose to 160 μg for a single injection, the neutrophil count returned to $>0.75\times10^9$/L and the patient's dose was returned to the assigned dose of 320 μg. One patient (Patient 01/02), randomized to 640 μg, showed a neutrophil count of $0.70\times10^9$/L in Week 9/Day 57. In that patient the $2^{nd}$ dose had been reduced to 320 μg, after which the patient was returned to the randomized 640 μg for the $3^{rd}$ and $4^{th}$ dose. The $5^{th}$ dose was lowered to 160 μg, and the patient was discontinued prior to receiving a $6^{th}$ dose.

One patient (patient 02/15) in the 320 μg treatment group reported a total bilirubin value of 102 mmol/L (normal range 0-19 mmol/L) on Day 8 after treatment start. In all other patients, total bilirubin values did not exceed 3×ULN. Direct bilirubin levels did not exceed 3×ULN in any patient. Patients with the most pronounced change of total and direct bilirubin, i.e. Patients 01/14 and 02/15, were also the patients with the most distinct effect on haemoglobin. Over the first two treatment weeks they experienced 18% and 25% decreases from high-normal haemoglobin at baseline, respectively, which resulted in levels below the lower limit of normal on Day 43 for both patients. Increased total bilirubin with reduced haemoglobin is consistent with ribavirin-induced haemolytic anaemia, rather than an interferon-related effect.

No patients were discontinued from treatment for any bilirubin-related observation. In Patient 02/15 (320 μg treatment group) with moderately increased total bilirubin on Day 8, the ribavirin dose was reduced from 800 mg to 600 mg from Day 11 until Day 15, and returned to 800 mg from Day 16 until the end of the study. In all other patients, the ribavirin dose remained unchanged throughout the study. Based upon further evaluation, this observation in Patient 02/15 was interpreted as Gilbert syndrome. Mild dehydration and eating less after the $1^{st}$ injection of Locteron™ were considered the triggers for making the clinical manifestation of Gilbert syndrome in this case.

Efficacy Analysis

Primary Efficacy Endpoint

Figure 1A:
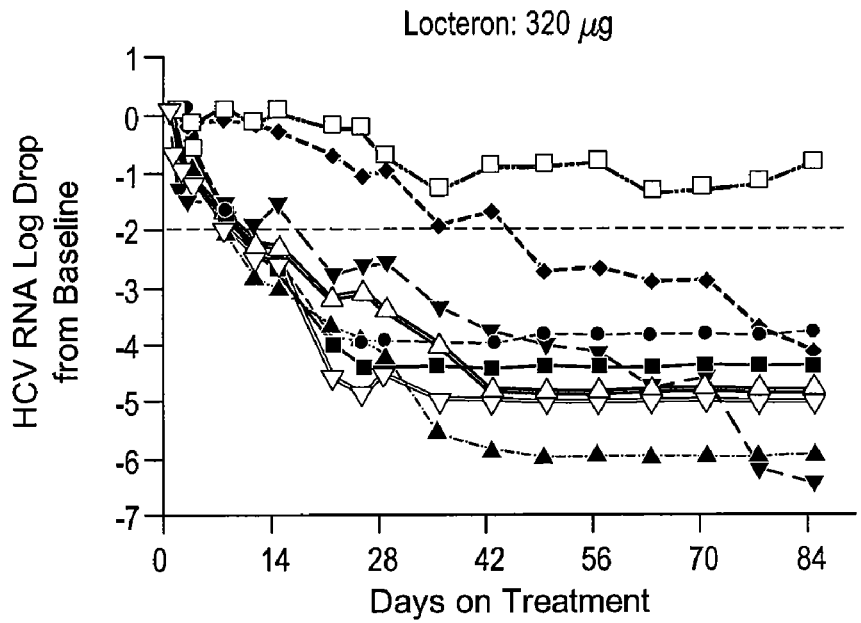
Figure 1B:
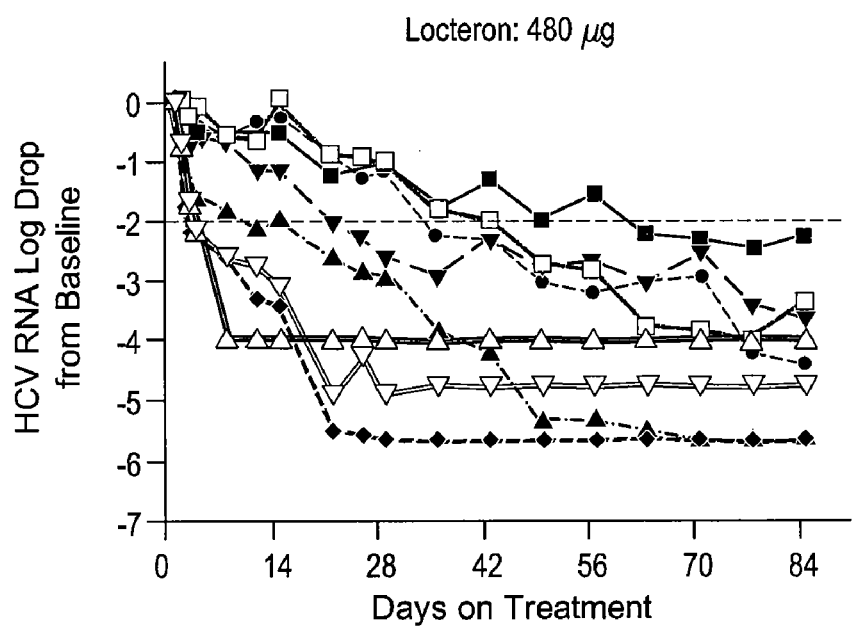
Figure 1C:
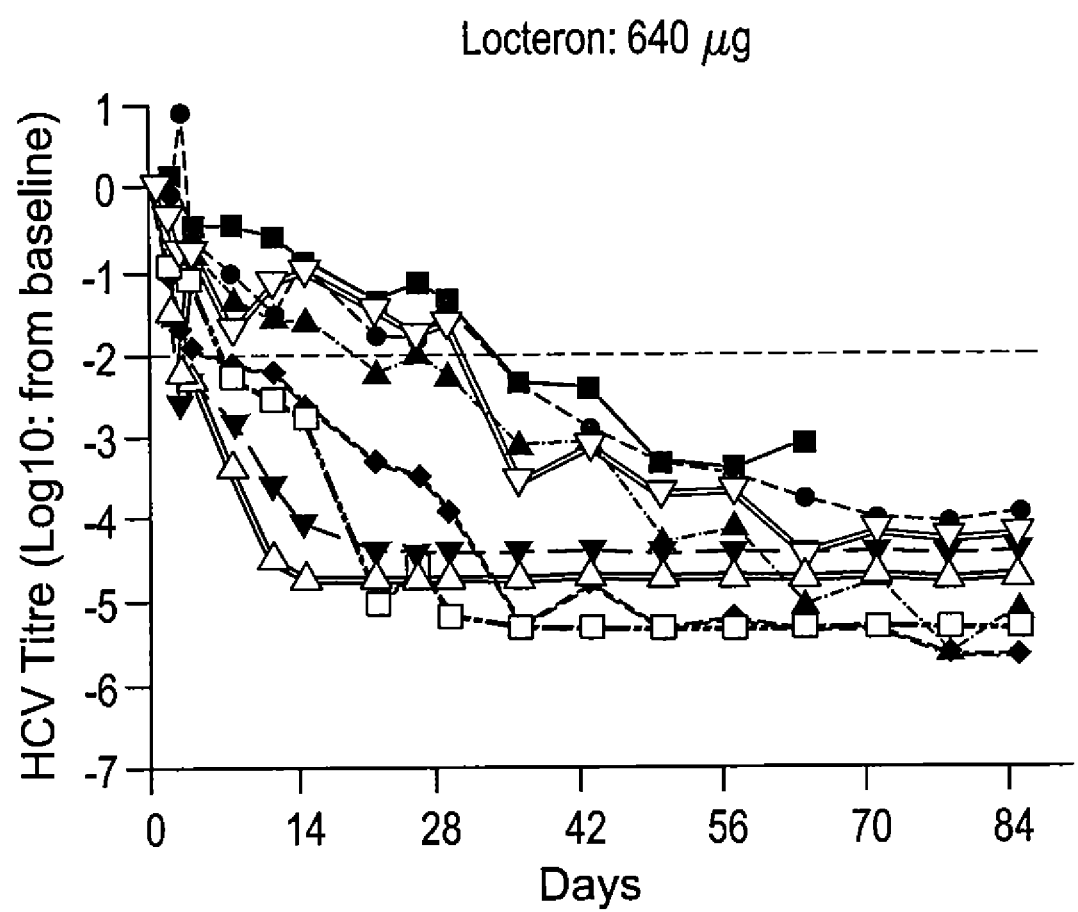
Figure 1D:
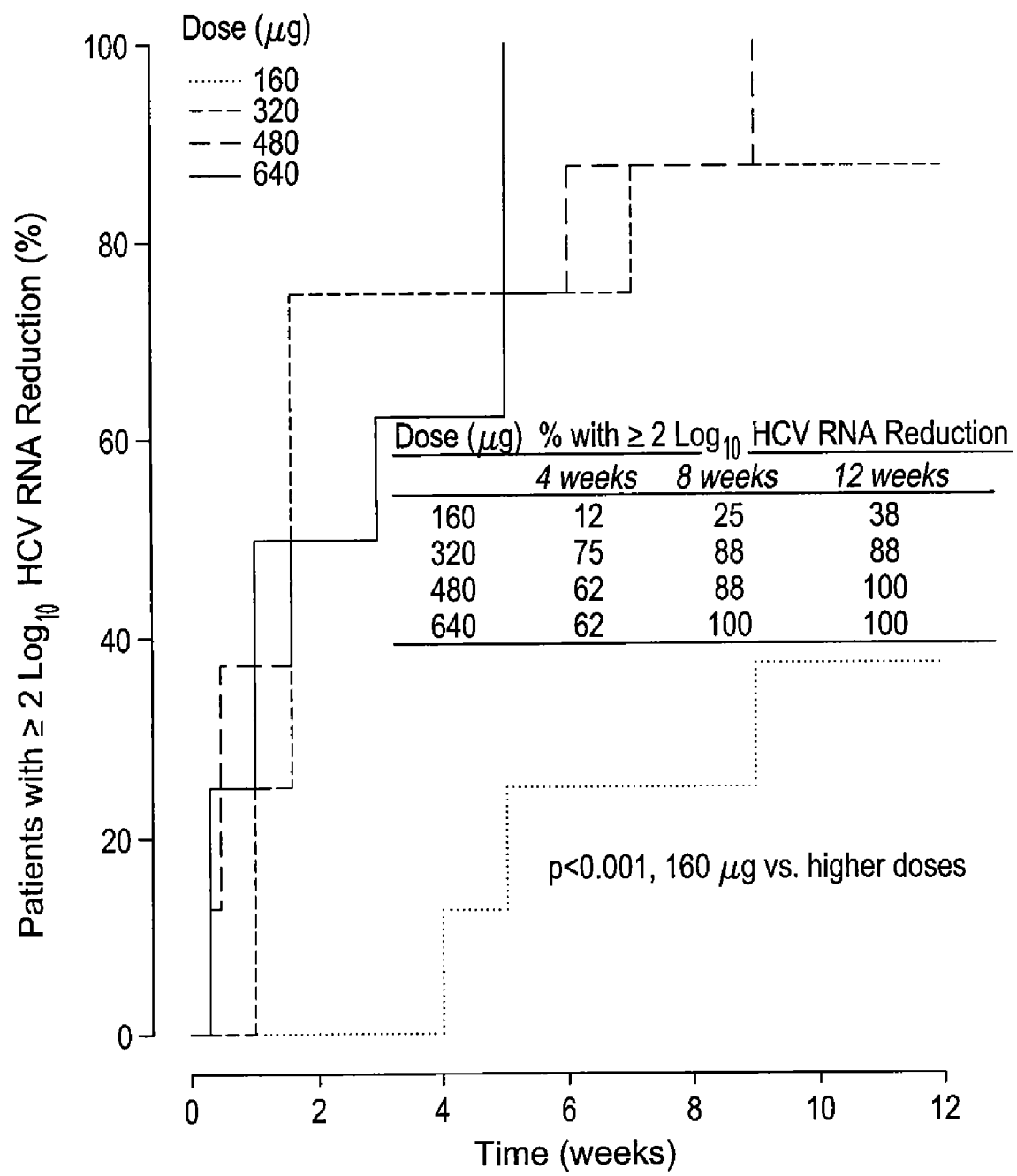
Figure 1E:
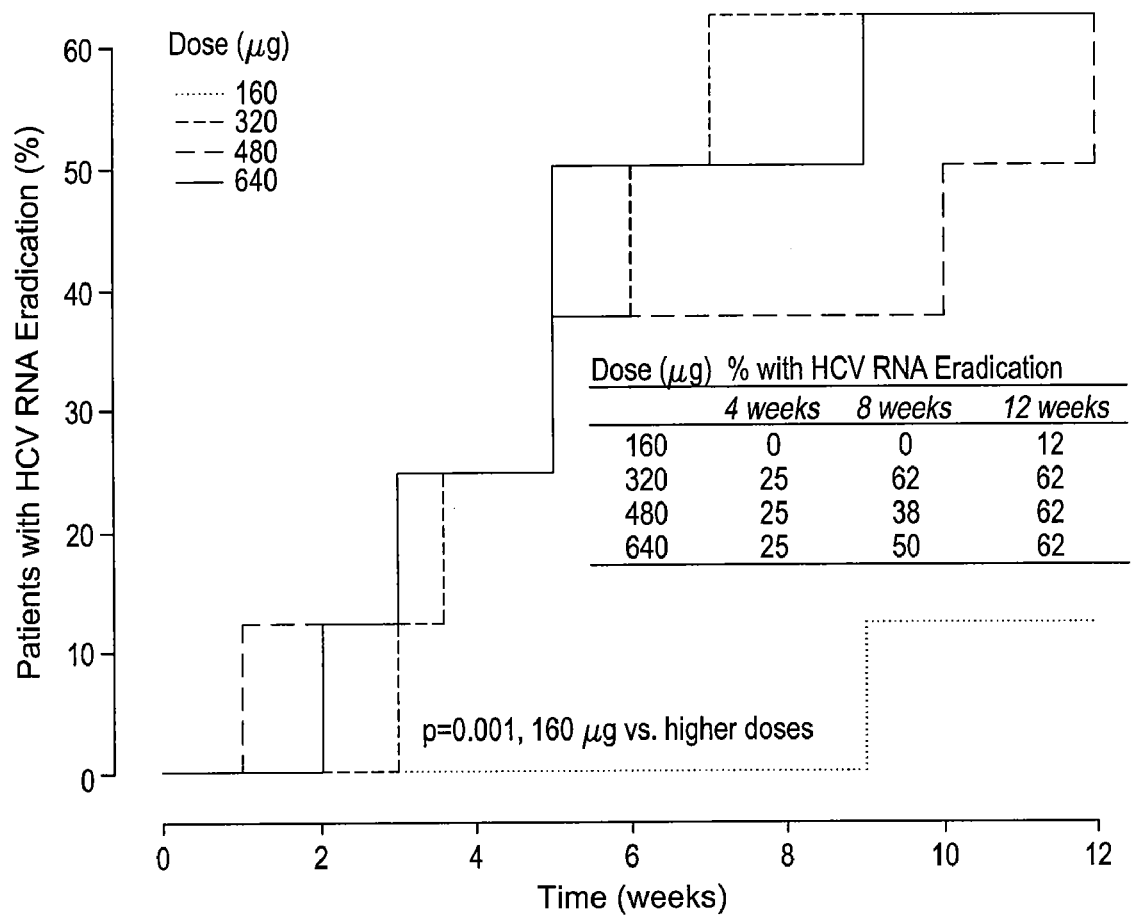
Figure 2A:
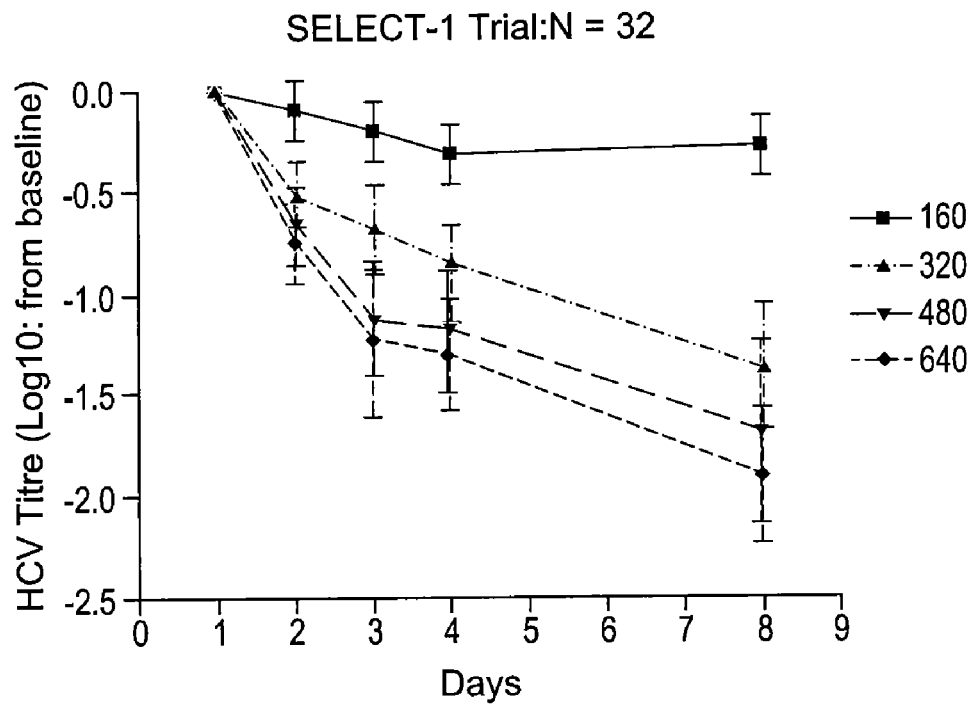
FIGS. 2A-2C show the average HCV RNA log reduction for the four study groups using different time-scales (1 week, 4 weeks and 12 weeks, respectively).
Figure 2B:
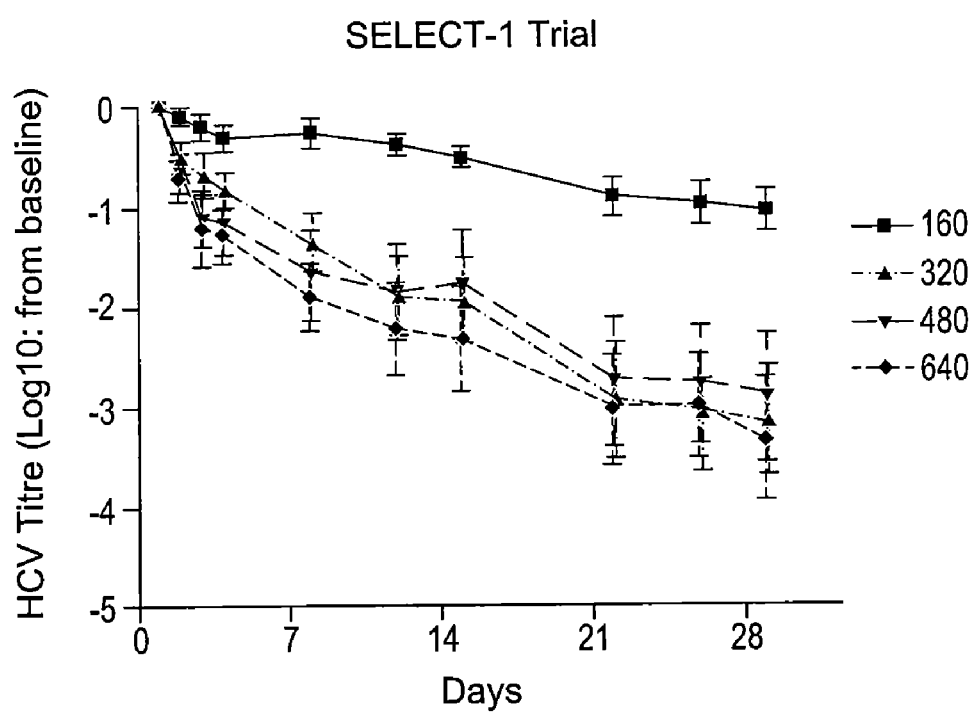
Figure 2C:
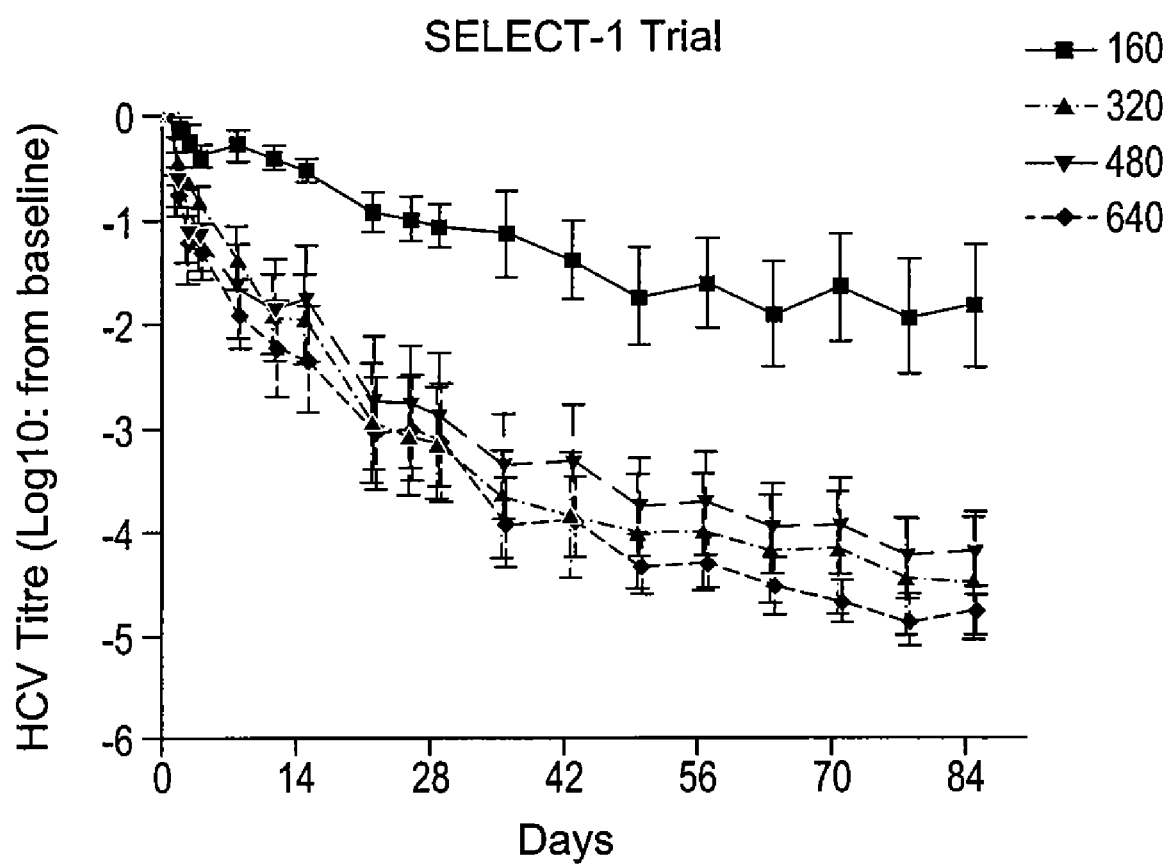
Figure 3:
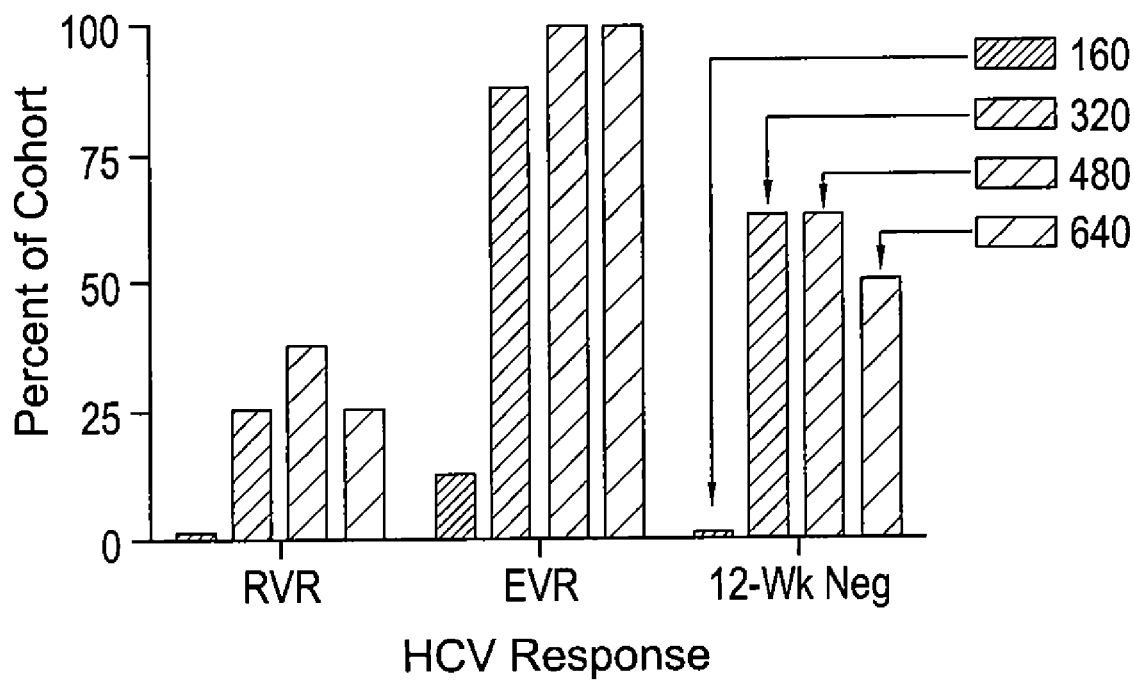
FIG. 3 shows percent of cohorts that exhibited greater than 4 log reduction in HCV RNA.
Figure 4A:
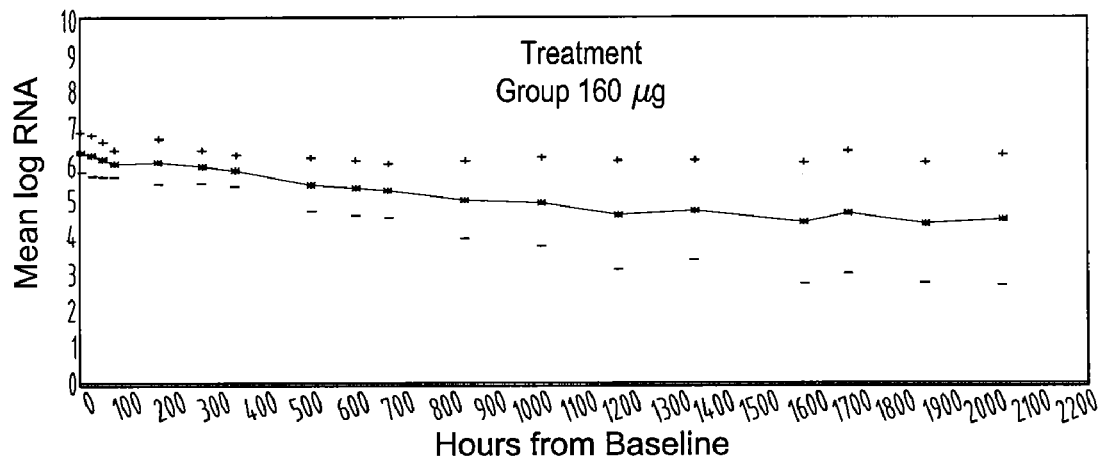
FIGS. 4A-4D show estimates of mean $LOG_{10}$ (HCV RNA) ±standard deviation by time and treatment group (Safety Population; N=32).
Figure 4B:
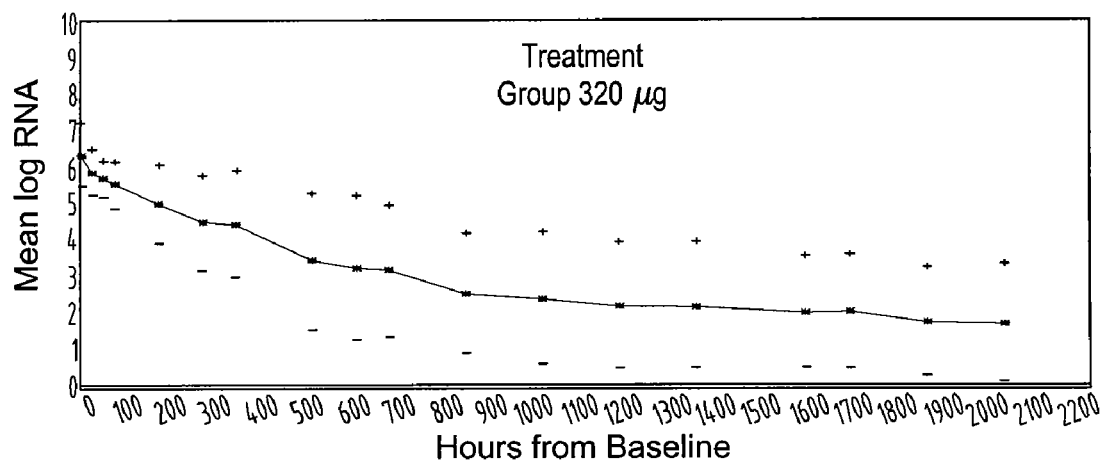
Figure 4C:
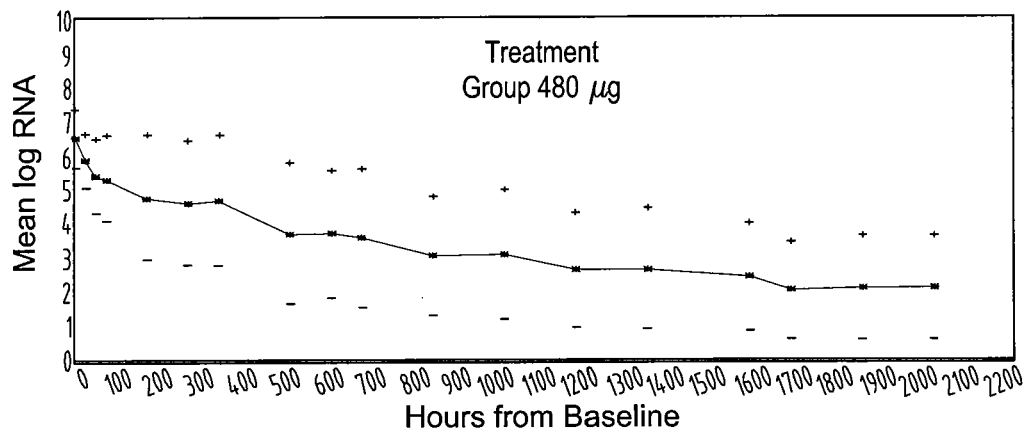
Figure 4D:
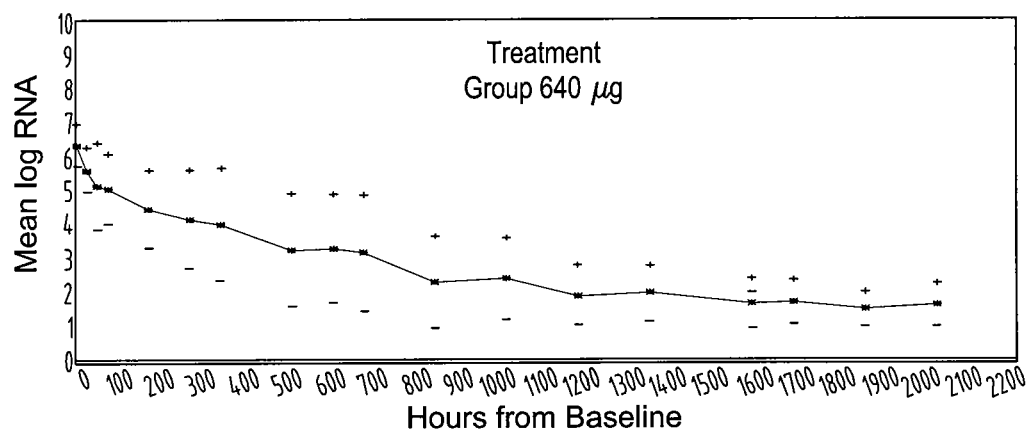

The primary efficacy endpoint in this study was the log decrease in hepatitis C virus (HCV) RNA after 4 weeks (Week 5/Day 29) compared to Baseline/Day 1. The change in patient's HCV RNA levels after 4 weeks compared to Baseline/Day 1 in the Safety Population is summarised in Table below. FIG. 1A-1C show individual HCV RNA log reduction for 32 study subjects. FIG. 1D shows Kaplan-Meier analysis of first times $\geq 2$ log10 reduction in HCV RNA level for the four dose groups. FIG. 1E shows Kaplan-Meier analysis of first times to HCV RNA eradication for the four dose groups. FIGS. 2A-2C show the average HCV RNA log reduction for the four study groups using different time-scales (1 week, 4 weeks and 12 weeks, respectively). Table 4 shows percentage of subjects that exhibit more than 2 log reduction in HCV RNA 12 weeks after administration of controlled release formulation vis-à-vis prior art interferon formulations. FIG. 3 shows percent of cohorts that exhibited greater than 4 log reduction in HCV RNA.

TABLE 4

Percentage of subjects that exhibit more than 2log reduction in HCV RNA12 weeks after administration of controlled release formulation vis-à-vis prior art interferon formulations.

| Results | Locteron SELECT-1 phase II | | | | | Albuferon[3] | |
|---|---|---|---|---|---|---|---|
| 12 Weeks of Treatment | 320 μg | 480 μg | 640 μg | PEG Intron[1] | Pegasys[2] | 900 μg | 1200 μg |
| % of Patients with Early Virologic Response (>2 log drop in | 88 | 100% | 100% | 74% | 81% | 84% | 90% |

[1]Davis, et al, J. Hepatl 2003
[2]Ferenci, et al, J. Hepatl. 2005
[3]2006 Annual European Association Meeting for the Study of the Liver, Zeuzem et al.

TABLE 5

Summary of log drops in HCV RNA levels after 4 weeks compared to Baseline/Day 1 (Safety Population; N = 32)

| | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|
| Mean log decrease | −1.05 | −3.21 | −2.97 | −3.20 | −2.61 |
| SD | 0.590 | 1.574 | 1.849 | 1.672 | 1.698 |

Abbreviations:
SD = Standard Deviation.

After 4 weeks of treatment, Locteron™, at doses of 160 μg, 320 μg, 480 μg and 640 μg induced 1.05, 3.21, 2.97 and 3.20 log drops in HCV RNA, respectively, compared to at Baseline/Day 1. In total, a mean of 2.61 log drops were seen after 4 weeks. Similar results were observed in the PPS population.

Secondary Efficacy Endpoints

The proportion of patients in each arm of the study showing a two log or greater drop in HCV RNA after 12 weeks of treatment (Week 13/Day 85) compared to Baseline/Day 1 in the Safety population is summarized in Table 6 below.

TABLE 6

Summary of patients achieving at least a two log drop in HCV RNA levels after 12 weeks of treatment compared to Baseline/Day 1 (Safety Population; N = 32)

|  | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 31 n (%) |
|---|---|---|---|---|---|
| At least a two log drop | 3 (37.5) | 7 (87.5) | 8 (100.0) | 7 (87.5)* | 25 (78.1) |
| Less than a two log drop | 5 (62.5) | 1 (12.5) | 0 (0.0) | 0 (0.0)* | 6 (18.8) |
| 80% CI | (0.1, 0.7) | (0.6, 1.0) | (0.7, 1.0) | (0.7, 1.0) | (0.7, 0.9) |
| 95% CI | (0.1, 0.8) | (0.5, 1.0) | (0.6, 1.0) | (0.6, 1.0) | (0.6, 0.9) |

Abbreviations:
CI = Confidence Interval.
*One patient (Patient 01/02) from the 640 μg group was withdrawn from the study prior to Week 13/Day 85 due to AE The majority of patients in the Safety Population (25 patients, 78.1%) had at least a two log drop from Baseline/Day 1 in HCV RNA levels after 12 weeks. In the 160 μg treatment group 5 patients (62.5%) had less than a two-log drop in HCV RNA levels after 12 weeks. In contrast, the majority of patients achieved at least a two-log drop in HCV RNA after 12 weeks in the 320 μg (7 patients, 87.5%), 480 μg (8 patients, 100%) and 640 μg (7 patients, 87.5%) treatment groups. In the 640 group, Patient 01/02 had reached a three log drop to 242 IU/mL before treatment was discontinued. Similar results were observed in the PPS population.

The proportion of patients with HCV RNA eradication (levels below LLQ 28 IU/mL), measured using Roche Taqman after 12 weeks of treatment (Week 13/Day 85) is summarised in Table 7 below.

TABLE 7

Summary of patients achieving HCV RNA eradication after 12 weeks of treatment compared to Baseline/Day 1 (Safety Population; N = 32)

|  | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|
| HCV RNA eradication | 1 (12.5) | 5 (62.5) | 5 (62.5) | 4 (50.0)* | 15 (46.9) |
| No HCV RNA eradication | 7 (87.5) | 3 (37.5) | 3 (37.5) | 3 (37.5)* | 16 (50.0) |
| 80% CI | (0.0, 0.4) | (0.3, 0.9) | (0.3, 0.9) | (0.3, 0.8) | (0.4, 0.6) |
| 95% CI | (0.0, 0.5) | (0.2, 0.9) | (0.2, 0.9) | (0.2, 0.9) | (0.3, 0.7) |

Abbreviations:
CI = Confidence Interval.
*One patient (Patient 01/02) from the 640 μg group was withdrawn from the study prior to Week 13/Day 85 due to AE
Footnote 1:
HCV eradication corresponds to the levels below LLQ 28 IU/mL After 12 weeks of treatment, 15 patients (46.9%) in the Safety Population had HCV RNA eradication. In the 160 μg treatment group, only one patient (12.5%) had HCV RNA eradication after 12 weeks. HCV RNA eradication was observed in the 320 μg (5 patients, 62.5%), 480 μg (5 patients, 62.5%) and 640 μg treatment groups (4 patients, 50.0%), after 12 weeks. Similar results were observed in the PPS population.

The log decrease of HCV RNA levels at each visit versus Baseline/Day 1 in the Safety Population is summarised in Table 8 below.

TABLE 8

Summary of mean (SD) log decrease in HCV RNA levels from Baseline/Day 1 by treatment group (Safety Population; N = 32)

| Visit | LOCTERON ™ 160 μg n = 8 | LOCTERON ™ 320 μg n = 8 | LOCTERON ™ 480 μg n = 8 | LOCTERON ™ 640 μg n = 8 | Total n = 32 |
|---|---|---|---|---|---|
| Week 1/Day 2 | −0.09 (0.262) | −0.51 (0.458) | −0.66 (0.539) | −0.75 (0.572) | −0.50(0.517) |
| Week 1/Day 3 | −0.21 (0.372) | −0.68 (0.614) | −1.14 (0.733) | −1.23 (1.088) | −0.81(0.823) |
| Week 1/Day 4 | −0.31 (0.382) | −0.84 (0.510) | −1.18 (0.853) | −1.30 (0.773) | −0.91(0.736) |
| Week 2/Day 8 | −0.28 (0.422) | −1.37 (0.853) | −1.73 (1.356) | −1.90 (0.947) | −1.32(1.111) |
| Week 2/Day 12 | −0.39 (0.303) | −1.90 (1.082) | −1.90 (1.443) | −2.23 (1.302) | −1.60(1.290) |
| Week 3/Day 15 | −0.51 (0.289) | −1.94 (1.184) | −1.83 (1.604) | −2.37 (1.545) | −1.66(1.397) |
| Week 4/Day 22 | −0.92 (0.528) | −2.97 (1.638) | −2.82 (1.869) | −3.12 (1.609) | −2.46(1.695) |
| Week 4/Day 26 | −0.99 (0.603) | −3.13 (1.686) | −2.83 (1.697) | −3.08 (1.543) | −2.51(1.649) |

TABLE 8-continued

Summary of mean (SD) log decrease in HCV RNA levels from
Baseline/Day 1 by treatment group (Safety Population; N = 32)

| Visit | LOCTERON ™ 160 μg n = 8 | LOCTERON ™ 320 μg n = 8 | LOCTERON ™ 480 μg n = 8 | LOCTERON ™ 640 μg n = 8 | Total n = 32 |
|---|---|---|---|---|---|
| Week 5/Day 29 | −1.05 (0.590) | −3.21 (1.574) | −2.97 (1.849) | −3.20 (1.672) | −2.61(1.698) |
| Week 6/Day 36 | −1.32 (0.936) | −3.84 (1.528) | −3.48 (1.546) | −4.06 (1.369) | −3.18(1.706) |
| Week 7/Day 43 | −1.39 (1.101) | −3.98 (1.769) | −3.44 (1.648) | −3.98 (1.189) | −3.20(1.758) |
| Week 8/Day 50 | −1.74 (1.341) | −4.19 (1.686) | −3.88 (1.453) | −4.46 (0.945) | −3.57(1.709) |
| Week 9/Day 57 | −1.61 (1.246) | −4.19 (1.706) | −3.85 (1.514) | −4.40 (0.844) | −3.52(1.724) |
| Week 10/Day 64 | −1.94 (1.544) | −4.36 (1.541) | −4.10 (1.311) | −4.72 (0.882) | −3.78(1.688) |
| Week 11/Day 71 | −1.69 (1.567) | −4.33 (1.559) | −4.32 (1.410) | −4.77 (0.555) | −3.73(1.804) |
| Week 12/Day 78 | −1.98 (1.654) | −4.63 (1.649) | −4.42 (1.191) | −5.00 (0.673) | −3.97(1.780) |
| Week 13/Day 85 | −1.86 (1.753) | −4.66 (1.759) | −4.41 (1.271) | −4.89 (0.653) | −3.93(1.860) |

Abbreviations:
SD = Standard Deviation.

Mean HCV RNA levels gradually decreased from Baseline/Day 1 for all treatment groups at the majority of visits from Week 1/Day 2 to Week 13/Day 85 (FIGS. 4A-4D). The smallest mean log decrease from Baseline/Day 1 was observed in the 160 μg treatment group (−1.86) at Week 13/Day 85. All other treatment groups had larger mean log decreases; the 320 μg treatment group had a mean log decrease of −4.66 from Baseline/Day 1, the 480 μg treatment group had a mean log decrease from Baseline/Day 1 of −4.41 and the 640 μg treatment group had a mean log decrease from Baseline/Day 1 of −4.89. Similar trends were observed in the PPS population.

Pharmacokinetic/Pharmacodynamic Analysis

Pharmacokinetic assessments (N=542) from 32 patients were available over a 14-week period following Locteron™ administration once every two weeks for 12 weeks, at one of four doses (160 μg, 320 μg, 480 μg and 640 μg). There were two missing pre-dose PK assessments for Patient 01/02 at weeks 11 and 13. A total of 351 assessments were available over the 2-week period following the first dose.

PD assessments (N=381) from 32 patients were available over a 13-week period following Locteron™ administration once every two weeks for 12 weeks, at one of four doses (160 μg, 320 μg, 480 μg and 640 μg). There was an additional unscheduled neopterin assessment for Patient 03/10 at Week 14 (Follow-up). There were two missing PD assessments for Patient 01/02 at weeks 11 and 13 and there was insufficient sample for analysis for Patient 03/05 at Week 2. A total of 191 assessments were available over the 2-week period following the first dose.

With regard to PK/PD data, pairs of serum IFNα2b and 2',5'-OAS or neopterin levels (N=350) were available from 32 patients over a 13-week period following Locteron™ administration once every two weeks for 12 weeks, at one of four doses (160 μg, 320 μg, 480 μg and 640 μg). There was an additional pair of serum IFNα2b and neopterin levels for Patient 03/10 at Week 14/Day 92.

Pharmacokinetic Results

All PK results are presented in full in the PK/PD analysis report in Appendix 14.5.

Figure 5:
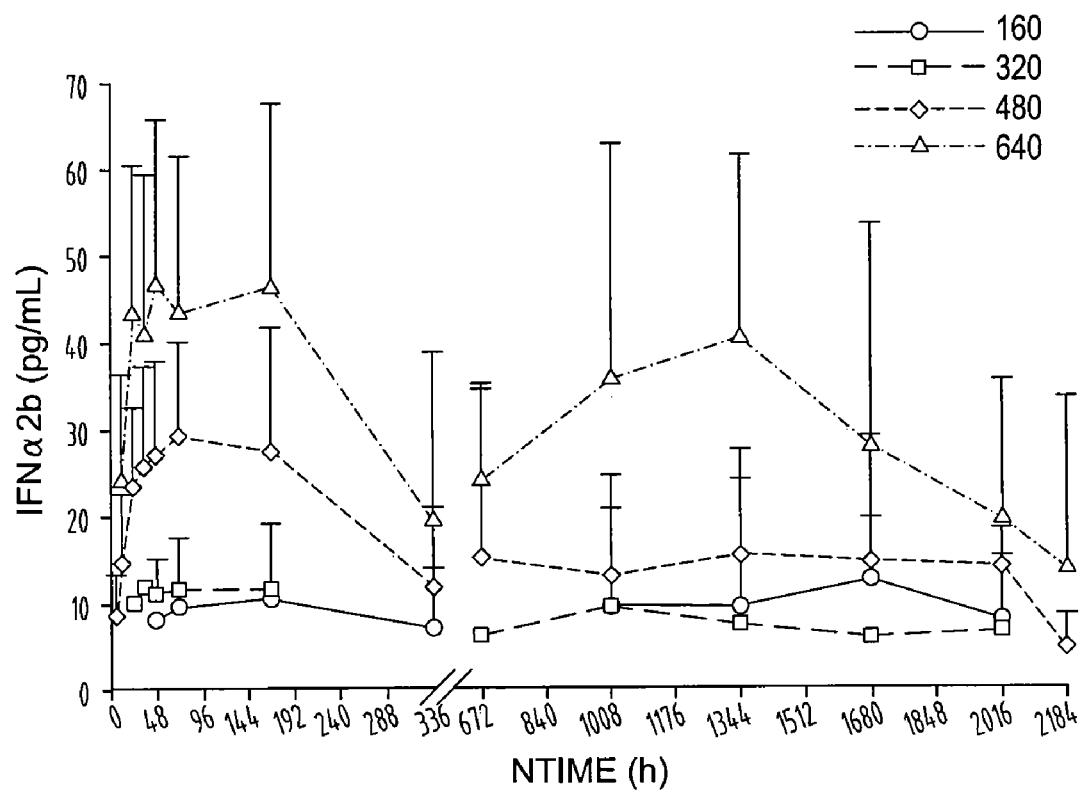
FIG. 5 shows mean (+SD) serum IFNα2b profiles (PK Population; N=32).

Mean (+SD) serum concentration-time IFNα2b profiles for all doses are presented in FIG. 5. Table 9 presents the summary PK parameters following the first dose.

TABLE 9

Summary of IFNα2b NCA pharmacokinetic results following
the first dose (PK Population; N = 32)

| | | Dose | | | |
|---|---|---|---|---|---|
| | | 160 μg | 320 μg | 480 μg | 640 μg |
| | N | 7[1] | 8 | 8 | 8 |
| Cmax (pg/mL) | Mean | 13.821 | 15.171 | 31.594 | 49.300 |
| | CV % | 69.3 | 41.0 | 36.8 | 37.9 |
| $T_{max}$ (h) | Median | 72.0 | 60.0 | 116.9 | 48.0 |
| | Range | 24-168 | 36-336 | 36-168 | 24-169 |
| $AUC_{last}$ (pg · h/mL) | Mean | 3232.02 | 2779.12 | 7538.01 | 12337.36 |
| | CV % | 67.9 | 58.9 | 48.8 | 52.8 |
| $AUC_{0-14}$ (pg · h/mL) | Mean | 3477.71[N=6] | NC[N=4] | NC[N=5] | 13306.53[N=6] |
| | CV % | 66.1 | NC[N=4] | NC[N=5] | 46.9 |

Figure 6:
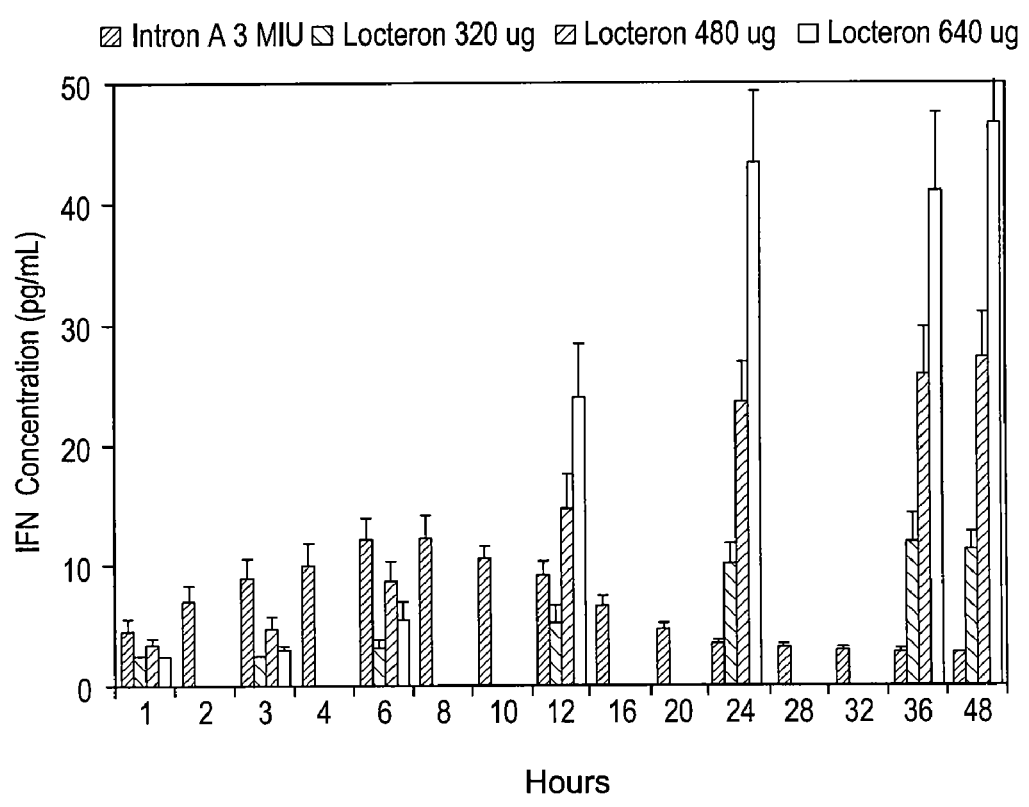
FIG. 6 shows the mean±SD plasma levels of IFNα2b over time for commercial interferon-α product (Intron A 3 MIU) and Locteron™ 320 μg, 480 μg, and 640 μg.

[1]Patient 03/08 IFNα2b concentrations were <2.5 pg/mL at all times
NC: Not calculable FIG. 6 shows the mean±SD plasma levels of IFNα2b over time for commercial interferon-α product (Intron A 3 MIU) and Locteron™ 320 μg, 480 μg, and 640 μg. The figure shows that while the time to $C_{max}$ (after the first dose) for the commercial product is about 6-8 hours, the time to $C_{max}$ (after the first dose) for the formulations of the present invention is more than about 48 hours.

Following the 160 μg and 320 μg doses, the majority of the patients had IFNα2b concentrations <2.5 pg/mL for the first 24 h post first dose. Mean profiles were flat and appeared superimposable, however great variability was associated with the data.

Following the 480 μg and the 640 μg doses, mean IFNα2b concentrations rose until about 168 h post first dose and then declined. It should be noted that one patient (Patient 01/02) in the 640 μg group had high IFNα2b levels after the first 640 μg dose, exceeding 80 pg/mL between Days 2 and 8, and was later discontinued from the study. An apparent steady state mean trough value was achieved for the 480 μg dose after the second dose, while for the 640 μg dose IFNα2b mean trough values continued to rise until 1344 h post first dose (pre-dose 5 on Day 57, Week 9) and then declined.

Mean $C_{max}$ following the first dose was similar for the 160 μg and 320 μg doses, approximately double for the 480 μg dose and more than triple for the 640 μg dose with $AUC_{last}$ following the same pattern. $T_{max}$ following the first dose ranged from 48 to 116.9 h, indicating large inter-individual variability, therefore the median $T_{max}$ values (ranging from 60.0 to 116.9 h) did not reflect a meaningful difference between doses.

Pharmacodynamic Results—2',5'-OAS

Figure 7:
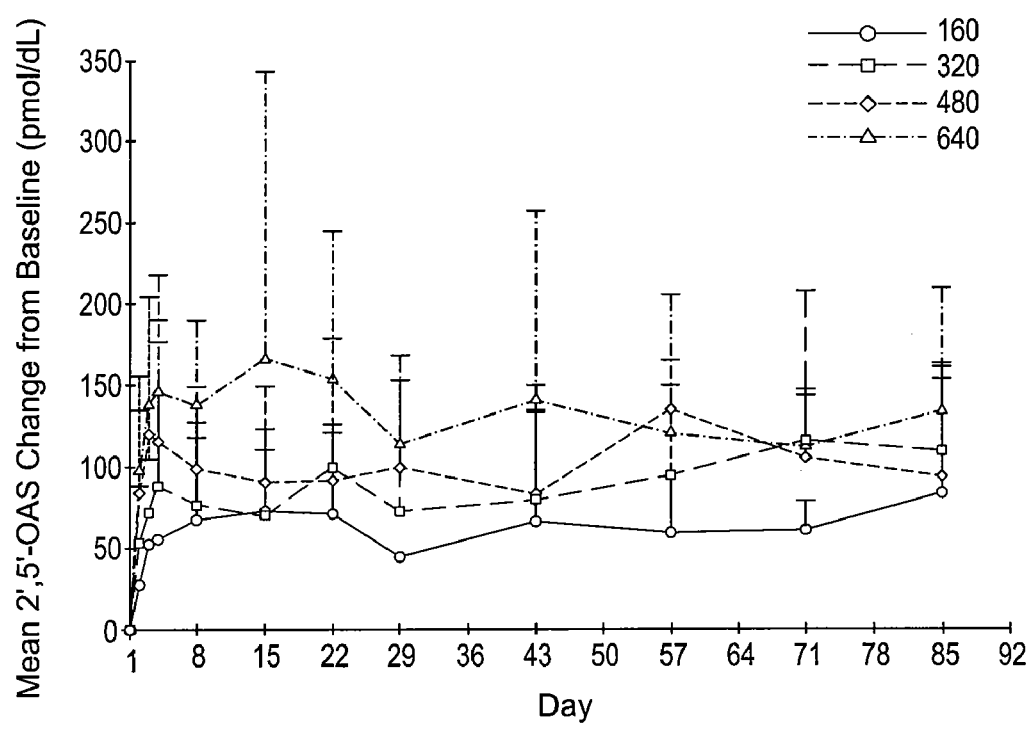
FIG. 7 shows mean (+SD) 2',5'-OAS change from baseline (PD Population; N=32).

Mean (+SD) change from baseline 2',5'-OAS serum concentration-time profiles for all doses are presented in FIG. 7 (negative change from baseline values set to zero).

The change in 2',5'-OAS levels from baseline rose steadily, and relatively stable trough levels that increased with dose appear to be achieved by Day 8 for all dose levels.

A summary of the change in 2',5'-OAS from baseline is provided in Table 10 below. FIG. 7 shows mean (+SD) 2',5'-OAS change from baseline (PD Population; N=32).

TABLE 10

Summary of 2',5'-OAS change from baseline NCA pharmacodynamic results following the first dose (PD Population; N = 32)

| | | Dose | | | |
|---|---|---|---|---|---|
| | | 160 μg | 320 μg | 480 μg | 640 μg |
| | N | 8 | 8 | 8 | 8 |
| Baseline | Mean | 77.61 | 61.76 | 62.60 | 43.33 |
| (pmol/dL) | CV % | 68.6 | 107.2 | 60.2 | 56.2 |
| $D_{max}$ | Mean | 81.09 | 110.09 | 147.25 | 242.06 |
| (pmol/dL) | CV % | 65.0 | 69.7 | 58.6 | 59.9 |
| $tD_{max}$ | Median | 8.0 | 6.0 | 4.0 | 8.0 |
| (Day) | Range | 8-15 | 3-15 | 3-15 | 4-15 |
| $D_{min}$ | Mean | 24.58 | 44.89 | 64.45 | 74.45 |
| (pmol/dL) | CV % | 88.7 | 77.1 | 74.4 | 32.4 |
| $tD_{min}$ | Median | 2.0 | 2.0 | 2.0 | 3.0 |
| (Day) | Range | 2-4 | 2-15 | 2-15 | 2-15 |
| $AUEC_{0-7\ Days}$ | Mean | 353.51 | 497.25 | 691.33 | 877.33 |
| (pmol · Day/dL) | CV % | 89.1 | 75.6 | 57.5 | 25.9 |
| $AUEC_{0-14\ Days}$ | Mean | 842.76 | 1011.88 | 1356.72 | 1941.89 |
| (pmol · Day/dL) | CV % | 76.9 | 61.1 | 54.2 | 40.4 |

Mean baseline 2',5'-OAS was similar for dose levels 160 to 480 μg but slightly lower for the 640 μg dose level. $D_{max}$ was achieved between Day 4 to 8 and increased with dose, as did $D_{min}$ (observed at Day 2), $AUEC_{0-7\ Days}$ and $AUEC_{0-14\ Days}$.

Pharmacodynamic Results—Neopterin

Figure 8:
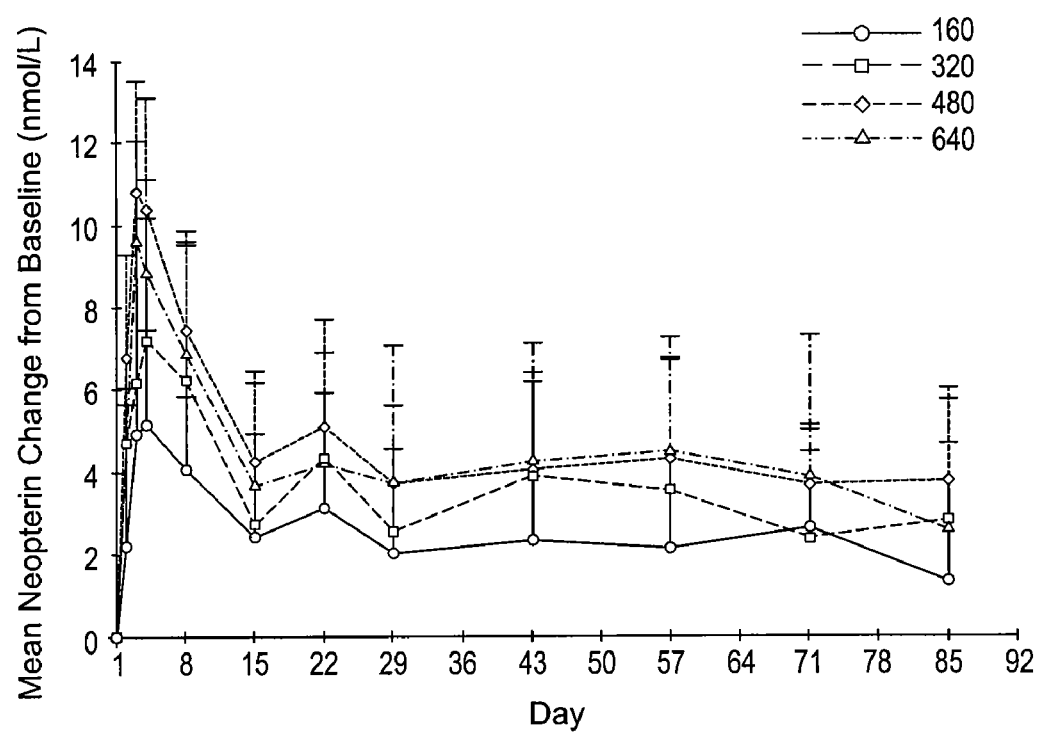
FIG. 8 shows mean (+SD) neopterin change from baseline (PD Population; N=32)

Mean (+SD) change from baseline neopterin serum concentration-time profiles for all doses are presented in FIG. 8 (negative change from baseline values set to zero).

Following an initial rise in neopterin until approximately Day 4, mean change from baseline levels declined on Days 8 and 15 for all dose levels and after that relatively stable trough levels were observed. The mean profiles for doses 480 to 640 μg appear to be superimposable, while they were lower for the 320 and 160 μg dose levels.

A summary of neopterin change from baseline is provided in Table 11 below.

TABLE 11

Summary of neopterin change from baseline NCA pharmacodynamic results following the first dose (PD Population; N = 32)

| | | Dose | | | |
|---|---|---|---|---|---|
| | | 160 μg | 320 μg | 480 μg | 640 μg |
| | N | 7[1] | 8 | 8 | 8 |
| Baseline | Mean | 6.590$^{N=8}$ | 5.438 | 5.441 | 6.188 |
| (nmol/L) | CV % | 86.3 | 37.1 | 29.2 | 25.6 |
| $D_{max}$ | Mean | 6.220 | 8.026 | 11.816 | 9.673 |
| (nmol/L) | CV % | 21.0 | 41.3 | 17.2 | 25.3 |
| $tD_{max}$ | Median | 4.0 | 4.0 | 4.0 | 3.0 |
| (Day) | Range | 3-8 | 4-8 | 3-8 | 3-8 |
| $D_{min}$ | Mean | 2.010 | 2.213 | 4.011 | 3.130 |
| (nmol/L) | CV % | 39.0 | 81.2 | 52.8 | 51.4 |

TABLE 11-continued

Summary of neopterin change from baseline NCA pharmacodynamic results following the first dose (PD Population; N = 32)

| | | Dose | | | |
|---|---|---|---|---|---|
| | | 160 μg | 320 μg | 480 μg | 640 μg |
| $tD_{min}$ | Median | 15.0 | 15.0 | 15.0 | 15.0 |
| (Day) | Range | 2-15 | 2-15 | 2-15 | 2-15 |
| $AUEC_{0-7\ Days}$ | Mean | 32.108 | 39.632 | 58.483 | 50.233 |
| (nmol · Day/L) | CV % | 20.8 | 39.6 | 17.7 | 24.7 |
| $AUEC_{0-14\ Days}$ | Mean | 58.158 | 69.453 | 99.354 | 87.316 |
| (nmol · Day/L) | CV % | 17.0 | 47.8 | 18.1 | 33.7 |

[1]No parameters other than baseline were calculable for patient 01/10 due to negative change from baseline profile at all time points Mean baseline neopterin was similar for dose levels 320 to 640 μg but slightly higher and more variable for the 160 μg dose level. $D_{max}$ was achieved at about Day 4 and $D_{min}$ at Day 15. $D_{max}$, $D_{min}$, $AUEC_{0-7\ Days}$ and $AUEC_{0-14\ Days}$ increased with dose for doses 160 to 480 μg, while the estimates of these parameters for the 640 μg dose level were slightly lower than those for the 480 μg dose level.

FIGS. 9a and 9b show linear regression analysis of (a) neopterin and (b) 2,5-OAS AUC as a function of Locteron dose. Data points depict individual patient AUC values. Dashed lines indicate the 95% confidence intervals of the regressions and dotted lines the 95% prediction intervals for new observations. Abbreviations: AUC, area under the time-concentration curve; CI, 95% confidence interval.

Efficacy/Pharmacokinetic/Pharmacodynamic Conclusions

The mean age of patients in this study was 37.9 years and all were Caucasian. There were more male than female patients overall (20 vs 12 respectively). The majority of patients were 100% treatment compliant for Locteron™. The mean patient compliance for ribavirin was greater than 97% in all cases.

The change in patients' HCV RNA levels was assessed in the Safety Population after 4 weeks (Week 5/Day 29) and after 12 weeks of treatment (Week 13/Day 85). For the primary efficacy endpoint, i.e. the log drop in HCV RNA levels observed after 4 weeks, mean log drops in HCV RNA of 1.05, 3.21, 2.97 and 3.20 were observed in the 160 μg, 320 μg, 480 μg and 640 μg groups, respectively. A mean log drop of 2.61 was observed in total after 4 weeks. Similar results were observed in the PPS population.

The majority of patients in the Safety Population (25 patients, 78.1%) had at least a two log drop in HCV RNA levels after 12 weeks. In the 480 μg treatment group, all patients achieved at least a two-log drop after 12 weeks and the majority of patients in the 320 μg treatment group (7 patients, 87.5%) and 640 μg group (7 patients, 87.5%) also achieved at least a two log drop. With regard to the patient who was discontinued after a three log drop before Week 13/Day 85, it was concluded that all patients in the 640 μg group reached at least a two log drop at some time point before or after 12 weeks. In the 160 μg treatment group, 3 patients (37.5%) achieved a two-log drop. Similar results were observed in the PPS population.

After 12 weeks of treatment, 15 patients (46.9%) had HCV RNA eradication. For the 320 μg, 480 μg and 640 μg treatment groups, HCV RNA eradication was observed after 12 weeks (5 patients, 62.5%, 5 patients, 62.5%, and 4 patients, 50.0%, respectively) but this was not the case in the 160 μg treatment group, with only one patient (12.5%) having HCV RNA eradication at Week 13/Day 85. Similar results were observed in the PPS population.

Mean HCV RNA levels gradually decreased from Baseline/Day 1 for all treatment groups at the majority of visits from Week 1/Day 2 to Week 13/Day 85. The smallest mean log decrease from Baseline/Day 1 was observed in the 160 μg treatment group (−1.86) at Week 13/Day 85. All other treatment groups had larger mean log decreases; the 320 μg treatment group had a mean log decrease of −4.66 from Baseline/Day 1, the 480 μg treatment group had a mean log decrease from Baseline/Day 1 of −4.41 and the 640 μg treatment group had a mean log decrease from Baseline/Day 1 of −4.89. Similar trends were observed in the PPS population.

Following the 160 μg and 320 μg doses, the majority of the patients had IFNα2b concentrations <2.5 pg/mL for the first 24 h post first dose. Mean profiles were flat and appeared superimposable, however great variability was associated with the data. Following the 480 μg and the 640 μg doses, mean IFNα2b concentrations rose until about 168 h post first dose and then declined. An apparent steady state mean trough value was achieved for the 480 μg dose after the second dose, while for the 640 μg dose IFNα2b mean trough values continued to rise until 1344 h post first dose (pre-dose 5 on Day 57, Week 9) and then declined.

Mean $C_{max}$ following the first dose was similar for the 160 μg and 320 μg doses, approximately double for the 480 μg dose and more than triple for the 640 μg dose with $AUC_{last}$ following the same pattern. $T_{max}$ following the first dose ranged from 48 to 117 h, indicating large inter-individual variability, therefore the median $T_{max}$ values (ranging from 60.0 to 117 h) did not reflect a meaningful difference between doses.

There was a steady rise from Baseline/Day 1 in 2′,5′-OAS levels, and relatively stable trough levels appeared to be achieved by Day 8 for all dose levels. Mean baseline 2′,5′-OAS was similar for dose levels 160 to 480 μg but slightly lower for the 640 μg dose level. $D_{max}$ was achieved between Day 4 to 8 and increased with dose, as did $D_{min}$ (observed at Day 2), $AUEC_{0-7\ Days}$ and $AUEC_{0-14\ Days}$.

Following an initial rise in neopterin until about Day 4, mean change from baseline levels declined on Days 8 and 15 for all dose levels and after that relatively stable trough levels were observed. The mean profiles for doses 480 to 640 μg appear to be superimposable, while they were lower for the 320 and 160 μg dose levels. Mean baseline neopterin was similar for dose levels 320 to 640 μg but slightly higher and more variable for the 160 μg dose level. $D_{max}$ was achieved at about Day 4 and $D_{min}$ at Day 15. $D_{max}$, $D_{min}$, $AUEC_{0-7\ Days}$ and $AUEC_{0-14\ Days}$ increased with dose for doses 160 to 480 μg, while the estimates of these parameters for the 640 μg dose level were slightly lower than those for the 480 μg dose level.

Dose-proportionality assessment $AUC_{0-14}$ and $AUC_{inf}$ and dose-independence assessment for CL/F and $t_{1/2}$ were not performed since these parameters were not calculable for the majority of the patients. Since for the dose-dependent parameters $AUC_{last}$ and $C_{max}$, the 90% CI for the slope includes 1, dose proportionality can be concluded.

The IFNα2b $C_{50}$ and $E_{max}$ parameter estimates were slightly lower in the final model than for the base models; the population estimate for the IFNα2b $C_{50}$ was 31.8 pg/mL and for the $E_{max}$ was 13.2 nmol/L. The inter-subject variability estimates in these parameters remained the same as in the base models (54% for $C_{50}$ and 31% for $E_{max}$). For $E_0$, the population estimate was 5.90 nmol/L. There was a 10% reduction in the inter-individual variability for $E_0$ compared to the base models, while residual variability remained the same (21%).

Safety Evaluation

A total of 32 patients were randomised and received study medication. All patients received all 6 dosings of Locteron™ during the study with the exception of one patient (Patient 01/02) who did not receive one dosing at Week 11/Day 71 due to being withdrawn as a result of a SAE.

Summary of Adverse Events

Patients experiencing treatment-emergent AEs during the study are summarised in Table 12 below.

TABLE 12

Summary of patients with treatment-emergent adverse events (Safety Population; N = 32)

| | | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|---|
| Any treatment-emergent AE | | 7 (87.5) | 8 (100.0) | 8 (100.0) | 8 (100.0) | 31 (96.9) |
| Discontinued due to AE | | 0 (0.0) | 0 (0.0) | 0 (0.0) | 1 (12.5) | 1 (3.1) |
| Any serious AE | | 0 (0.0) | 0 (0.0) | 0 (0.0) | 1 (12.5) | 1 (3.1) |
| Possibly/probably related AE (by maximum severity) | Mil | 3 (37.5) | 3 (37.5) | 3 (37.5) | 1 (12.5) | 10 (31.3) |
| | Mod | 4 (50.0) | 3 (37.5) | 5 (62.5) | 6 (75.0) | 18 (56.3) |
| | Sev | 0 (0.0) | 2 (25.0) | 0 (0.0) | 1 (12.5) | 3 (9.4) |
| Death | | | | | | 0 (0.0) |

Mil.: mild;
Mod.: moderate;
Sev.: severe;
1: A patient with multiple AEs is counted only once and by the AE of maximum severity.

In the Safety Population, 31 patients (96.9%) experienced treatment-emergent AEs (including influenza-like symptoms). Of patients experiencing AEs possibly/probably related to study medication, the majority experienced AEs of maximum severity that were moderate in severity (18 patients, 56.3%) and 10 patients (31.3%) experienced AEs whose maximum severity was mild. In total, 3 patients (9.4%) experienced severe AEs and all were considered related to the study medication. This included one patient, randomised to the 640 μg Locteron™ dose, who experienced a SAE, i.e. hospitalisation with otitis and neutropenia. In this patient, treatment was discontinued after the fifth dose of Locteron™. No patients died during the study. One patient was withdrawn from the study due to AE. No notable differences were observed between treatment groups.

Display of Adverse Events

A summary of AEs (including influenza-like symptoms) experienced by >15% of patients in total in the Safety Population is presented by system organ class and preferred term in Table 13 below.

TABLE 13

Summary of adverse events experienced by >15% of patients in total by system organ class, MedDRA preferred term and treatment group (Safety Population; N = 32)

| System Organ Class Preferred Term | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|
| Any System Organ Class | 7 (87.5) | 8 (100.0) | 8 (100.0) | 8 (100.0) | 31 (96.9) |
| Musculoskeletal and connective tissue disorders | 4 (50.0) | 7 (87.5) | 7 (87.5) | 5 (62.5) | 23 (71.9) |
| Arthralgia | 2 (25.0) | 4 (50.0) | 6 (75.0) | 4 (50.0) | 16 (50.0) |
| Myalgia | 3 (37.5) | 4 (50.0) | 2 (25.0) | 4 (50.0) | 13 (40.6) |
| General disorders and administration site conditions | 5 (62.5) | 5 (62.5) | 4 (50.0) | 7 (87.5) | 21 (65.5) |
| Asthenia | 4 (50.0) | 4 (50.0) | 4 (50.0) | 7 (87.5) | 19 (59.4) |
| Pyrexia | 1 (12.5) | 2 (25.0) | 0 (0.0) | 4 (50.0) | 7 (21.9) |
| Irritability | 1 (12.5) | 1 (12.5) | 1 (12.5) | 3 (37.5) | 6 (18.8) |
| Nervous system disorders | 4 (50.0) | 3 (37.5) | 4 (50.0) | 5 (62.5) | 16 (50.0) |
| Headache | 4 (50.0) | 3 (37.5) | 2 (25.0) | 5 (62.5) | 14 (43.8) |
| Skin and subcutaneous tissue disorders | 5 (62.5) | 4 (50.0) | 4 (50.0) | 3 (37.5) | 16 (50.0) |
| Dry skin | 4 (50.0) | 3 (37.5) | 4 (50.0) | 1 (12.5) | 12 (37.5) |
| Blood and lymphatic system disorders | 1 (12.5) | 3 (37.5) | 3 (37.5) | 6 (75.0) | 13 (40.6) |
| Neutropenia | 0 (0.0) | 1 (12.5) | 1 (12.5) | 6 (75.0) | 8 (25.0) |
| Leukopenia | 0 (0.0) | 2 (25.0) | 1 (12.5) | 4 (50.0) | 7 (21.9) |
| Metabolism and nutrition disorders | 3 (37.5) | 2 (25.0) | 3 (37.5) | 5 (62.5) | 13 (40.6) |
| Decreased appetite | 3 (37.5) | 2 (25.0) | 3 (37.5) | 5 (62.5) | 13 (40.6) |
| Investigations | 3 (37.5) | 3 (37.5) | 3 (37.5) | 4 (50.0) | 13 (40.6) |
| Neutrophil count decreased | 2 (25.0) | 2 (25.0) | 2 (25.0) | 2 (25.0) | 8 (25.0) |
| White blood cell count decreased | 2 (25.0) | 1 (12.5) | 2 (25.0) | 2 (25.0) | 7 (21.9) |
| Red blood cell count decreased | 2 (25.0) | 1 (12.5) | 1 (12.5) | 2 (25.0) | 6 (18.8) |
| Haemoglobin Decreased | 1 (12.5) | 1 (12.5) | 1 (12.5) | 2 (25.0) | 5 (15.6) |
| Gastrointestinal disorders | 4 (50.0) | 1 (12.5) | 3 (37.5) | 5 (62.5) | 13 (40.6) |
| Dry mouth | 2 (25.0) | 1 (12.5) | 2 (25.0) | 0 (0.0) | 5 (15.6) |
| Psychiatric disorders | 2 (25.0) | 2 (25.0) | 4 (50.0) | 4 (50.0) | 12 (37.5) |
| Dyssomnia | 1 (12.5) | 2 (25.0) | 3 (37.5) | 3 (37.5) | 9 (28.1) |
| Respiratory, thoracic and mediastinal disorders | 1 (12.5) | 0 (0.0) | 3 (37.5) | 2 (25.0) | 6 (18.8) |
| Cough | 1 (12.5) | 0 (0.0) | 3 (37.5) | 2 (25.0) | 6 (18.8) |
| Vascular disorders | 2 (25.0) | 1 (12.5) | 2 (25.0) | 1 (12.5) | 6 (18.8) |
| Hyperaemia | 2 (25.0) | 1 (12.5) | 1 (12.5) | 1 (12.5) | 5 (15.6) |

Footnote 1:
A patient with multiple occurrences of an AE under one treatment group was counted only once in the AE preferred term for that treatment group.
Footnote 2:
A patient with multiple adverse events within a primary system organ class was counted only once in the total row.

The most frequently experienced AEs by system organ class were musculoskeletal and connective tissue disorders (23 patients, 71.9%), general disorders and administration site conditions (21 patients, 65.6%; of which 19 patients, 59.4%, experienced asthenia), nervous system disorders (16 patients, 50%) and skin and subcutaneous tissue disorders (16 patients, 50%). The most common AEs experienced by patients by preferred term were asthenia (19 patients, 59.4%), arthralgia (16 patients, 50.0%) and headache (14 patients, 43.8%). No notable differences were observed between treatment groups with the exceptions of neutropenia and leukopenia, where a higher frequency of patients in the 640 μg group (6 patients, 75.0%, and 4 patients, 50.0%, respectively) experienced these events than in all other dose groups, with no patients experiencing such events in the 160 μg group. No patient experienced body temperature greater than 38° C., which is considered to be the threshold body temperature for fever (see FIG. 10).

Analysis of Adverse Events

All AEs suspected to be related to the study medication are presented by severity (mild, moderate, or severe) in Table 15.

TABLE 15

SUMMARY OF RELATED TREATMENT EMERGENT ADVERSE EVENTS BY SYSTEM ORGAN CLASS, MedDRA PREFERRED TERM, SEVERITY AND DOSE GROUP (SAFETY POPULATION)

| System Organ Class Preferred term | Severity | Locteron 160 ug N = 8 n (%) | Locteron 320 ug N = 8 n (%) | Locteron 480 ug N = 8 n (%) | Locteron 640 ug N = 8 n (%) | Total N = 32 n (%) |
|---|---|---|---|---|---|---|
| Any System Organ Class | Mild | 3 (37.5%) | 3 (37.5%) | 3 (37.5%) | 1 (12.5%) | 10 (31.3%) |
|  | Moderate | 4 (50.0%) | 3 (37.5%) | 5 (62.5%) | 6 (75.0%) | 18 (56.3%) |
|  | Severe | 0 (0.0%) | 2 (25.0%) | 0 (0.0%) | 1 (12.5%) | 3 (9.4%) |
| BLOOD AND LYMPHATIC SYSTEM DISORDERS | | | | | | |
| LEUKOPENIA | Mild | 0 (0.0%) | 2 (25.0%) | 1 (12.5%) | 2 (25.0%) | 5 (15.6%) |
|  | Moderate | 0 (0.0%) | 0 (0.0%) | 0 (0.0%) | 1 (12.5%) | 1 (3.1%) |
|  | Severe | 0 (0.0%) | 0 (0.0%) | 0 (0.0%) | 1 (12.5%) | 1 (3.1%) |
| NEUTROPENIA | Mild | 0 (0.0%) | 0 (0.0%) | 0 (0.0%) | 2 (25.0%) | 2 (6.3%) |
|  | Moderate | 0 (0.0%) | 0 (0.0%) | 1 (12.5%) | 3 (37.5%) | 4 (12.5%) |
|  | Severe | 0 (0.0%) | 1 (12.5%) | 0 (0.0%) | 1 (12.5%) | 2 (6.3%) |
| THROMBOCYTOPENIA | Mild | 1 (12.5%) | 0 (0.0%) | 0 (0.0%) | 1 (12.5%) | 2 (6.3%) |
|  | Moderate | 0 (0.0%) | 1 (12.5%) | 1 (12.5%) | 0 (0.0%) | 2 (6.3%) |
|  | Severe | 0 (0.0%) | 0 (0.0%) | 0 (0.0%) | 0 (0.0%) | 0 (0.0%) |
| CARDIAC DISORDERS | | | | | | |
| ANGINA PECTORIS | Mild | 0 (0.0%) | 0 (0.0%) | 0 (0.0%) | 1 (12.5%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| ENDOCRINE DISORDERS | | | | | | |
| AUTOIMMUNE THYROIDITIS | Mild | 0 (0.0%) | 0 (0.0%) | 0 (0.0%) | 0 (0.0%) | 0 (0.0%) |
|  | Moderate | 0 (0.0%) | 0 (0.0%) | 0 (0.0%) | 1 (12.5%) | 1 (3.1%) |
|  | Severe | 0 (0.0%) | 0 (0.0%) | 0 (0.0%) | 0 (0.0%) | 0 (0.0%) |
| THYROID PAIN | Mild | 0 (0.0%) | 0 (0.0%) | 0 (0.0%) | 1 (12.5%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| EYE DISORDERS | | | | | | |
| BLEPHARITIS | Mild | 0 (0.0%) | 0 (0.0%) | 1 (12.5%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| EYE PAIN | Mild | 1 (12.5%) | 0 (0.0%) | 0 (0.0%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| SCLERAL DISORDER | Mild | 1 (12.5%) | 1 (12.5%) | 0 (0.0%) | 0 (0.0%) | 2 (6.3%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| GASTROINTESTINAL DISORDERS | | | | | | |
| ABDOMINAL DISCOMFORT | Mild | 0 (0.0%) | 0 (0.0%) | 1 (12.5%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| ABDOMINAL PAIN LOWER | Mild | 1 (12.5%) | 0 (0.0%) | 0 (0.0%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| DIARRHOEA | Mild | 0 (0.0%) | 0 (0.0%) | 0 (0.0%) | 0 (0.0%) | 0 (0.0%) |
|  | Moderate | 1 (12.5%) | 0 (0.0%) | 0 (0.0%) | 0 (0.0%) | 1 (3.1%) |
|  | Severe | 0 (0.0%) | 0 (0.0%) | 0 (0.0%) | 0 (0.0%) | 0 (0.0%) |
| DRY MOUTH | Mild | 2 (25.0%) | 1 (12.5%) | 2 (25.0%) | 0 (0.0%) | 5 (15.6%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| DUODENAL ULCER | Mild | 0 (0.0%) | 0 (0.0%) | 0 (0.0%) | 0 (0.0%) | 0 (0.0%) |
|  | Moderate | 0 (0.0%) | 0 (0.0%) | 1 (12.5%) | 0 (0.0%) | 1 (3.1%) |
|  | Severe | 0 (0.0%) | 0 (0.0%) | 0 (0.0%) | 0 (0.0%) | 0 (0.0%) |
| DYSPEPSIA | Mild | 1 (12.5%) | 0 (0.0%) | 0 (0.0%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| GASTRITIS | Mild | 0 (0.0%) | 0 (0.0%) | 0 (0.0%) | 2 (25.0%) | 2 (6.3%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| GINGIVAL BLEEDING | Mild | 0 (0.0%) | 0 (0.0%) | 0 (0.0%) | 1 (12.5%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |

TABLE 15-continued

SUMMARY OF RELATED TREATMENT EMERGENT ADVERSE EVENTS
BY SYSTEM ORGAN CLASS, MedDRA PREFERRED TERM, SEVERITY AND DOSE GROUP
(SAFETY POPULATION)

| System Organ Class Preferred term | Severity | Locteron 160 ug N = 8 n (%) | Locteron 320 ug N = 8 n (%) | Locteron 480 ug N = 8 n (%) | Locteron 640 ug N = 8 n (%) | Total N = 32 n (%) |
|---|---|---|---|---|---|---|
| NAUSEA | Mild | 1 (12.5%) | 0 (0.0%) | 1 (12.5%) | 2 (25.0%) | 4 (12.5%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| STOMATITIS | Mild | 0 (0.0%) | 0 (0.0%) | 0 (0.0%) | 2 (25.0%) | 2 (6.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| VOMITING | Mild | 1 (12.5%) | 0 (0.0%) | 0 (0.0%) | 0 (0.0%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| GENERAL DISORDERS AND ADMINISTRATION SITE CONDITIONS | | | | | | |
| ASTHENIA | Mild | 3 (37.5%) | 4 (50.0%) | 3 (37.5%) | 6 (75.0%) | 16 (50.0%) |
| | Moderate | 1 (12.5%) | 0 (0.0%) | 1 (12.5%) | 1 (12.5%) | 3 (9.4%) |
| | Severe | 0 (0.0%) | 0 (0.0%) | 0 (0.0%) | 0 (0.0%) | 0 (0.0%) |
| CHILLS | Mild | 0 (0.0%) | 0 (0.0%) | 0 (0.0%) | 0 (0.0%) | 0 (0.0%) |
| | Moderate | 0 (0.0%) | 1 (12.5%) | 0 (0.0%) | 0 (0.0%) | 1 (3.1%) |
| | Severe | 0 (0.0%) | 0 (0.0%) | 0 (0.0%) | 0 (0.0%) | 0 (0.0%) |
| FATIGUE | Mild | 1 (12.5%) | 0 (0.0%) | 0 (0.0%) | 0 (0.0%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| IRRITABILITY | Mild | 1 (12.5%) | 1 (12.5%) | 1 (12.5%) | 3 (37.5%) | 6 (18.8%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| PYREXIA | Mild | 1 (12.5%) | 1 (12.5%) | 0 (0.0%) | 4 (50.0%) | 6 (18.8%) |
| | Moderate | 0 (0.0%) | 0 (0.0%) | 0 (0.0%) | 0 (0.0%) | 0 (0.0%) |
| | Severe | 0 (0.0%) | 1 (12.5%) | 0 (0.0%) | 0 (0.0%) | 1 (3.1%) |
| INFECTIONS AND INFESTATIONS | | | | | | |
| BRONCHITIS | Mild | 0 (0.0%) | 0 (0.0%) | 0 (0.0%) | 1 (12.5%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| EAR INFECTION | Mild | 0 (0.0%) | 0 (0.0%) | 0 (0.0%) | 0 (0.0%) | 0 (0.0%) |
| | Moderate | 0 (0.0%) | 0 (0.0%) | 0 (0.0%) | 1 (12.5%) | 1 (3.1%) |
| | Severe | 0 (0.0%) | 0 (0.0%) | 0 (0.0%) | 0 (0.0%) | 0 (0.0%) |
| HERPES SIMPLEX | Mild | 0 (0.0%) | 0 (0.0%) | 0 (0.0%) | 1 (12.5%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| INVESTIGATIONS | | | | | | |
| BILIRUBIN CONJUGATED INCREASED | Mild | 1 (12.5%) | 1 (12.5%) | 1 (12.5%) | 0 (0.0%) | 3 (9.4%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| BLOOD BILIRUBIN INCREASED | Mild | 1 (12.5%) | 1 (12.5%) | 0 (0.0%) | 0 (0.0%) | 2 (6.3%) |
| | Moderate | 0 (0.0%) | 1 (12.5%) | 0 (0.0%) | 0 (0.0%) | 1 (3.1%) |
| | Severe | 0 (0.0%) | 0 (0.0%) | 0 (0.0%) | 0 (0.0%) | 0 (0.0%) |
| BLOOD THYROID STIMULATING HORMONE DECREASED | Mild | 0 (0.0%) | 0 (0.0%) | 0 (0.0%) | 0 (0.0%) | 0 (0.0%) |
| | Moderate | 0 (0.0%) | 0 (0.0%) | 0 (0.0%) | 1 (12.5%) | 1 (3.1%) |
| | Severe | 0 (0.0%) | 0 (0.0%) | 0 (0.0%) | 0 (0.0%) | 0 (0.0%) |
| HAEMOGLOBIN DECREASED | Mild | 1 (12.5%) | 1 (12.5%) | 0 (0.0%) | 2 (25.0%) | 4 (12.5%) |
| | Moderate | 0 (0.0%) | 0 (0.0%) | 1 (12.5%) | 0 (0.0%) | 1 (3.1%) |
| | Severe | 0 (0.0%) | 0 (0.0%) | 0 (0.0%) | 0 (0.0%) | 0 (0.0%) |
| LYMPHOCYTE COUNT DECREASED | Mild | 1 (12.5%) | 0 (0.0%) | 1 (12.5%) | 1 (12.5%) | 3 (9.4%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| NEUTROPHIL COUNT DECREASED | Mild | 2 (25.0%) | 1 (12.5%) | 1 (12.5%) | 2 (25.0%) | 6 (18.8%) |
| | Moderate | 0 (0.0%) | 1 (12.5%) | 1 (12.5%) | 0 (0.0%) | 2 (6.3%) |
| | Severe | 0 (0.0%) | 0 (0.0%) | 0 (0.0%) | 0 (0.0%) | 0 (0.0%) |
| PLATELET COUNT DECREASED | Mild | 1 (12.5%) | 0 (0.0%) | 0 (0.0%) | 1 (12.5%) | 2 (6.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| RED BLOOD CELL COUNT DECREASED | Mild | 2 (25.0%) | 1 (12.5%) | 1 (12.5%) | 2 (25.0%) | 6 (18.8%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| WEIGHT DECREASED | Mild | 0 (0.0%) | 0 (0.0%) | 0 (0.0%) | 1 (12.5%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| WHITE BLOOD CELL COUNT DECREASED | Mild | 1 (12.5%) | 1 (12.5%) | 2 (25.0%) | 2 (25.0%) | 6 (18.8%) |
| | Moderate | 1 (12.5%) | 0 (0.0%) | 0 (0.0%) | 0 (0.0%) | 1 (3.1%) |
| | Severe | 0 (0.0%) | 0 (0.0%) | 0 (0.0%) | 0 (0.0%) | 0 (0.0%) |

TABLE 15-continued

SUMMARY OF RELATED TREATMENT EMERGENT ADVERSE EVENTS
BY SYSTEM ORGAN CLASS, MedDRA PREFERRED TERM, SEVERITY AND DOSE GROUP
(SAFETY POPULATION)

| System Organ Class Preferred term | Severity | Locteron 160 ug N = 8 n (%) | Locteron 320 ug N = 8 n (%) | Locteron 480 ug N = 8 n (%) | Locteron 640 ug N = 8 n (%) | Total N = 32 n (%) |
|---|---|---|---|---|---|---|
| METABOLISM AND NUTRITION DISORDERS | | | | | | |
| DECREASED APPETITE | Mild | 3 (37.5%) | 2 (25.0%) | 2 (25.0%) | 5 (62.5%) | 12 (37.5%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| MUSCULOSKELETAL AND CONNECTIVE TISSUE DISORDERS | | | | | | |
| ARTHRALGIA | Mild | 1 (12.5%) | 3 (37.5%) | 5 (62.5%) | 3 (37.5%) | 12 (37.5%) |
| | Moderate | 1 (12.5%) | 1 (12.5%) | 1 (12.5%) | 1 (12.5%) | 4 (12.5%) |
| | Severe | 0 (0.0%) | 0 (0.0%) | 0 (0.0%) | 0 (0.0%) | 0 (0.0%) |
| BONE PAIN | Mild | 0 (0.0%) | 0 (0.0%) | 1 (12.5%) | 0 (0.0%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| MYALGIA | Mild | 3 (37.5%) | 4 (50.0%) | 2 (25.0%) | 4 (50.0%) | 13 (40.6%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| NERVOUS SYSTEM DISORDERS | | | | | | |
| DIZZINESS | Mild | 1 (12.5%) | 0 (0.0%) | 0 (0.0%) | 0 (0.0%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| DYSGEUSIA | Mild | 0 (0.0%) | 0 (0.0%) | 1 (12.5%) | 0 (0.0%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| HEADACHE | Mild | 4 (50.0%) | 2 (25.0%) | 2 (25.0%) | 4 (50.0%) | 12 (37.5%) |
| | Moderate | 0 (0.0%) | 0 (0.0%) | 0 (0.0%) | 1 (12.5%) | 1 (3.1%) |
| | Severe | 0 (0.0%) | 0 (0.0%) | 0 (0.0%) | 0 (0.0%) | 0 (0.0%) |
| SOMNOLENCE | Mild | 0 (0.0%) | 1 (12.5%) | 1 (12.5%) | 1 (12.5%) | 3 (9.4%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| PSYCHIATRIC DISORDERS | | | | | | |
| DEPRESSION | Mild | 1 (12.5%) | 0 (0.0%) | 0 (0.0%) | 3 (37.5%) | 4 (12.5%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| DYSSOMNIA | Mild | 1 (12.5%) | 2 (25.0%) | 3 (37.5%) | 3 (37.5%) | 9 (28.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| INSOMNIA | Mild | 0 (0.0%) | 0 (0.0%) | 1 (12.5%) | 0 (0.0%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| RESPIRATORY, THORACIC AND MEDIASTINAL DISORDERS | | | | | | |
| COUGH | Mild | 1 (12.5%) | 0 (0.0%) | 3 (37.5%) | 2 (25.0%) | 6 (18.8%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| EPISTAXIS | Mild | 0 (0.0%) | 0 (0.0%) | 0 (0.0%) | 0 (0.0%) | 0 (0.0%) |
| | Moderate | 0 (0.0%) | 0 (0.0%) | 1 (12.5%) | 0 (0.0%) | 1 (3.1%) |
| | Severe | 0 (0.0%) | 0 (0.0%) | 0 (0.0%) | 0 (0.0%) | 0 (0.0%) |
| RHINORRHOEA | Mild | 0 (0.0%) | 0 (0.0%) | 1 (12.5%) | 0 (0.0%) | 1 (3.1%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| SKIN AND SUBCUTANEOUS TISSUE DISORDERS | | | | | | |
| ALOPECIA | Mild | 2 (25.0%) | 0 (0.0%) | 1 (12.5%) | 1 (12.5%) | 4 (12.5%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| DRY SKIN | Mild | 4 (50.0%) | 3 (37.5%) | 4 (50.0%) | 1 (12.5%) | 12 (37.5%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| JAUNDICE | Mild | 0 (0.0%) | 0 (0.0%) | 0 (0.0%) | 0 (0.0%) | 0 (0.0%) |
| | Moderate | 0 (0.0%) | 1 (12.5%) | 0 (0.0%) | 0 (0.0%) | 1 (3.1%) |
| | Severe | 0 (0.0%) | 0 (0.0%) | 0 (0.0%) | 0 (0.0%) | 0 (0.0%) |
| PRURITUS | Mild | 2 (25.0%) | 0 (0.0%) | 1 (12.5%) | 0 (0.0%) | 3 (9.4%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| RASH MACULAR | Mild | 0 (0.0%) | 0 (0.0%) | 0 (0.0%) | 0 (0.0%) | 0 (0.0%) |
| | Moderate | 0 (0.0%) | 0 (0.0%) | 0 (0.0%) | 1 (12.5%) | 1 (3.1%) |
| | Severe | 0 (0.0%) | 0 (0.0%) | 0 (0.0%) | 0 (0.0%) | 0 (0.0%) |

TABLE 15-continued

SUMMARY OF RELATED TREATMENT EMERGENT ADVERSE EVENTS
BY SYSTEM ORGAN CLASS, MedDRA PREFERRED TERM, SEVERITY AND DOSE GROUP
(SAFETY POPULATION)

| System Organ Class Preferred term | Severity | Locteron 160 ug N = 8 n (%) | Locteron 320 ug N = 8 n (%) | Locteron 480 ug N = 8 n (%) | Locteron 640 ug N = 8 n (%) | Total N = 32 n (%) |
|---|---|---|---|---|---|---|
| RASH PRURITIC | Mild | 0 (0.0%) | 0 (0.0%) | 0 (0.0%) | 1 (12.5%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| SKIN EXFOLIATION | Mild | 0 (0.0%) | 0 (0.0%) | 1 (12.5%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| SKIN FISSURES | Mild | 1 (12.5%) | 0 (0.0%) | 0 (0.0%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| URTICARIA | Mild | 0 (0.0%) | 0 (0.0%) | 1 (12.5%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| VASCULAR DISORDERS | | | | | | |
| ANGIOPATHY | Mild | 0 (0.0%) | 0 (0.0%) | 1 (12.5%) | 0 (0.0%) | 1 (3.1%) |
|  | Moderate | 0 (0.0%) | 0 (0.0%) | 0 (0.0%) | 0 (0.0%) | 0 (0.0%) |
|  | Severe | 0 (0.0%) | 0 (0.0%) | 0 (0.0%) | 0 (0.0%) | 0 (0.0%) |
| HYPERAEMIA | Mild | 2 (25.0%) | 1 (12.5%) | 1 (12.5%) | 0 (0.0%) | 4 (12.5%) |
|  | Moderate | 0 (0.0%) | 0 (0.0%) | 0 (0.0%) | 1 (12.5%) | 1 (3.1%) |
|  | Severe | 0 (0.0%) | 0 (0.0%) | 0 (0.0%) | 0 (0.0%) | 0 (0.0%) |

Footnote 1:
A subject with multiple occurrences of an AE under one dose group is counted only once in the AE preferred term for that dose group.
Footnote 2:
A subject with multiple adverse events within a primary system organ class is counted only once in the total row.
Footnote 3:
Related AE corresponds to AE were causality has been assigned as possible or probable.

A total of 10 patients (31.3%) experienced mild AEs and 18 patients (56.3%) experienced moderate AEs considered related to study medication. In total, 3 patients (9.4%) experienced severe AEs, all of which were suspected to be related to the study medication.

The 3 patients who experienced AEs that were considered to be severe and related to the study medication were as follows:

Patient 01/14 (320 μg treatment group) experienced severe neutropenia suspected to be probably related to study medication.

Patient 01/02 (640 μg treatment group) experienced severe neutropenia and leukopenia, which were both suspected to be probably related to study medication.

Patient 02/15 (320 μg treatment group) experienced the influenza symptom of severe pyrexia, which was suspected to be probably related to the study medication.

All patients recovered from these occurrences of severe AEs. Patient 01/02 was later withdrawn from the study due to AEs of moderate autoimmune thyroiditis, mild neutropenia and mild leukopenia.

Influenza-Like Symptoms

Influenza-like symptoms were defined as headache, myalgias, pyrexia, nausea and asthenia. All AEs of influenza like symptoms are presented by preferred term, severity (mild, moderate, or severe) and duration. A summary of treatment emergent AEs is presented in Table 16 and a summary of all influenza like symptoms by duration is summarized in Table 17.

TABLE 16

SUMMARY OF TREATMENT EMERGENT ADVERSE EVENTS
BY SYSTEM ORGAN CLASS, MedDRA PREFERRED TERM AND DOSE GROUP
(SAFETY POPULATION)

| System Organ Class Preferred term | Locteron 160 ug N = 8 n (%) | Locteron 320 ug N = 8 n (%) | Locteron 480 ug N = 8 n (%) | Locteron 640 ug N = 8 n (%) | Total N = 32 n (%) |
|---|---|---|---|---|---|
| Any System Organ Class | 7 (87.5%) | 8 (100.0%) | 8 (100.0%) | 8 (100.0%) | 31 (96.9%) |
| BLOOD AND LYMPHATIC SYSTEM DISORDERS | 1 (12.5%) | 3 (37.5%) | 3 (37.5%) | 6 (75.0%) | 13 (40.6%) |
| NEUTROPENIA | 0 (0.0%) | 1 (12.5%) | 1 (12.5%) | 6 (75.0%) | 8 (25.0%) |
| LEUKOPENIA | 0 (0.0%) | 2 (25.0%) | 1 (12.5%) | 4 (50.0%) | 7 (21.9%) |
| THROMBOCYTOPENIA | 1 (12.5%) | 1 (12.5%) | 1 (12.5%) | 1 (12.5%) | 4 (12.5%) |
| CARDIAC DISORDERS | 0 (0.0%) | 0 (0.0%) | 0 (0.0%) | 1 (12.5%) | 1 (3.1%) |
| ANGINA PECTORIS | 0 (0.0%) | 0 (0.0%) | 0 (0.0%) | 1 (12.5%) | 1 (3.1%) |
| ENDOCRINE DISORDERS | 0 (0.0%) | 0 (0.0%) | 0 (0.0%) | 1 (12.5%) | 1 (3.1%) |
| AUTOIMMUNE THYROIDITIS | 0 (0.0%) | 0 (0.0%) | 0 (0.0%) | 1 (12.5%) | 1 (3.1%) |
| THYROID PAIN | 0 (0.0%) | 0 (0.0%) | 0 (0.0%) | 1 (12.5%) | 1 (3.1%) |

TABLE 16-continued

SUMMARY OF TREATMENT EMERGENT ADVERSE EVENTS
BY SYSTEM ORGAN CLASS, MedDRA PREFERRED TERM AND DOSE GROUP
(SAFETY POPULATION)

| System Organ Class<br>Preferred term | Locteron<br>160 ug<br>N = 8<br>n (%) | Locteron<br>320 ug<br>N = 8<br>n (%) | Locteron<br>480 ug<br>N = 8<br>n (%) | Locteron<br>640 ug<br>N = 8<br>n (%) | Total<br>N = 32<br>n (%) |
|---|---|---|---|---|---|
| EYE DISORDERS | 2 (25.0%) | 1 (12.5%) | 1 (12.5%) | 0 (0.0%) | 4 (12.5%) |
| SCLERAL DISORDER | 1 (12.5%) | 1 (12.5%) | 0 (0.0%) | 0 (0.0%) | 2 (6.3%) |
| BLEPHARITIS | 0 (0.0%) | 0 (0.0%) | 1 (12.5%) | 0 (0.0%) | 1 (3.1%) |
| EYE PAIN | 1 (12.5%) | 0 (0.0%) | 0 (0.0%) | 0 (0.0%) | 1 (3.1%) |
| GASTROINTESTINAL DISORDERS | 4 (50.0%) | 1 (12.5%) | 3 (37.5%) | 5 (62.5%) | 13 (40.6%) |
| DRY MOUTH | 2 (25.0%) | 1 (12.5%) | 2 (25.0%) | 0 (0.0%) | 5 (15.6%) |
| NAUSEA | 1 (12.5%) | 0 (0.0%) | 1 (12.5%) | 2 (25.0%) | 4 (12.5%) |
| DIARRHOEA | 1 (12.5%) | 0 (0.0%) | 0 (0.0%) | 1 (12.5%) | 2 (6.3%) |
| GASTRITIS | 0 (0.0%) | 0 (0.0%) | 0 (0.0%) | 2 (25.0%) | 2 (6.3%) |
| STOMATITIS | 0 (0.0%) | 0 (0.0%) | 0 (0.0%) | 2 (25.0%) | 2 (6.3%) |
| ABDOMINAL DISCOMFORT | 0 (0.0%) | 0 (0.0%) | 1 (12.5%) | 0 (0.0%) | 1 (3.1%) |
| ABDOMINAL PAIN LOWER | 1 (12.5%) | 0 (0.0%) | 0 (0.0%) | 0 (0.0%) | 1 (3.1%) |
| DUODENAL ULCER | 0 (0.0%) | 0 (0.0%) | 1 (12.5%) | 0 (0.0%) | 1 (3.1%) |
| DYSPEPSIA | 1 (12.5%) | 0 (0.0%) | 0 (0.0%) | 0 (0.0%) | 1 (3.1%) |
| GINGIVAL BLEEDING | 0 (0.0%) | 0 (0.0%) | 0 (0.0%) | 1 (12.5%) | 1 (3.1%) |
| VOMITING | 1 (12.5%) | 0 (0.0%) | 0 (0.0%) | 0 (0.0%) | 1 (3.1%) |
| GENERAL DISORDERS AND ADMINISTRATION SITE CONDITIONS | 5 (62.5%) | 5 (62.5%) | 4 (50.0%) | 7 (87.5%) | 21 (65.6%) |
| ASTHENIA | 4 (50.0%) | 4 (50.0%) | 4 (50.0%) | 7 (87.5%) | 19 (59.4%) |
| PYREXIA | 1 (12.5%) | 2 (25.0%) | 0 (0.0%) | 4 (50.0%) | 7 (21.9%) |
| IRRITABILITY | 1 (12.5%) | 1 (12.5%) | 1 (12.5%) | 3 (37.5%) | 6 (18.8%) |
| CHILLS | 0 (0.0%) | 1 (12.5%) | 0 (0.0%) | 0 (0.0%) | 1 (3.1%) |
| FATIGUE | 1 (12.5%) | 0 (0.0%) | 0 (0.0%) | 0 (0.0%) | 1 (3.1%) |
| MUCOSA VESICLE | 1 (12.5%) | 0 (0.0%) | 0 (0.0%) | 0 (0.0%) | 1 (3.1%) |
| INFECTIONS AND INFESTATIONS | 1 (12.5%) | 0 (0.0%) | 0 (0.0%) | 3 (37.5%) | 4 (12.5%) |
| HERPES SIMPLEX | 1 (12.5%) | 0 (0.0%) | 0 (0.0%) | 1 (12.5%) | 2 (6.3%) |
| BRONCHITIS | 0 (0.0%) | 0 (0.0%) | 0 (0.0%) | 1 (12.5%) | 1 (3.1%) |
| EAR INFECTION | 0 (0.0%) | 0 (0.0%) | 0 (0.0%) | 1 (12.5%) | 1 (3.1%) |
| INVESTIGATIONS | 3 (37.5%) | 3 (37.5%) | 3 (37.5%) | 4 (50.0%) | 13 (40.6%) |
| NEUTROPHIL COUNT DECREASED | 2 (25.0%) | 2 (25.0%) | 2 (25.0%) | 2 (25.0%) | 8 (25.0%) |
| WHITE BLOOD CELL COUNT DECREASED | 2 (25.0%) | 1 (12.5%) | 2 (25.0%) | 2 (25.0%) | 7 (21.9%) |
| RED BLOOD CELL COUNT DECREASED | 2 (25.0%) | 1 (12.5%) | 1 (12.5%) | 2 (25.0%) | 6 (18.8%) |
| HAEMOGLOBIN DECREASED | 1 (12.5%) | 1 (12.5%) | 1 (12.5%) | 2 (25.0%) | 5 (15.6%) |
| BILIRUBIN CONJUGATED INCREASED | 1 (12.5%) | 1 (12.5%) | 2 (25.0%) | 0 (0.0%) | 4 (12.5%) |
| BLOOD BILIRUBIN INCREASED | 1 (12.5%) | 2 (25.0%) | 0 (0.0%) | 0 (0.0%) | 3 (9.4%) |
| LYMPHOCYTE COUNT DECREASED | 1 (12.5%) | 0 (0.0%) | 1 (12.5%) | 1 (12.5%) | 3 (9.4%) |
| PLATELET COUNT DECREASED | 1 (12.5%) | 0 (0.0%) | 0 (0.0%) | 1 (12.5%) | 2 (6.3%) |
| BLOOD GLUCOSE INCREASED | 0 (0.0%) | 0 (0.0%) | 1 (12.5%) | 0 (0.0%) | 1 (3.1%) |
| BLOOD THYROID STIMULATING HORMONE DECREASED | 0 (0.0%) | 0 (0.0%) | 0 (0.0%) | 1 (12.5%) | 1 (3.1%) |
| BLOOD UREA DECREASED | 1 (12.5%) | 0 (0.0%) | 0 (0.0%) | 0 (0.0%) | 1 (3.1%) |
| HAEMATOCRIT DECREASED | 0 (0.0%) | 1 (12.5%) | 0 (0.0%) | 0 (0.0%) | 1 (3.1%) |
| WEIGHT DECREASED | 0 (0.0%) | 0 (0.0%) | 0 (0.0%) | 1 (12.5%) | 1 (3.1%) |
| METABOLISM AND NUTRITION DISORDERS | 3 (37.5%) | 2 (25.0%) | 3 (37.5%) | 5 (62.5%) | 13 (40.6%) |
| DECREASED APPETITE | 3 (37.5%) | 2 (25.0%) | 3 (37.5%) | 5 (62.5%) | 13 (40.6%) |
| MUSCULOSKELETAL AND CONNECTIVE TISSUE DISORDERS | 4 (50.0%) | 7 (87.5%) | 7 (87.5%) | 5 (62.5%) | 23 (71.9%) |
| ARTHRALGIA | 2 (25.0%) | 4 (50.0%) | 6 (75.0%) | 4 (50.0%) | 16 (50.0%) |
| MYALGIA | 3 (37.5%) | 4 (50.0%) | 2 (25.0%) | 4 (50.0%) | 13 (40.6%) |
| BACK PAIN | 0 (0.0%) | 1 (12.5%) | 0 (0.0%) | 0 (0.0%) | 1 (3.1%) |
| BONE PAIN | 0 (0.0%) | 0 (0.0%) | 1 (12.5%) | 0 (0.0%) | 1 (3.1%) |
| NERVOUS SYSTEM DISORDERS | 4 (50.0%) | 3 (37.5%) | 4 (50.0%) | 5 (62.5%) | 16 (50.0%) |
| HEADACHE | 4 (50.0%) | 3 (37.5%) | 2 (25.0%) | 5 (62.5%) | 14 (43.8%) |
| SOMNOLENCE | 0 (0.0%) | 1 (12.5%) | 1 (12.5%) | 1 (12.5%) | 3 (9.4%) |
| CLUSTER HEADACHE | 0 (0.0%) | 0 (0.0%) | 1 (12.5%) | 0 (0.0%) | 1 (3.1%) |
| DIZZINESS | 1 (12.5%) | 0 (0.0%) | 0 (0.0%) | 0 (0.0%) | 1 (3.1%) |
| DYSGEUSIA | 0 (0.0%) | 0 (0.0%) | 1 (12.5%) | 0 (0.0%) | 1 (3.1%) |
| RADICULITIS LUMBOSACRAL | 0 (0.0%) | 1 (12.5%) | 0 (0.0%) | 0 (0.0%) | 1 (3.1%) |
| VASCULAR HEADACHE | 0 (0.0%) | 0 (0.0%) | 1 (12.5%) | 0 (0.0%) | 1 (3.1%) |
| PSYCHIATRIC DISORDERS | 2 (25.0%) | 2 (25.0%) | 4 (50.0%) | 4 (50.0%) | 12 (37.5%) |
| DYSSOMNIA | 1 (12.5%) | 2 (25.0%) | 3 (37.5%) | 3 (37.5%) | 9 (28.1%) |
| DEPRESSION | 1 (12.5%) | 0 (0.0%) | 0 (0.0%) | 3 (37.5%) | 4 (12.5%) |
| INSOMNIA | 0 (0.0%) | 0 (0.0%) | 1 (12.5%) | 1 (12.5%) | 2 (6.3%) |
| RESPIRATORY, THORACIC AND MEDIASTINAL DISORDERS | 1 (12.5%) | 0 (0.0%) | 3 (37.5%) | 2 (25.0%) | 6 (18.8%) |
| COUGH | 1 (12.5%) | 0 (0.0%) | 3 (37.5%) | 2 (25.0%) | 6 (18.8%) |
| EPISTAXIS | 0 (0.0%) | 0 (0.0%) | 1 (12.5%) | 0 (0.0%) | 1 (3.1%) |
| RHINORRHOEA | 0 (0.0%) | 0 (0.0%) | 1 (12.5%) | 0 (0.0%) | 1 (3.1%) |
| SKIN AND SUBCUTANEOUS TISSUE DISORDERS | 5 (62.5%) | 4 (50.0%) | 4 (50.0%) | 3 (37.5%) | 16 (50.0%) |

TABLE 16-continued

SUMMARY OF TREATMENT EMERGENT ADVERSE EVENTS
BY SYSTEM ORGAN CLASS, MedDRA PREFERRED TERM AND DOSE GROUP
(SAFETY POPULATION)

| System Organ Class<br>Preferred term | Locteron<br>160 ug<br>N = 8<br>n (%) | Locteron<br>320 ug<br>N = 8<br>n (%) | Locteron<br>480 ug<br>N = 8<br>n (%) | Locteron<br>640 ug<br>N = 8<br>n (%) | Total<br>N = 32<br>n (%) |
|---|---|---|---|---|---|
| DRY SKIN | 4 (50.0%) | 3 (37.5%) | 4 (50.0%) | 1 (12.5%) | 12 (37.5%) |
| ALOPECIA | 2 (25.0%) | 0 (0.0%) | 1 (12.5%) | 1 (12.5%) | 4 (12.5%) |
| PRURITUS | 2 (25.0%) | 0 (0.0%) | 1 (12.5%) | 0 (0.0%) | 3 (9.4%) |
| RASH | 1 (12.5%) | 0 (0.0%) | 1 (12.5%) | 0 (0.0%) | 2 (6.3%) |
| URTICARIA | 0 (0.0%) | 0 (0.0%) | 1 (12.5%) | 1 (12.5%) | 2 (6.3%) |
| DERMATITIS ALLERGIC | 0 (0.0%) | 1 (12.5%) | 0 (0.0%) | 0 (0.0%) | 1 (3.1%) |
| HYPERHIDROSIS | 0 (0.0%) | 0 (0.0%) | 0 (0.0%) | 1 (12.5%) | 1 (3.1%) |
| JAUNDICE | 0 (0.0%) | 1 (12.5%) | 0 (0.0%) | 0 (0.0%) | 1 (3.1%) |
| RASH MACULAR | 0 (0.0%) | 0 (0.0%) | 0 (0.0%) | 1 (12.5%) | 1 (3.1%) |
| RASH PRURITIC | 0 (0.0%) | 0 (0.0%) | 0 (0.0%) | 1 (12.5%) | 1 (3.1%) |
| SKIN EXFOLIATION | 0 (0.0%) | 0 (0.0%) | 1 (12.5%) | 0 (0.0%) | 1 (3.1%) |
| SKIN FISSURES | 1 (12.5%) | 0 (0.0%) | 0 (0.0%) | 0 (0.0%) | 1 (3.1%) |
| VASCULAR DISORDERS | 2 (25.0%) | 1 (12.5%) | 2 (25.0%) | 1 (12.5%) | 6 (18.8%) |
| HYPERAEMIA | 2 (25.0%) | 1 (12.5%) | 1 (12.5%) | 1 (12.5%) | 5 (15.6%) |
| ANGIOPATHY | 0 (0.0%) | 0 (0.0%) | 1 (12.5%) | 0 (0.0%) | 1 (3.1%) |

Footnote 1:
A subject with multiple occurrences of an AE under one dose group is counted only once in the AE preferred term for that dose group.
Footnote 2:
A subject with multiple adverse events within a primary system organ class is counted only once in the total row.

TABLE 17

SUMMARY OF DURATION OF TREATMENT EMERGENT FLU SYMPTOMS
BY DOSE GROUP
(SAFETY POPULATION)

| | | Statistics | Locteron<br>160 ug<br>N = 8 | Locteron<br>320 ug<br>N = 8 | Locteron<br>480 ug<br>N = 8 | Locteron<br>640 ug<br>N = 8 | Total<br>N = 32 |
|---|---|---|---|---|---|---|---|
| WEEK 12/DAY 78 | WEAKNESS | N | | | | 1 | 1 |
| | | Mean | | | | 29.000 | 29.000 |
| | | Median | | | | 29.000 | 29.000 |
| | | SD | | | | | |
| | | Minimum | | | | 29.00 | 29.00 |
| | | Maximum | | | | 29.00 | 29.00 |
| | | Missing | | | | 0 | 0 |
| BASELINE/DAY 1 | HEADACHE | N | 1 | 1 | 2 | 2 | 6 |
| | | Mean | 0.167 | 0.125 | 3.063 | 11.833 | 5.014 |
| | | Median | 0.167 | 0.125 | 3.063 | 11.833 | 3.063 |
| | | SD | | | 3.6239 | 1.4731 | 5.7153 |
| | | Minimum | 0.17 | 0.13 | 0.50 | 10.79 | 0.13 |
| | | Maximum | 0.17 | 0.13 | 5.63 | 12.88 | 12.88 |
| | | Missing | 0 | 0 | 0 | 1 | 1 |
| | MYALGIAS | N | | | 2 | 2 | 4 |
| | | Mean | | | 0.688 | 47.063 | 23.875 |
| | | Median | | | 0.688 | 47.063 | 5.750 |
| | | SD | | | 0.2652 | 51.5304 | 40.0254 |
| | | Minimum | | | 0.50 | 10.63 | 0.50 |
| | | Maximum | | | 0.88 | 83.50 | 83.50 |
| | | Missing | | | 0 | 0 | 0 |
| | FEVER | N | | 1 | | 1 | 2 |
| | | Mean | | 0.250 | | 0.333 | 0.292 |
| | | Median | | 0.250 | | 0.333 | 0.292 |
| | | SD | | | | | 0.0589 |
| | | Minimum | | 0.25 | | 0.33 | 0.25 |
| | | Maximum | | 0.25 | | 0.33 | 0.33 |
| | | Missing | | 0 | | 0 | 0 |
| | WEAKNESS | N | 1 | | 0 | 0 | 1 |
| | | Mean | 10.208 | | | | 10.208 |
| | | Median | 10.208 | | | | 10.208 |
| | | SD | | | | | |
| | | Minimum | 10.21 | | | | 10.21 |
| | | Maximum | 10.21 | | | | 10.21 |
| | | Missing | 0 | | 1 | 1 | 2 |

TABLE 17-continued

SUMMARY OF DURATION OF TREATMENT EMERGENT FLU SYMPTOMS
BY DOSE GROUP
(SAFETY POPULATION)

|  |  | Statistics | Locteron 160 ug N = 8 | Locteron 320 ug N = 8 | Locteron 480 ug N = 8 | Locteron 640 ug N = 8 | Total N = 32 |
|---|---|---|---|---|---|---|---|
| WEEK 1/DAY 2 | HEADACHE | N |  |  | 1 |  | 1 |
|  |  | Mean |  |  | 5.625 |  | 5.625 |
|  |  | Median |  |  | 5.625 |  | 5.625 |
|  |  | SD |  |  |  |  |  |
|  |  | Minimum |  |  | 5.63 |  | 5.63 |
|  |  | Maximum |  |  | 5.63 |  | 5.63 |
|  |  | Missing |  |  | 1 |  | 1 |
|  | MYALGIAS | N | 1 |  | 0 | 1 | 2 |
|  |  | Mean | 1.000 |  |  | 0.333 | 0.667 |
|  |  | Median | 1.000 |  |  | 0.333 | 0.667 |
|  |  | SD |  |  |  |  | 0.4714 |
|  |  | Minimum | 1.00 |  |  | 0.33 | 0.33 |
|  |  | Maximum | 1.00 |  |  | 0.33 | 1.00 |
|  |  | Missing | 0 |  | 1 | 1 | 2 |
|  | FEVER | N |  |  |  | 2 | 2 |
|  |  | Mean |  |  |  | 1.083 | 1.083 |
|  |  | Median |  |  |  | 1.083 | 1.083 |
|  |  | SD |  |  |  | 0.3536 | 0.3536 |
|  |  | Minimum |  |  |  | 0.83 | 0.83 |
|  |  | Maximum |  |  |  | 1.33 | 1.33 |
|  |  | Missing |  |  |  | 0 | 0 |
|  | WEAKNESS | N |  |  | 1 | 0 | 1 |
|  |  | Mean |  |  | 0.083 |  | 0.083 |
|  |  | Median |  |  | 0.083 |  | 0.083 |
|  |  | SD |  |  |  |  |  |
|  |  | Minimum |  |  | 0.08 |  | 0.08 |
|  |  | Maximum |  |  | 0.08 |  | 0.08 |
|  |  | Missing |  |  | 1 | 1 | 2 |
| WEEK 1/DAY 3 | HEADACHE | N | 1 |  | 1 | 1 | 3 |
|  |  | Mean | 0.083 |  | 5.625 | 9.125 | 4.944 |
|  |  | Median | 0.083 |  | 5.625 | 9.125 | 5.625 |
|  |  | SD |  |  |  |  | 4.5591 |
|  |  | Minimum | 0.08 |  | 5.63 | 9.13 | 0.08 |
|  |  | Maximum | 0.08 |  | 5.63 | 9.13 | 9.13 |
|  |  | Missing | 0 |  | 0 | 0 | 0 |
|  | MYALGIAS | N |  |  | 1 |  | 1 |
|  |  | Mean |  |  | 0.417 |  | 0.417 |
|  |  | Median |  |  | 0.417 |  | 0.417 |
|  |  | SD |  |  |  |  |  |
|  |  | Minimum |  |  | 0.42 |  | 0.42 |
|  |  | Maximum |  |  | 0.42 |  | 0.42 |
|  |  | Missing |  |  | 0 |  | 0 |
| WEEK 1/DAY 4 | HEADACHE | N |  |  | 1 |  | 1 |
|  |  | Mean |  |  | 5.625 |  | 5.625 |
|  |  | Median |  |  | 5.625 |  | 5.625 |
|  |  | SD |  |  |  |  |  |
|  |  | Minimum |  |  | 5.63 |  | 5.63 |
|  |  | Maximum |  |  | 5.63 |  | 5.63 |
|  |  | Missing |  |  | 0 |  | 0 |
| WEEK 2/DAY 8 | HEADACHE | N | 0 |  |  |  | 0 |
|  |  | Mean |  |  |  |  |  |
|  |  | Median |  |  |  |  |  |
|  |  | SD |  |  |  |  |  |
|  |  | Minimum |  |  |  |  |  |
|  |  | Maximum |  |  |  |  |  |
|  |  | Missing | 1 |  |  |  | 1 |
|  | MYALGIAS | N | 1 |  | 1 |  | 2 |
|  |  | Mean | 87.000 |  | 86.542 |  | 86.771 |
|  |  | Median | 87.000 |  | 86.542 |  | 86.771 |
|  |  | SD |  |  |  |  | 0.3241 |
|  |  | Minimum | 87.00 |  | 86.54 |  | 86.54 |
|  |  | Maximum | 87.00 |  | 86.54 |  | 87.00 |
|  |  | Missing | 0 |  | 0 |  | 0 |
|  | NAUSEA | N |  |  |  | 1 | 1 |
|  |  | Mean |  |  |  | 11.708 | 11.708 |
|  |  | Median |  |  |  | 11.708 | 11.708 |
|  |  | SD |  |  |  |  |  |
|  |  | Minimum |  |  |  | 11.71 | 11.71 |
|  |  | Maximum |  |  |  | 11.71 | 11.71 |
|  |  | Missing |  |  |  | 0 | 0 |

TABLE 17-continued

SUMMARY OF DURATION OF TREATMENT EMERGENT FLU SYMPTOMS
BY DOSE GROUP
(SAFETY POPULATION)

|  |  | Statistics | Locteron 160 ug N = 8 | Locteron 320 ug N = 8 | Locteron 480 ug N = 8 | Locteron 640 ug N = 8 | Total N = 32 |
|---|---|---|---|---|---|---|---|
| WEEK 2/DAY 8 | WEAKNESS | N | 0 |  |  |  | 0 |
|  |  | Mean |  |  |  |  |  |
|  |  | Median |  |  |  |  |  |
|  |  | SD |  |  |  |  |  |
|  |  | Minimum |  |  |  |  |  |
|  |  | Maximum |  |  |  |  |  |
|  |  | Missing | 1 |  |  |  | 1 |
| WEEK 2/DAY 12 | HEADACHE | N | 1 |  |  |  | 1 |
|  |  | Mean | 100.833 |  |  |  | 100.833 |
|  |  | Median | 100.833 |  |  |  | 100.833 |
|  |  | SD |  |  |  |  |  |
|  |  | Minimum | 100.83 |  |  |  | 100.83 |
|  |  | Maximum | 100.83 |  |  |  | 100.83 |
|  |  | Missing | 0 |  |  |  | 0 |
|  | WEAKNESS | N |  |  | 1 | 0 | 1 |
|  |  | Mean |  |  | 37.000 |  | 37.000 |
|  |  | Median |  |  | 37.000 |  | 37.000 |
|  |  | SD |  |  |  |  |  |
|  |  | Minimum |  |  | 37.00 |  | 37.00 |
|  |  | Maximum |  |  | 37.00 |  | 37.00 |
|  |  | Missing |  |  | 1 | 1 | 2 |
| WEEK 3/DAY 15 | HEADACHE | N | 1 |  |  |  | 1 |
|  |  | Mean | 1.000 |  |  |  | 1.000 |
|  |  | Median | 1.000 |  |  |  | 1.000 |
|  |  | SD |  |  |  |  |  |
|  |  | Minimum | 1.00 |  |  |  | 1.00 |
|  |  | Maximum | 1.00 |  |  |  | 1.00 |
|  |  | Missing | 0 |  |  |  | 0 |
|  | MYALGIAS | N |  |  |  | 1 | 1 |
|  |  | Mean |  |  |  | 93.000 | 93.000 |
|  |  | Median |  |  |  | 93.000 | 93.000 |
|  |  | SD |  |  |  |  |  |
|  |  | Minimum |  |  |  | 93.00 | 93.00 |
|  |  | Maximum |  |  |  | 93.00 | 93.00 |
|  |  | Missing |  |  |  | 0 | 0 |
| WEEK 3/DAY 15 | FEVER | N |  |  |  | 1 | 1 |
|  |  | Mean |  |  |  | 2.000 | 2.000 |
|  |  | Median |  |  |  | 2.000 | 2.000 |
|  |  | SD |  |  |  |  |  |
|  |  | Minimum |  |  |  | 2.00 | 2.00 |
|  |  | Maximum |  |  |  | 2.00 | 2.00 |
|  |  | Missing |  |  |  | 0 | 0 |
|  | WEAKNESS | N | 0 | 1 |  | 2 | 3 |
|  |  | Mean |  | 0.667 |  | 0.792 | 0.750 |
|  |  | Median |  | 0.667 |  | 0.792 | 0.667 |
|  |  | SD |  |  |  | 0.2946 | 0.2205 |
|  |  | Minimum |  | 0.67 |  | 0.58 | 0.58 |
|  |  | Maximum |  | 0.67 |  | 1.00 | 1.00 |
|  |  | Missing | 1 | 0 |  | 1 | 2 |
| WEEK 4/DAY 22 | HEADACHE | N |  | 1 | 1 |  | 2 |
|  |  | Mean |  | 79.875 | 87.000 |  | 83.438 |
|  |  | Median |  | 79.875 | 87.000 |  | 83.438 |
|  |  | SD |  |  |  |  | 5.0381 |
|  |  | Minimum |  | 79.88 | 87.00 |  | 79.88 |
|  |  | Maximum |  | 79.88 | 87.00 |  | 87.00 |
|  |  | Missing |  | 0 | 0 |  | 0 |
|  | MYALGIAS | N | 1 | 3 |  |  | 4 |
|  |  | Mean | 3.583 | 35.430 |  |  | 27.469 |
|  |  | Median | 3.583 | 40.500 |  |  | 22.042 |
|  |  | SD |  | 33.0227 |  |  | 31.3138 |
|  |  | Minimum | 3.58 | 0.17 |  |  | 0.17 |
|  |  | Maximum | 3.58 | 65.63 |  |  | 65.63 |
|  |  | Missing | 0 | 0 |  |  | 0 |
|  | FEVER | N |  | 1 |  |  | 1 |
|  |  | Mean |  | 0.458 |  |  | 0.458 |
|  |  | Median |  | 0.458 |  |  | 0.458 |
|  |  | SD |  |  |  |  |  |
|  |  | Minimum |  | 0.46 |  |  | 0.46 |
|  |  | Maximum |  | 0.46 |  |  | 0.46 |
|  |  | Missing |  | 0 |  |  | 0 |

TABLE 17-continued

SUMMARY OF DURATION OF TREATMENT EMERGENT FLU SYMPTOMS
BY DOSE GROUP
(SAFETY POPULATION)

|  |  | Statistics | Locteron 160 ug N = 8 | Locteron 320 ug N = 8 | Locteron 480 ug N = 8 | Locteron 640 ug N = 8 | Total N = 32 |
|---|---|---|---|---|---|---|---|
| WEEK 4/DAY 22 | WEAKNESS | N |  |  | 1 |  | 1 |
|  |  | Mean |  |  | 3.000 |  | 3.000 |
|  |  | Median |  |  | 3.000 |  | 3.000 |
|  |  | SD |  |  |  |  |  |
|  |  | Minimum |  |  | 3.00 |  | 3.00 |
|  |  | Maximum |  |  | 3.00 |  | 3.00 |
|  |  | Missing |  |  | 0 |  | 0 |
| WEEK 4/DAY 26 | MYALGIAS | N |  | 2 |  |  | 2 |
|  |  | Mean |  | 33.750 |  |  | 33.750 |
|  |  | Median |  | 33.750 |  |  | 33.750 |
|  |  | SD |  | 9.5459 |  |  | 9.5459 |
|  |  | Minimum |  | 27.00 |  |  | 27.00 |
|  |  | Maximum |  | 40.50 |  |  | 40.50 |
|  |  | Missing |  | 0 |  |  | 0 |
|  | WEAKNESS | N |  | 1 |  |  | 1 |
|  |  | Mean |  | 13.958 |  |  | 13.958 |
|  |  | Median |  | 13.958 |  |  | 13.958 |
|  |  | SD |  |  |  |  |  |
|  |  | Minimum |  | 13.96 |  |  | 13.96 |
|  |  | Maximum |  | 13.96 |  |  | 13.96 |
|  |  | Missing |  | 0 |  |  | 0 |
| WEEK 5/DAY 29 | MYALGIAS | N | 1 | 1 |  |  | 2 |
|  |  | Mean | 0.583 | 40.500 |  |  | 20.542 |
|  |  | Median | 0.583 | 40.500 |  |  | 20.542 |
|  |  | SD |  |  |  |  | 28.2253 |
|  |  | Minimum | 0.58 | 40.50 |  |  | 0.58 |
|  |  | Maximum | 0.58 | 40.50 |  |  | 40.50 |
|  |  | Missing | 0 | 0 |  |  | 0 |
| WEEK 6/DAY 36 | HEADACHE | N |  | 0 |  |  | 0 |
|  |  | Mean |  |  |  |  |  |
|  |  | Median |  |  |  |  |  |
|  |  | SD |  |  |  |  |  |
|  |  | Minimum |  |  |  |  |  |
|  |  | Maximum |  |  |  |  |  |
|  |  | Missing |  | 1 |  |  | 1 |
| WEEK 6/DAY 36 | MYALGIAS | N |  | 1 |  |  | 1 |
|  |  | Mean |  | 1.000 |  |  | 1.000 |
|  |  | Median |  | 1.000 |  |  | 1.000 |
|  |  | SD |  |  |  |  |  |
|  |  | Minimum |  | 1.00 |  |  | 1.00 |
|  |  | Maximum |  | 1.00 |  |  | 1.00 |
|  |  | Missing |  | 1 |  |  | 1 |
|  | FEVER | N | 1 |  |  |  | 1 |
|  |  | Mean | 0.708 |  |  |  | 0.708 |
|  |  | Median | 0.708 |  |  |  | 0.708 |
|  |  | SD |  |  |  |  |  |
|  |  | Minimum | 0.71 |  |  |  | 0.71 |
|  |  | Maximum | 0.71 |  |  |  | 0.71 |
|  |  | Missing | 0 |  |  |  | 0 |
|  | WEAKNESS | N |  | 1 |  |  | 1 |
|  |  | Mean |  | 1.000 |  |  | 1.000 |
|  |  | Median |  | 1.000 |  |  | 1.000 |
|  |  | SD |  |  |  |  |  |
|  |  | Minimum |  | 1.00 |  |  | 1.00 |
|  |  | Maximum |  | 1.00 |  |  | 1.00 |
|  |  | Missing |  | 0 |  |  | 0 |
| WEEK 7/DAY 43 | WEAKNESS | N |  | 1 | 0 | 1 | 2 |
|  |  | Mean |  | 54.958 |  | 1.542 | 28.250 |
|  |  | Median |  | 54.958 |  | 1.542 | 28.250 |
|  |  | SD |  |  |  |  | 37.7713 |
|  |  | Minimum |  | 54.96 |  | 1.54 | 1.54 |
|  |  | Maximum |  | 54.96 |  | 1.54 | 54.96 |
|  |  | Missing |  | 0 | 1 | 0 | 1 |
| WEEK 8/DAY 50 | HEADACHE | N |  |  |  | 1 | 1 |
|  |  | Mean |  |  |  | 17.000 | 17.000 |
|  |  | Median |  |  |  | 17.000 | 17.000 |
|  |  | SD |  |  |  |  |  |
|  |  | Minimum |  |  |  | 17.00 | 17.00 |
|  |  | Maximum |  |  |  | 17.00 | 17.00 |
|  |  | Missing |  |  |  | 0 | 0 |

TABLE 17-continued

SUMMARY OF DURATION OF TREATMENT EMERGENT FLU SYMPTOMS BY DOSE GROUP
(SAFETY POPULATION)

| | | Statistics | Locteron 160 ug N = 8 | Locteron 320 ug N = 8 | Locteron 480 ug N = 8 | Locteron 640 ug N = 8 | Total N = 32 |
|---|---|---|---|---|---|---|---|
| WEEK 8/DAY 50 | MYALGIAS | N | 1 | | | | 1 |
| | | Mean | 25.000 | | | | 25.000 |
| | | Median | 25.000 | | | | 25.000 |
| | | SD | | | | | |
| | | Minimum | 25.00 | | | | 25.00 |
| | | Maximum | 25.00 | | | | 25.00 |
| | | Missing | 0 | | | | 0 |
| WEEK 9/DAY 57 | HEADACHE | N | 1 | | 1 | | 2 |
| | | Mean | 0.583 | | 24.000 | | 12.292 |
| | | Median | 0.583 | | 24.000 | | 12.292 |
| | | SD | | | | | 16.5581 |
| | | Minimum | 0.58 | | 24.00 | | 0.58 |
| | | Maximum | 0.58 | | 24.00 | | 24.00 |
| | | Missing | 0 | | 0 | | 0 |
| | NAUSEA | N | 1 | | | | 1 |
| | | Mean | 0.583 | | | | 0.583 |
| | | Median | 0.583 | | | | 0.583 |
| | | SD | | | | | |
| | | Minimum | 0.58 | | | | 0.58 |
| | | Maximum | 0.58 | | | | 0.58 |
| | | Missing | 0 | | | | 0 |
| | WEAKNESS | N | 1 | | | | 1 |
| | | Mean | 1.583 | | | | 1.583 |
| | | Median | 1.583 | | | | 1.583 |
| | | SD | | | | | |
| | | Minimum | 1.58 | | | | 1.58 |
| | | Maximum | 1.58 | | | | 1.58 |
| | | Missing | 0 | | | | 0 |
| WEEK 10/DAY 64 | HEADACHE | N | 1 | | | | 1 |
| | | Mean | 1.000 | | | | 1.000 |
| | | Median | 1.000 | | | | 1.000 |
| | | SD | | | | | |
| | | Minimum | 1.00 | | | | 1.00 |
| | | Maximum | 1.00 | | | | 1.00 |
| | | Missing | 0 | | | | 0 |
| | MYALGIAS | N | 1 | | | | 1 |
| | | Mean | 1.000 | | | | 1.000 |
| | | Median | 1.000 | | | | 1.000 |
| | | SD | | | | | |
| | | Minimum | 1.00 | | | | 1.00 |
| | | Maximum | 1.00 | | | | 1.00 |
| | | Missing | 0 | | | | 0 |
| | FEVER | N | | 1 | | | 1 |
| | | Mean | | 1.167 | | | 1.167 |
| | | Median | | 1.167 | | | 1.167 |
| | | SD | | | | | |
| | | Minimum | | 1.17 | | | 1.17 |
| | | Maximum | | 1.17 | | | 1.17 |
| | | Missing | | 0 | | | 0 |
| | WEAKNESS | N | 1 | | | | 1 |
| | | Mean | 1.000 | | | | 1.000 |
| | | Median | 1.000 | | | | 1.000 |
| | | SD | | | | | |
| | | Minimum | 1.00 | | | | 1.00 |
| | | Maximum | 1.00 | | | | 1.00 |
| | | Missing | 0 | | | | 0 |
| WEEK 11/DAY 71 | HEADACHE | N | 1 | | | | 1 |
| | | Mean | 0.583 | | | | 0.583 |
| | | Median | 0.583 | | | | 0.583 |
| | | SD | | | | | |
| | | Minimum | 0.58 | | | | 0.58 |
| | | Maximum | 0.58 | | | | 0.58 |
| | | Missing | 0 | | | | 0 |
| | MYALGIAS | N | 1 | | | | 1 |
| | | Mean | 1.000 | | | | 1.000 |
| | | Median | 1.000 | | | | 1.000 |
| | | SD | | | | | |
| | | Minimum | 1.00 | | | | 1.00 |
| | | Maximum | 1.00 | | | | 1.00 |
| | | Missing | 0 | | | | 0 |

TABLE 17-continued

SUMMARY OF DURATION OF TREATMENT EMERGENT FLU SYMPTOMS
BY DOSE GROUP
(SAFETY POPULATION)

|  |  | Statistics | Locteron 160 ug N = 8 | Locteron 320 ug N = 8 | Locteron 480 ug N = 8 | Locteron 640 ug N = 8 | Total N = 32 |
|---|---|---|---|---|---|---|---|
|  | WEAKNESS | N | 1 |  |  |  | 1 |
|  |  | Mean | 6.792 |  |  |  | 6.792 |
|  |  | Median | 6.792 |  |  |  | 6.792 |
|  |  | SD |  |  |  |  |  |
|  |  | Minimum | 6.79 |  |  |  | 6.79 |
|  |  | Maximum | 6.79 |  |  |  | 6.79 |
|  |  | Missing | 0 |  |  |  | 0 |
| WEEK 13/DAY 85 | HEADACHE | N | 1 |  |  |  | 1 |
|  |  | Mean | 0.583 |  |  |  | 0.583 |
|  |  | Median | 0.583 |  |  |  | 0.583 |
|  |  | SD |  |  |  |  |  |
|  |  | Minimum | 0.58 |  |  |  | 0.58 |
|  |  | Maximum | 0.58 |  |  |  | 0.58 |
|  |  | Missing | 0 |  |  |  | 0 |
|  | MYALGIAS | N | 1 |  |  |  | 1 |
|  |  | Mean | 11.000 |  |  |  | 11.000 |
|  |  | Median | 11.000 |  |  |  | 11.000 |
|  |  | SD |  |  |  |  |  |
|  |  | Minimum | 11.00 |  |  |  | 11.00 |
|  |  | Maximum | 11.00 |  |  |  | 11.00 |
|  |  | Missing | 0 |  |  |  | 0 |
|  | WEAKNESS | N |  |  |  | 0 | 0 |
|  |  | Mean |  |  |  |  |  |
|  |  | Median |  |  |  |  |  |
|  |  | SD |  |  |  |  |  |
|  |  | Minimum |  |  |  |  |  |
|  |  | Maximum |  |  |  |  |  |
|  |  | Missing |  |  |  | 1 | 1 |
| WEEK 14 END/DAY 92 | HEADACHE | N |  | 1 |  |  | 1 |
|  |  | Mean |  | 1.375 |  |  | 1.375 |
|  |  | Median |  | 1.375 |  |  | 1.375 |
|  |  | SD |  |  |  |  |  |
|  |  | Minimum |  | 1.38 |  |  | 1.38 |
|  |  | Maximum |  | 1.38 |  |  | 1.38 |
|  |  | Missing |  | 0 |  |  | 0 |

The most frequently experienced influenza-like symptom was asthenia (19 patients, 59.4%), with 4 patients (50.0%) in the 160 μg, 320 μg and 480 μg treatments groups experiencing such an event and 7 patients (87.5%) experiencing asthenia in the 640 μg treatment group. Headache was experienced by a total of 14 patients (43.8%) and myalgia was experienced by a total of 13 patients (40.6%), with no notable differences between treatment groups. Chills were reported by only one patient, in the 320 μg treatment group (3.1%). A total of 7 patients (21.9%) experienced an AE of pyrexia during the study, with the highest frequency being in the 640 μg treatment group (4 patients (50.0%)). There were 4 patients (12.5%) who experienced nausea during the study, with no notable difference between treatment groups.

The frequency of influenza-like symptoms by visit remained low for the duration of the study, with no more than 6 patients experiencing any one symptom at any visit. From Week 10/Day 84 until the final assessment (Week 14/Day 92), no influenza-like symptoms were experienced by any more than one patient at each visit. No differences of note were observed across treatment groups.

The duration of treatment-emergent influenza-like symptoms was assessed at each visit. No notable differences were observed across treatment groups in the duration of symptoms. The most frequently occurring symptom at any one visit was headache at Baseline/Day 1, with 6 occurrences and an average duration of 5.0 days across all treatment groups at this visit. The longest mean duration of headache at this visit occurred in the 640 μg group (2 patients, mean duration: 11.8 days). However, at the next visit (Week 1/Day 2), only 1 occurrence of headache was observed and at the last assessment (Week 14/Day 92) there was also just 1 occurrence of headache in all treatment groups.

The influenza-like symptoms with the longest mean durations were headache at Week 2/Day 12 (1 patient, duration: 100.8 days) and myalgias at Week 2/Day 8 (2 patients, mean duration: 86.8 days).

Laboratory Values Over Time—Haematology

The majority of mean values for each of the haematology parameters were within the normal reference ranges during the study. However, the following exceptions of note were observed during the study:

White blood cells (WBC): in the 640 μg treatment group, a mean value that was within the normal reference range (3.50 to $11.10 \times 10^9$/L) at Screening and Baseline/Day 1, fell below the reference range at Week 7/Day 43, and did not return to a normal value until Week 14/Day 92. Out of range mean values were not noted in any other treatment groups.

Haemoglobin (HGB): in the 320 μg and 480 μg treatment groups, mean values were above the normal reference range (11.5 to 15.5 g/dL) at Screening and Baseline/Day 1 fell to within the normal range from Week 3/Day 15 onwards.

Absolute (ABS) Neutrophils: in the 640 μg treatment group, mean values within the normal reference range (1.80 to 7.00×10$^9$/L) at Screening and Baseline/Day 1 fell below the normal reference range on Week 2/Day 8, and then again at Week 5/Day 29, before returning to within the normal range at Week 14/Day 92. FIG. 11 shows absolute neutrophil count for the treatment group.

Monocytes: in the 320 µg, 480 µg and 640 µg treatment groups, mean values within the normal reference range (3.4 to 9.0%) at Baseline/Day 1 increased to above normal values at Week 1/Day 3, falling to normal or near normal values at subsequent visits.

Mean Corpuscular Haemoglobin Concentration (MCHC): from Baseline/Day 1 and throughout the study, the mean value was below the normal reference range (32.0 to 36.0 g/dL) in the 640 µg treatment group, and in all groups by Week 14/Day 92. FIG. 12 shows hematocrit for study cohorts. No subject fell below 30%.

No notable trends were observed for any other haematology parameters.

Laboratory Values Over Time—Biochemistry

The majority of mean values for each of the biochemistry parameters were within the normal reference ranges during the study. However, the following exceptions of note were observed during the study:

Total Protein: mean values above the normal reference range (61 to 79 g/L) in all groups at either Screening or Baseline/Day 1, fell to normal or near normal values in all groups from Week 3/Day 15 onwards.

Uric Acid: mean values above the normal reference range (130 to 379 µmol/L) were observed in the 320 µg group at Baseline/Day 1 and from Week 1/Day 3, returning to normal at Week 11/Day 71. Values in the other groups remained within the normal range, except for the 160 µg group at Week 5/Day 29 and Week 9/Day 57.

ALT: it should be noted that high ALT values are an inclusion criterion for this study. The mean values in all groups were above the normal reference range (0 to 47.0 U/L) at Baseline/Day 1, with the values in the 320 µg and 480 µg treatment groups being notably higher. In all groups, mean values fell progressively to normal or near normal values by Week 7/Day 43, with the value in the 640 µg treatment group falling to within the normal range by Week 3/Day 15. FIG. 13 shows ALT level for study groups.

AST: it should be noted that high AST values were initially a criterion for inclusion in the study, but this was removed in Protocol Amendment 1. Mean values above the normal reference range (0 to 37.0 U/L) in all groups at Screening and Baseline/Day 1, fell steadily to normal or near normal values in all groups by Week 5/Day 29. In the 640 µg treatment group, a normal mean value was achieved from Week 2/Day 8, though it should be noted that the value at Baseline/Day 1 was also lower in this group than in the other groups.

No notable trends were observed for any other biochemistry parameters.

Laboratory Values Over Time—Urinalysis

No notable values or trends were observed for any urinalysis parameters over time or across treatment groups.

Individual Patient Changes—Haematology

For the majority of haematology parameters analysed, most patients were considered to have normal values during the study. However, exceptions were observed, including the most frequent as follows:

Most Frequent Low Values Outside the Normal Reference Range:

MCHC: at Week 11/Day 71, a peak frequency of 23 patients (71.9%) had values below the normal reference range (32.0 to 36.0 g/dL). No notable differences in the frequency and occurrence of these low values were observed across treatment groups. At the final assessment (Week 14/Day 92), there were 21 patients (65.6%) overall with low MCHC values.

ABS Neutrophils: at Week 3/Day 15 and Week 7/Day 43, a peak frequency of 14 patients (43.8%) had values below the normal reference range (1.80 to 7.00×10$^9$/L). A slightly greater frequency of these low values occurred in the 640 µg treatment group at Week 3/Day 15 (6 patients, 75.0%) and Week 7/Day 43 (7 patients, 87.5%). At the final assessment (Week 14/Day 92), the frequency of patients with low ABS neutrophil values had decreased to 7 patients (21.9%) overall.

Neutrophils: at Week 3/Day 15, a peak frequency of 14 patients (43.8%) had values below the normal reference range (40.0 to 74.0%). No notable differences in the frequency and occurrence of these low values was observed across the 320 µg, 480 µg and 640 µg treatment groups; however, no low values were observed in the 160 µg treatment group at this visit. At the final assessment (Week 14/Day 92), the frequency of patients with low neutrophil values had decreased to 3 patients (9.4%) overall.

Red blood cells (RBC): at Week 7/Day 43 and Week 14/Day 92, a peak frequency of 13 patients (40.6%) had values below the normal reference range (3.80 to 5.40×10$^{12}$/L). The 160 µg had the lowest frequency of low values (2 patients, 25.0%) at Week 7/Day 43, and a slightly greater frequency of patients in the 640 µg treatment group had low values at Week 14/Day 92 (5 patients, 62.5%) compared to the other treatment groups. At the final assessment (Week 14/Day 92), the frequency of patients with low RBC values remained at 13 patients (40.6%) overall.

HGB: at Week 7/Day 43, a peak frequency of 11 patients (34.4%) had values below the normal reference range (11.5 to 15.5 g/dL). The greatest frequency of these low values occurred in the 640 µg treatment group (6 patients, 54.5%). At the final assessment (Week 14/Day 92), the frequency of patients with low HGB values had decreased to 6 patients (18.8%) overall.

For all other haematology parameters, a maximum of 9 patients (28.1%) or fewer had low values outside of the normal reference ranges at any one visit during the study.

Most Frequent High Values Outside the Normal Reference Range:

Monocytes: at Week 1/Day 3, a peak frequency of 18 patients (56.3%) had values above the normal reference range (3.4 to 9.0%). The greatest frequency of these high values occurred in the 320 µg treatment group (7 patients, 87.5%). At the final assessment (Week 14/Day 92), the frequency of patients with high monocyte values had reduced to 7 patients (21.9%) overall.

Lymphocytes: at Week 3/Day 15, a peak frequency of 15 patients (46.9%) had values above the normal reference range (19.0 to 48.0%). A slightly greater frequency of these high values occurred in the 640 µg treatment group (6 patients, 75.0%). At the final assessment (Week 14/Day 92), the frequency of patients with high lymphocyte values had decreased to 3 patients (6.3%) overall.

Mean Corpuscular Volume (MCV): at Week 14/Day 92, a peak frequency of 13 patients (40.6%) had values above the normal reference range (80.0 to 104.0 fL). At this visit, the 160 µg and 320 µg treatment groups had 4 patients (50.0%) each with high values whereas the 640 µg treatment group had 2 patients (25.0%) with high values. At the final assessment (Week 14/Day 92), the frequency of patients with high MCV values remained at 13 patients (40.6%) overall.

Basophils: at Baseline/Day 1 and Week 3/Day 15, a peak frequency of 8 patients (25.0%) had values above the normal reference range (0.0 to 1.5%). These high values were the same as at Screening. No notable differences in the frequency and occurrence of these high basophil values were observed across treatment groups. At the final assessment (Week 14/Day 92), the frequency of patients with high basophil values had decreased to 3 patients (9.4%) overall.

Mean Corpuscular Haemoglobin (MCH): at the final assessment (Week 14/Day 92), a peak frequency of 8 patients (25.0%) had values above the normal reference range (27.0 to 33.0 pg), compared to 3 patients (9.4%) at Baseline/Day 1. No notable differences in the frequency and occurrence of these high MCH values were observed across treatment groups.

For all other haematology parameters, a maximum of 6 patients (18.8%) or fewer had high values outside of the normal reference ranges at any one visit during the study.

Individual Patient Changes—Biochemistry

For the majority of biochemistry parameters analysed, most patients were considered to have normal values during the study. However, exceptions were observed, including the most frequent as follows:

Most Frequent Low Values Outside the Normal Reference Range:
Urea (BUN): at the final assessment (Week 14/Day 92), a peak frequency of 9 patients (28.1%) had values below the normal reference range (3.2 to 8.6 mmol/L), compared to 3 patients (9.4%) at Baseline/Day 1. No notable differences in the frequency or occurrence of these low BUN values were observed across treatment groups.

For all other biochemistry parameters, a maximum of 2 patients (6.3%) or fewer had low values outside of the normal reference ranges at any one visit during the study.

Most Frequent High Values Outside the Normal Reference Range:
ALT: it should be noted that high ALT values were a criterion for inclusion in the study. The frequency of patients with ALT values above the normal reference range was at its highest at Screening (Weeks −4 to −2) than at any time during the study (32 patients, 100.0%). During the study period, a peak frequency of 29 patients (90.6%) had values above the normal reference range (0 to 47.0 U/L) at Week 1/Day 3. No notable differences in the frequency or occurrence of these high ALT values were observed across treatment groups. At the final assessment (Week 14/Day 92), the frequency of patients with high ALT values had decreased to 6 patients (18.8%) overall.

AST: it should be noted that high AST values were initially a criterion for inclusion in the study, but this was removed in Protocol Amendment 1. At Baseline/Day 1, a peak frequency of 28 patients (87.5%) had values above the normal reference range (0 to 37.0 U/L). This frequency was higher at Screening (Weeks −4 to −2) than at any time during the study (30 patients, 93.8%). No notable differences in the frequency or occurrence of these high ALT values were observed across treatment groups. At the final assessment (Week 14/Day 92), the frequency of patients with high AST values had decreased to 5 patients (15.6%) overall.

Total protein: at Baseline/Day 1 and Week 2/Day 8, a peak frequency of 14 patients (43.8%) had values above the normal reference range (61 to 79 g/L). This frequency was higher at Screening (Weeks −4 to −2) than at any time during the study (15 patients, 46.9%). The greatest frequency of these high values at both visits occurred in the 160 μg and 320 μg treatment groups, with 5 patients (62.5%) having high values in the 160 μg treatment group at both Baseline/Day 1 and Week 2/Day 8 and 6 patients (75.0%) having a high value in the 320 μg treatment group at Week 2/Day 8 (4 patients, 50.0% at Baseline/Day 1). At the final assessment (Week 14/Day 92), the frequency of patients with high total protein values had decreased to 2 patients (6.3%) overall.

Total cholesterol: at Baseline/Day 1, a peak frequency of 11 patients (34.4%) had values above the normal reference range (0.00 to 5.17 mmol/L). This frequency was higher at Screening (Weeks −4 to −2) than at any time during the study (12 patients, 37.5%). No notable differences in the frequency or occurrence of these high total cholesterol values were observed across treatment groups. At the final assessment (Week 14/Day 92), the frequency of patients with high total cholesterol values had decreased to 6 patients (18.8%) overall.

For all other biochemistry parameters, a maximum of 7 patients (21.9%) or fewer had high values outside of the normal reference ranges at any one visit during the study.

Individual Patient Changes—Urinalysis

Of all the urinalysis parameters (pH, blood, protein urine, glucose urine, specific gravity), no high or low out of range values of high frequency were observed during the study in any patients at any visits.

Individual Clinically Significant Abnormalities

A summary of laboratory abnormalities reported as AEs in patients in the Safety Population is presented by preferred term in Table 18.

TABLE 18

Summary of patients experiencing individual laboratory abnormalities reported as AEs by preferred term and treatment group (Safety Population; N = 32)

| Preferred Term | LOCTERON™ 160 μg N = 8 n (%) | LOCTERON™ 320 μg N = 8 n (%) | LOCTERON™ 480 μg N = 8 n (%) | LOCTERON™ 640 μg N = 8 n (%) | Total N = 32 n (%) |
|---|---|---|---|---|---|
| Neutrophil count decreased | 2 (25.0) | 2 (25.0) | 2 (25.0) | 2 (25.0) | 8 (25.0) |
| White blood cell count decreased | 2 (25.0) | 1 (12.5) | 2 (25.0) | 2 (25.0) | 7 (21.9) |
| Red blood cell count decreased | 2 (25.0) | 1 (12.5) | 1 (12.5) | 2 (25.0) | 6 (18.8) |
| Haemoglobin decreased | 1 (12.5) | 1 (12.5) | 1 (12.5) | 2 (25.0) | 5 (15.6) |

TABLE 18-continued

Summary of patients experiencing individual laboratory abnormalities reported as AEs by preferred term and treatment group (Safety Population; N = 32)

| Preferred Term | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|
| Bilirubin conjugated increased | 1 (12.5) | 1 (12.5) | 2 (25.0) | 0 (0.0) | 4 (12.5) |
| Blood bilirubin increased | 1 (12.5) | 2 (25.0) | 0 (0.0) | 0 (0.0) | 3 (9.4) |
| Lymphocyte count decreased | 1 (12.5) | 0 (0.0) | 1 (12.5) | 1 (12.5) | 3 (9.4) |
| Platelet count decreased | 1 (12.5) | 0 (0.0) | 0 (0.0) | 1 (12.5) | 2 (6.3) |
| Blood glucose increased | 0 (0.0) | 0 (0.0) | 1 (12.5) | 0 (0.0) | 1 (3.1) |
| Blood thyroid stimulating hormone | 0 (0.0) | 0 (0.0) | 0 (0.0) | 1 (12.5) | 1 (3.1) |

The most frequently experienced laboratory abnormalities reported as AEs were neutrophil count decreased (8 patients, 25%), WBC count decreased (7 patients, 21.9%) and RBC count decreased (6 patients (18.8%)). No notable differences in the frequency of laboratory abnormalities reported as AEs was observed between treatment groups.

Immunology

In the screening method for anti-IFNα activity binding antibodies, anti-IFNα(BAB), the majority (19 patients) were negative at all assessments. The purpose of this method was to select the samples for the neutralising antibodies assay, anti-IFNα(NAB). Thirteen patients were either positive or equivocal and samples of all 13 were taken for testing by neutralisation assay. Of the samples from the 13 patients with either positive or equivocal results in the binding assay, only 2 tested positive in the neutralisation assay, i.e. one in the 160 μg group and one in the 640 μg group. The patient in the 160 μg group was positive at baseline, prior to dosing.

Serum samples that tested 'positive' for the presence of neutralising antibodies against IFNα2b were tested using the surface plasmon response (SPR) technology on a BiaCore 2000® instrument antibodies against human IFNα2b to determine binding affinity and Ig isotype. In the BiaCore system antibodies were detected in only one sample from the patient receiving the 640 μg dose, i.e. after last visit (Visit 16, Day 92). The antibodies in that sample was considered to be of low affinity. The immune response was mediated by IgG antibodies. These antibodies were mainly of IgG1 subclass followed by IgG2. IgG3 and IgG4 were not detected by this method.

Individual and summary demographic and covariate data, including immunology results, are presented in Table 19.

TABLE 19

Individual and summary demographic and covariate data, including immunology results

| Patient | Centre | Dose (μg/2 wks) | RBVR[1] (mg/day) | Gender | Weight (kg) | Age (years) | Anti-IFNα (NAB) status |
|---|---|---|---|---|---|---|---|
| 01/01 | 1 | 480 | 800 | male | 62.0 | 36 | negative |
| 01/02 | 1 | 640[2] | 800 | female | 62.3 | 36 | negative |
| 01/03 | 1 | 480 | 1200 | male | 86.0 | 30 | negative |
| 01/08 | 1 | 640 | 1000 | male | 71.7 | 21 | negative |
| 01/09 | 1 | 320 | 1000 | female | 72.0 | 31 | negative |
| 01/10 | 1 | 160 | 800 | female | 62.0 | 29 | negative |
| 01/13 | 1 | 640 | 1000 | female | 65.3 | 60 | negative |
| 01/14 | 1 | 320[3] | 1200 | male | 114.0 | 39 | negative |
| 01/16 | 1 | 160 | 1000 | male | 83.0 | 48 | negative |
| 01/17 | 1 | 480[4] | 1200 | male | 86.0 | 41 | negative |
| 01/21 | 1 | 160 | 1000 | male | 74.0 | 30 | negative |
| 02/01 | 2 | 480 | 1000 | female | 70.0 | 48 | negative |
| 02/03 | 2 | 640 | 1000 | female | 83.0 | 42 | negative |
| 02/04 | 2 | 320 | 1200 | male | 95.0 | 49 | negative |
| 02/06 | 2 | 160 | 1000 | female | 66.0 | 32 | negative |
| 02/07 | 2 | 160 | 800 | female | 52.0 | 36 | negative |
| 02/11 | 2 | 480 | 800 | female | 61.0 | 51 | negative |
| 02/13 | 2 | 640 | 1000 | male | 76.0 | 37 | negative |
| 02/15 | 2 | 320 | 800 | male | 61.0 | 22 | negative |
| 03/01 | 3 | 640 | 800 | male | 95.0 | 48 | positive at wk 14 |
| 03/02 | 3 | 480 | 1200 | male | 106.0 | 28 | negative |
| 03/03 | 3 | 640 | 1200 | female | 100.0 | 41 | negative |
| 03/04 | 3 | 480 | 800 | male | 56.0 | 25 | negative |
| 03/05 | 3 | 320 | 1000 | male | 76.0 | 30 | negative |
| 03/06 | 3 | 320 | 1000 | male | 82.0 | 39 | negative |
| 03/07 | 3 | 160 | 1000 | female | 78.0 | 48 | negative |
| 03/08 | 3 | 160 | 1000 | male | 80.0 | 39 | negative |
| 03/10 | 3 | 640 | 1000 | male | 75.0 | 33 | negative |
| 03/11 | 3 | 160 | 1200 | female | 96.0 | 50 | positive at wk 1 (pre-dose) and wk 14 |

TABLE 19-continued

Individual and summary demographic and covariate data, including immunology results

| Patient | Centre | Dose (μg/2 wks) | RBVR[1] (mg/ day) | Gender | Weight (kg) | Age (years) | Anti-IFNα (NAB) status |
|---|---|---|---|---|---|---|---|
| 03/12 | 3 | 480 | 1200 | male | 100.0 | 45 | negative |
| 03/15 | 3 | 320 | 1000 | male | 85.0 | 23 | negative |
| 03/17 | 3 | 320 | 1000 | male | 85.0 | 47 | negative |
| N | 32 | 32 | 32 | 32 | 32 | 32 | 32 |
| Mean | | | | | 78.63 | 37.9 | |
| SD | | | | | 15.25 | 9.7 | |
| CV % | | | | | 19.4 | 19.4 | |
| Min | | | | | 52.0 | 21 | |
| Median | | | | | 77.00 | 38.0 | |
| Max | | | | | 114.0 | 60 | |

[1]ribavirin daily dose;
[2]patient received one 640 μg dose, three 320 μg doses, one 160 μg dose and did not receive a 6th dose;
[3]patient received one 320 μg dose and then five 160 μg doses;
[4]patient received two 480 μg doses and then four 240 μg doses As can be seen in Table 19, of the 11 patients with positive anti-IFNα(BAB) screening results, Patient 03/11 was found anti-IFNα(NAB) positive at the Week 1 and Week 14/Day 92 assessments and Patient 03/01 was found anti-IFNα(NAB) positive at the Week 14/Day 92 assessment.

Vital Signs, Physical Findings, and Other Observations Related to Safety

Vital Signs

There were no notable changes over time in any treatment group with regard to systolic blood pressure, diastolic blood pressure, pulse, respiratory rate, and body temperature. There was a small mean loss of weight across all groups from Baseline/Day 1 to Week 14/Day 92. This ranged from approximately 1 kg in the 160 μg treatment group to 4.5 kg in the 640 μg treatment group, with a mean value across all groups of 2.5 kg.

Physical Examination

At Screening, 23 patients (71.9%) had an abnormal finding for the body system abdomen, which increased to 24 patients (75.0%) at Week 3/Day 15 and then decreased by Week 14/Day 92 to 20 patients (62.5%). There was 1 patient (3.1%) with an abnormal skin finding at Screening, which increased to 11 patients (34.4%) at Week 9/Day 57 and then decreased to 8 patients (25.0%) by Week 14/Day 92. For all other body systems, the majority of physical examination findings were normal at each visit during the study.

Injection Site Reactions

The majority of patients at each visit did not experience any injection site reactions. However, of those patients experiencing injection site reactions, the most prevalent was redness, which first occurred at Week 1/Day 2 in the 480 μg and 640 μg groups, in all but the 320 μg group at Week 2/Day 8, and in all treatment groups at all other visits. It affected no more than 4 patients (50.0%) in each group at any one visit, and occurred with similar frequency across all treatment groups; in the highest dose group of 640 μg the prevalence of redness did not exceed 37.5%. Induration occurred in all treatment groups, but in no more than 2 patients (25.0%) in any one treatment group at any visit. Largest diameters of areas with redness and induration observed were 100 mm and 150 mm, respectively, both in the 640 μg group. In the assessment of the investigator, this most likely represented the areas of confluence of the 4 injections required for the 640 μg dose that the patient had received in the thigh. Tenderness occurred most frequently in the 640 μg treatment group, and with similar frequency in the other groups, though in no more than 2 patients (25.0%) in any one treatment group at any visit. Other reactions occurred infrequently in all groups, usually no more than 1 patient (12.5%) in any group at any visit.

At the last study visit (Day 92), a small frequency of patients remained with residual injection site reactions. It was confirmed on further follow-up that for all of these patients the residual injection site reactions resolved completely without intervention.

It should be noted that for each patient receiving multiple injections at one administration, the injection site reaction is classified as a summary of these injections. Injection site reactions by individual patient are presented in Appendix 14.2, Listing 19.

ECG

Mean ECG parameters were assessed at Screening, Baseline/Day 1, Week 1/Day 3, Week 7/Day 43, and at follow-up at Week 14/Day 92. The following trends were observed:

PR interval: mean values changed little through the study (range 153.3 ms to 161.4 ms), being 158.4 ms at Baseline/Day 1 and 153.3 ms at Week 14/Day 92.

QRS duration: mean values were slightly lower at Week 14/Day 92 (77.7 ms) than at Baseline/Day 1 (83.7 ms).

QT-corrected interval: mean values fell from 365.5 ms at Baseline/Day 1 to 333.0 ms at Week 7/Day 43, rising to 374.7 ms at Week 14/Day 92. The same pattern occurred for the mean values for the QT interval.

The overall interpretation of ECG demonstrated that most patients had normal or abnormal but not clinically significant ECG at all assessed visits, as presented in Table 20 below.

TABLE 20

Summary of ECG interpretation by treatment group (Safety Population; N = 32)

| Visit | Category | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|---|
| Screening/ Weeks −4 to −2 | Norm | 4 (50.0) | 4 (50.0) | 3 (37.5) | 3 (37.5) | 14 (43.8) |
| | Abnorm, NCS | 4 (50.0) | 4 (50.0) | 4 (50.0) | 5 (62.5) | 17 (53.1) |
| | Abnorm, CS | 0 (0.0) | 0 (0.0) | 1 (12.5) | 0 (0.0) | 1 (3.1) |

TABLE 20-continued

Summary of ECG interpretation by treatment group (Safety Population; N = 32)

| Visit | Category | LOCTERON ™ 160 μg N = 8 n (%) | LOCTERON ™ 320 μg N = 8 n (%) | LOCTERON ™ 480 μg N = 8 n (%) | LOCTERON ™ 640 μg N = 8 n (%) | Total N = 32 n (%) |
|---|---|---|---|---|---|---|
| Baseline/Day 1 | Norm | 4 (50.0) | 5 (62.5) | 4 (50.0) | 3 (37.5) | 16 (50.0) |
| | Abnorm, NCS | 4 (50.0) | 3 (37.5) | 3 (37.5) | 5 (62.5) | 15 (46.9) |
| | Abnorm, CS | 0 (0.0) | 0 (0.0) | 1 (12.5) | 0 (0.0) | 1 (3.1) |
| Week 1/Day 3 | Norm | 5 (62.5) | 4 (50.0) | 4 (50.0) | 2 (25.0) | 15 (46.9) |
| | Abnor, NCS | 3 (37.5) | 4 (50.0) | 3 (37.5) | 6 (75.0) | 16 (50.0) |
| | Abnor, CS | 0 (0.0) | 0 (0.0) | 1 (12.5) | 0 (0.0) | 1 (3.1) |
| Week 7/Day 43 | Norm | 4 (50.0) | 3 (37.5) | 3 (37.5) | 3 (37.5) | 13 (40.6) |
| | Abnorm, NCS | 4 (50.0) | 5 (62.5) | 5 (62.5) | 5 (62.5) | 19 (59.4) |
| | Abnorm, CS | 0 (0.0) | 0 (0.0) | 0 (0.0) | 0 (0.0) | 0 (0.0) |
| Week 14/Day 97 | Norm | 5 (62.5) | 1 (12.5) | 3 (37.5) | 5 (62.5) | 14 (43.8) |
| | Abnorm, NCS | 3 (37.5) | 7 (87.5) | 4 (50.0) | 3 (37.5) | 17 (53.1) |
| | Abnorm, CS | 0 (0.0) | 0 (0.0) | 1 (12.5) | 0 (0.0) | 1 (3.1) |

Footnote 1:
Abnorm: Abnormal;
Norm: Normal;
NCS—not clinically significant,
CS—clinically significant Only one patient (in the 480 μg treatment group) had an abnormal and clinically significant ECG finding at any time point. The abnormal ECG occurred at Screening, Baseline/Day 1, Week 1/Day 3, and at Week 14/Day 97, and was interpreted as left ventricle ischaemia as from Screening. There was no clinically significant abnormality reported at Week 7/Day 43.

Safety Conclusions

In the Safety Population, 31 patients (96.9%) experienced treatment-emergent AEs (including influenza-like symptoms). The most common AEs by preferred term were asthenia (19 patients, 59.4%), arthralgia (16 patients, 50.0%) and headache (14 patients, 43.8%). Of note, it was observed that for the AEs of neutropenia and leukopenia, a higher frequency of patients in the 640 μg group (6 patients, 75.0%, and 4 patients, 50.0%, respectively) experienced these events than in all other dose groups, with no patients experiencing such events in the 160 μg group. The most frequently experienced laboratory abnormalities reported as AEs were neutrophil count decreased (8 patients, 25%), WBC count decreased (7 patients, 21.9%) and RBC count decreased (6 patients, 18.8%). No notable differences in the frequency of laboratory abnormalities reported as AEs was observed between treatment groups. Of patients experiencing AEs possibly/probably related to study medication, 10 patients (32.3%) experienced AEs that were considered mild in severity and 18 patients (58.1%) experienced AEs considered moderate in severity. In total, 3 patients (9.7%) experienced severe AEs and all were considered related to study medication. Amongst these, one patient randomised to the 640 μg Locteron™ dose experienced a SAE; they were hospitalised with otitis and neutropenia. In this patient, treatment was discontinued after the fifth dose of Locteron™.

The most frequently experienced influenza-like symptom was asthenia (19 patients, 59.4%), with 4 patients (50.0%) in the 160 μg, 320 μg and 480 μg treatments groups experiencing such an event and 7 patients (87.5%) experiencing asthenia in the 640 μg treatment group. Headache was experienced by a total of 14 patients (43.8%) and myalgia was experienced by a total of 13 patients (40.6%), with no notable differences between treatment groups. A total of 7 patients (21.9%) experienced an AE of pyrexia during the study, with the highest frequency being in the 640 μg treatment group (4 patients, 50.0%), whereas at the lower doses, pyrexia was reported 2 or fewer patients per treatment group. There were 4 patients (12.5%) who experienced nausea during the study, with no notable difference between treatment groups. Chills were reported by one patient (3.1%) in the 320 μg treatment group.

The frequency and duration of treatment-emergent influenza-like symptoms was assessed at each visit. The most frequently occurring symptom at any one visit was headache at Baseline/Day 1, with 6 occurrences and an average duration of 5.0 days across all treatment groups at this visit. The longest mean duration of headache at this visit occurred in the 640 μg group (2 patients, mean duration: 11.8 days), the intensity of these being mild and moderate. At the next visit (Week 1/Day 2), only 1 occurrence of headache was observed and at the last assessment (Week 14/Day 92) there was also just 1 occurrence of headache in all treatment groups. The influenza-like symptoms with the longest mean durations were headache at Week 2/Day 12 (1 patient, duration: 100.8 days) and myalgias at Week 2/Day 8 (2 patients, mean duration: 86.8 days).

The majority of mean values for haematology parameters were within the normal reference ranges during the study, with some exceptions, most notably WBC, HGB, ABS neutrophils, monocytes and MCHC, with each having mean values outside of the normal reference ranges for at least one visit. The biochemistry parameters of ALT, AST, total protein and uric acid each had mean values outside of the reference ranges for at least one visit during the study. The majority of other biochemistry parameters had mean values that remained within the normal reference ranges at each visit. All mean values for all of the urinalysis parameters remained within the normal reference ranges for the duration of the study.

For the majority of haematology and biochemistry parameters analysed, most patients had normal values during the study. However, some high frequencies of high and low values outside the normal reference ranges were observed. The highest frequencies of low values outside the normal references ranges were observed for MCHC, ABS neutrophils, neutrophils, RBC, HGB and urea, with the most frequent being MCHC (peak frequency of 23 patients, 71.9%, at Week 11/Day 71). The highest frequencies of high values above the normal reference ranges were observed for monocytes, lymphocytes, MCV, basophils, MCH, ALT, AST, total protein and total cholesterol, with the most frequent being monocytes (peak frequency of 18 patients, 56.3%, at Week 1/Day 3). No out of range values were observed for any urinalysis parameters.

The laboratory parameters most frequently reported as AEs during the study were neutrophil count decreased (8 patients, 25%), WBC count decreased (7 patients, 21.9%) and RBC count decreased (6 patients, 18.8%). No notable differences in the frequency of laboratory abnormalities reported as AEs was observed between treatment groups.

There were no notable changes over time in any treatment group with regard to systolic blood pressure, diastolic blood pressure, pulse, respiratory rate, and body temperature. There was a mean loss of weight across all groups from Baseline/Day 1 to Week 14/Day 92 of 2.5 kg.

For the majority of body systems, the physical examination findings were normal at each visit during the study. At Screening, 23 patients (71.9%) had an abnormal finding for the body system abdomen, which had decreased by Week 14/Day 92 to 20 patients (62.5%). There was 1 patient (3.1%) with an abnormal skin finding at Screening, which increased to 8 patients (25.0%) by Week 14/Day 92. This increase was observed across all treatment groups.

The majority of patients did not experience injection site reactions at each visit, but of those who did, the most prevalent was redness, which occurred in all treatment groups, but as early as Week 1/Day 2 in the 480 µg and 640 µg groups. It affected no more than 4 patients (50.0%) in each group at any one visit, and occurred with similar frequency across all treatment groups.

There was only one patient (in the 480 µg treatment group) with an abnormal and clinically significant ECG at any timepoint, including Screening.

DISCUSSION AND OVERALL CONCLUSIONS

This was a phase II, multicentre, open-label, randomised study to assess the safety and tolerability, pharmacokinetics, pharmacodynamics and preliminary efficacy of 4 doses of Locteron™, in patients with chronic hepatitis C on co-medication with ribavirin.

A total of 54 patients were screened in 3 centres in one country; Ukraine. Of these, 32 patients were randomised into one of four treatment groups, i.e. 160 µg, 320 µg, 480 µg and 640 µg, every 2 weeks, for a period of 12 weeks.

A total of 31 patients completed the study, with one patient discontinuing due to AE. The majority of patients were fully treatment compliant during the study with the only exception being the withdrawn patient.

The assessment of the safety of Locteron™ in the populations studied revealed that although the majority of patients did experience AEs during the study, only 3 patients experienced AEs that were considered to be severe (all of which were considered related to the study medication) and all recovered from these events. Amongst these, one patient randomised to the 640 µg Locteron™ dose experienced a SAE, being hospitalised with otitis and neutropenia. No deaths occurred during the study and only one patient was discontinued from the study due to AE. The most frequently experienced AEs by system organ class were musculoskeletal and connective tissue disorders and administrative site conditions. By preferred term, the most frequently experienced AEs were asthenia, arthralgia and headache. No notable differences were observed between treatment groups in the frequency and occurrence of AEs, with the exceptions of neutropenia and leukopenia, where a higher frequency of patients in the 640 µg group experienced these events than in all other dose groups. The most frequently experienced influenza-like symptom was asthenia, with the highest frequency of patients experiencing such a symptom being in the 640 µg treatment group. Headache was the next most experienced influenza-like symptom and was also the most frequently experienced influenza-like symptom at any one visit. The symptoms with the longest mean durations during the study were headache and myalgias. No notable patterns in the frequency and duration of influenza-like symptoms were observed between treatment groups during the study, however, there was a general trend of higher frequencies of such events in the 640 µg treatment group compared with the other treatment groups.

The haematology laboratory parameters did not give rise to any significant safety concerns with the majority of mean values being within the normal reference ranges. However, there were exceptions where a few haematology parameters had values that did not remain within the normal reference ranges for the duration of the study. Of note, the mean values of WBC, HGB, ABS neutrophils, monocytes and MCHC were all outside of the normal reference ranges for at least one visit during the study and high frequencies of high and low values were observed for MCHC, ABS neutrophils, neutrophils, RBC, HGB, monocytes, lymphocytes, MCV, basophils and MCH. Similarly, the majority of biochemistry parameters remained within normal reference ranges during the study, with exceptions of note being ALT, AST, total protein and uric acid. High frequencies of high and low values were observed for urea, ALT, AST, total protein and total cholesterol. However, it should be noted that although certain biochemistry parameters, such as ALT and AST had values outside of the normal range, these values were higher at the screening visit than at any other time during the study, an observation which is to be expected in patients with HCV. Indeed, high ALT was an inclusion criterion for this study, as was high AST, until this criterion was removed in Protocol Amendment 1.

Clinically significant changes in laboratory parameters were observed during the study, but only for a small frequency of those laboratory parameters exhibiting values outside of the normal reference ranges. Of all the haematology, biochemistry and urinalysis parameters, those parameters most frequently reported as AEs during the study were neutrophil count decreased, WBC count decreased and RBC count decreased, with the highest frequency of occurrences being reported for neutrophil count decreased (8 patients [25%]). However, no notable differences in the frequency and occurrence of laboratory abnormalities reported as AEs were observed between the treatment groups.

No safety concerns were raised by any other safety assessments; the majority of physical examination findings were normal, with the exceptions of the abdomen and skin body systems, and the majority of patients had normal or abnormal but not clinically significant ECG at all time points. At each visit, the majority of patients did not experience injection site reactions, but of those who did, the most frequent reaction was redness. No notable differences in the frequency and occurrence of injection site reactions were observed between treatment groups.

The HCV RNA levels of patients were assessed after 4 weeks (Week 5/Day 29) and 12 weeks (Week 13/Day 85) of Locteron™ treatment during the study. It was observed that greater frequencies of patients in the higher Locteron™ treatment groups tended to have greater decreases in HCV RNA levels. After 4 weeks, mean log drops of HCV RNA amounted to 3.21, 2.97 and 3.20 in the 320 µg, 480 µg and 640 µg treatment groups, respectively, while the mean log drop in the 160 µg group was 1.05. After 12 weeks (Week 13/Day 85), the majority of patients (25 patients [78.1%]) had at least a two log drop in HCV RNA levels. Also at this time point, the lowest number of patients achieving these log drops were in the lowest treatment group (160 µg). In contrast, the majority of patients in the 320 µg, 480 µg and 640 µg treatment groups achieved at least a log drop after 4 weeks and at least a two log drop after 12 weeks. A similar trend across treatment groups was observed when assessing HCV RNA eradication after 12 weeks. Only one patient (12.5%) had HCV RNA eradication in the lowest treatment group (160 µg) after 12 weeks but the majority of patients in the 320 µg, 480 µg and 640 µg treatment groups did achieve HCV RNA eradication after 12 weeks. Similarly, the lowest mean log decrease after 12 weeks was seen in the 160 µg treatment group (−1.86) in comparison to the higher log decreases of the 320 µg (−4.66), 480 µg (−4.41) and 640 µg (−4.89) treatment groups. These results demonstrate that Locteron™ induces greater reduction in HCV RNA at the 320 µg, 480 µg and 640 µg dose levels, with the least effect being observed in the lowest treatment group (160 µg).

Considerable variability was associated with the measured IFNα2b, 2',5'-OAS and neopterin serum concentrations mainly between, but also within patients, for all doses. Given this, the planned number of patients (N=32, 8 in each dose level) was probably not adequate for fulfilling the objectives of the analyses using either model independent methods or non-linear mixed effects modelling.

Following the 160 µg and 320 µg doses, the majority of the patients had IFNα2b serum concentrations <2.5 pg/mL for the first 24 h post first dose and after that time mean profiles were flat and appear superimposable. Following the 480 µg and the 640 µg doses, mean IFNα2b serum concentrations rose until about 168 h post first dose and then declined. The time $C_{max}$ was observed following the first dose was quite variable and was not associated with dose.

Baseline 2',5'-OAS data were quite variable, means were similar for dose levels 160 to 480 µg but slightly lower for the 640 µg dose level. $D_{max}$ was achieved between Day 4 to Day 8 and increased with dose; as did $D_{min}$, $AUEC_{0-7Days}$ and $AUEC_{0-14Days}$. Baseline neopterin data were less variable than for 2',5'-OAS for the 320, 480 and 640 µg dose groups, with similar means. $D_{max}$, $D_{min}$, $AUEC_{0-7Days}$ and $AUEC_{0-14Days}$ increased with dose for doses 160 µg to 480 µg, while the estimates of these parameters for the 640 µg dose level were slightly lower than for the 480 µg dose level.

Statistical assessment of dose proportionality indicated that the 90% CI for the slope of the regression of the dose-dependent $^e$log-transformed IFNα2b parameters $AUC_{last}$ and $C_{max}$ vs. $^e$log dose included 1, therefore dose proportionality was concluded, however these parameters for the 160 µg dose group were generally higher than predicted. This might be due to the fact that one of the patients receiving this treatment had IFNα2b concentrations <2.5 pg/mL at all times and thus was excluded from the analysis (Patient 03/08).

An $E_{max}$ model incorporating a measured baseline effect on $E_0$ adequately described the neopterin vs. IFNα2b relationship, however, variability on $E_{max}$ was not estimable. For neopterin, the population estimates for the IFNα2b $C_{50}$ and $E_{max}$ were 31.8 pg/mL and 13.2 nmol/L, respectively, while for $E_0$ it was 5.90 nmol/L, with 60% of it depending on the measured baseline. For neopterin, inter-individual variability in $C_{50}$ and $E_0$ was 54% and 10%, respectively, while residual variability, a composite of model misspecification, assay variability and intra-subject vaiability was 21%.

In the screening method for anti-IFNα activity binding antibodies, anti-IFNα(BAB), the majority (19 patients) were negative at all assessments. Of the samples from the 13 patients with either positive or equivocal results in the binding assay, only 2 tested positive in the neutralisation assay, one in the 160 µg group and one in the 640 µg group. The patient in the 160 µg group was positive at baseline, prior to dosing. In a subsequent SPR assay on a BiaCore 2000® instrument, antibodies were detected in only one sample from the patient receiving the 640 µg dose, i.e. after last visit (Visit 16/Day 92). The antibodies in that sample were considered to be of low affinity. The immune response was mediated by IgG antibodies, mainly of IgG1 subclass, followed by IgG2.

Overall Conclusions

The safety assessment of Locteron™ showed that although 96.9% of patients experienced AEs, only 1 patient was withdrawn due to AE, only 3 patients experienced AEs considered severe and related to study medication, and only one patient in the 640 µg treatment group experienced an SAE. No deaths occurred.

The majority of laboratory parameters (haematology, biochemistry, urinalysis) were within normal ranges throughout the study.

Clinically significant changes in laboratory parameters were observed, but only for a small frequency of those laboratory parameters exhibiting values outside of the normal reference ranges, with neutrophil count decreased being the most prevalent, and no notable differences between the treatment groups.

Locteron™, at doses of 160 µg, 320 µg, 480 µg and 640 µg induced 1.05, 3.21, 2.97 and 3.20 mean log drops in HCV RNA, respectively, after 4 weeks. Locteron™-induced at least a two log drop after 12 weeks in HCV RNA levels in the majority of patients in the 320 µg, 480 µg and 640 µg treatment groups, with the lowest frequency being in the 160 µg treatment group.

Greater overall mean log decreases were seen in the 320 µg, 480 µg and 640 µg Locteron™ dose groups; the lowest mean log decrease was seen in the lowest Locteron™ treatment group (160 µg). After 12 weeks, log drops in HCV RNA in the 160 µg, 320 µg, 480 µg and 640 µg treatment groups were 1.86, 4.66, 4.41 and 4.89, respectively.

A greater frequency of patients experiencing Locteron™ induced HCV RNA eradication was observed than no eradication in the 320 µg, 480 µg and 640 µg treatment groups, but no such effect was seen in the lowest treatment group (160 µg).

Considerable inter- and intra-patient variability was associated with the measured IFNα2b, 2',5'-OAS and neopterin serum concentrations.

The increase in $AUC_{last}$ and $C_{max}$ IFNα2b parameters was dose proportional.

For 2',5'-OAS, maximum change from baseline was achieved between Days 4 and 8, and increased with the Locteron™ dose, as did the minimum change and the areas under the serum concentration-time profiles to 7 days and 14 days.

For neopterin, maximum change from baseline was achieved at approximately Day 4, and the minimum change of baseline at Day 15. Maximum and minimum changes from baseline and the areas under the serum concentration-time profiles to 7 days and 14 days increased with Locteron™ dose from 160 µg to 480 µg, whilst estimates for the 640 µg dose were slightly lower than those for the 480 µg dose.

Following a screening method for anti-IFNα activity binding antibodies, 2 patients tested positive in the neutralisation assay, one in the 160 µg group and one in the 640 µg group. The patient in the 160 µg group was positive at baseline, prior to dosing. In the BiaCore® assay system, the antibodies in the sample from the patient receiving 640 µg dose, i.e. after last visit (Visit 16/Day 92) were considered to be of low affinity.

Example 5

Comparison of the Formulations Used in Phase I and Phase II Studies

As discussed supra, the major difference between the two studies is the release profile of the active ingredient from the controlled release interferon formulations used in the two studies (i.e., Product A and Product B described above). For example, FIGS. 14A and 14B show, respectively, cumulative and daily release of INF-α from the controlled release interferon formulations used in the two studies (phase I and phase II). As can clearly be seen, the two controlled release formulations used in Phase I and Phase II studies follow completely difference release kinetics. For example, the release of the INF-α from the phase II formulation is sigmoidal in nature whereas the release of the INF-α from the phase I formulation is not.

Example 6

Comparison of Phase II Trial to Pegasys, Albuferon, and PEG-Intron (I) Severe Adverse Events FIG. 15 compares incidence of clinical events rated as severe in LOCTERON clinical Phase II trial to published results for Pegasys and Albuferon reported by Zeuzem, et al. at the 2006 Annual European Association for the Study of the Liver meeting.

(a) Locteron Data

The results for "Locteron—all cohorts" represent the results for all 32 patients in the SELECT-1 Phase 2a clinical trial: eight patients in each of the 160 µg, 320 µg, 480 µg and 640 µg cohorts. The results for "Locteron—480 µg cohort" represent the results for the eight patients in the 480 µg dose cohort of the SELECT-1 Phase 2a clinical trial. The 480 µg cohort is shown separately as this cohort was within the middle of the three doses (320 µg, 480 µg and 640 µg) for which the results suggested a favourable balance between viral response and tolerability.

(b) Pegasys and Albuferon Data

The percentages presented for Pegasys and Albuferon were from the presentation of Zeuzem, et al., 2006 Annual European Association for the Study of the Liver meeting. Patients included in the Zeuzem trial were 114 for Pegasys and 110 and 118 for Albuferon 900 and 1200 µg dose cohorts, respectively. Adverse events that were reported as severe were defined as "interferon related," therefore certain severe adverse events determined not to be interferon related may have been excluded. Adverse events rated as severe after 48 weeks of treatment as reported in Zeuzem, et al., 2007 Annual European Association for the Study of the Liver meeting were 27%, 31% and 41% for the Pegasys and Albuferon 900 and 1200 µg dose cohorts, respectively.

(II) Fever

FIG. 16 compares incidence of fever in LOCTERON clinical Phase II trial to published results for Pegsys, Albuferon, and PEG-Intron.

(a) Locteron Data

The results for "Locteron—all cohorts" represent the results through 12 weeks of treatment for all 32 patients in the SELECT-1 Phase 2a clinical trial: eight patients in each of the 160 µg, 320 µg, 480 µg and 640 µg cohorts. Four of the six incidents of fever occurred in the 640 µg cohort. The results for "Locteron—480 µg cohort" represent the results through 12 weeks of treatment for the eight patients in the 480 µg dose cohort of the SELECT-1 Phase 2a clinical trial. The 480 µg cohort is shown separately as this cohort was within the middle of the three doses (320 µg, 480 µg and 640 µg) for which the results suggested a favorable balance between viral response and tolerability.

(b) PEG-Intron Data

The data for PEG-Intron are results through 48 weeks of treatment reported in PEG-Intron package insert.

(c) Pegasys Data

The data for Pegasys are results through 48 weeks of treatment reported in Pegasys package insert.

(d) Albuferon Data

The data for Albuferon are results through four weeks of treatment reported in Bain, et al., *Journal of Hepatology* (2006) 1-8. Patients included in trial were 12 and 14 for Albuferon 900 and 1200 µg dose cohorts, respectively.

Example 7

Further Studies with Product B

In addition to the phase II trial, in a separate trial 16 treatment-experienced HCV patients were divided into two cohorts (eight each) and were administered either LOCTERON 320 µg or PEG-Intron. One objective of this trial was to determine whether the reduction of adverse events observed with the treatment naïve subjects in the phase II trial was also achieved when LOCTERON is administered to treatment-experienced patients. Preliminary results indicate that treatment-experienced patients also suffer from fewer adverse events when administered Locteron 320 µg vis-à-vis patients receiving PEG-Intron (see Table 21).

TABLE 21

Flu-Like Adverse Events for treatment-experienced subjects when administered either a PEG-interferon or LOCTERON 320 µg

| | Dose Group: Number of 8 (%) | |
| --- | --- | --- |
| Flu-Like Adverse Event | PEG-Intron (N = 8) | Locteron (N = 8) |
| Arthralgia | 4 (50) | 1 (12.5) |
| Chills (rigors) | 6 (75) | 1 (12.5) |

TABLE 21-continued

Flu-Like Adverse Events for treatment-experienced
subjects when administered either a PEG-interferon
or LOCTERON 320 μg

| Flu-Like Adverse Event | Dose Group: Number of 8 (%) | |
|---|---|---|
| | PEG-Intron (N = 8) | Locteron (N = 8) |
| Fever (pyrexia; T ≧ 38.0° C.) | 5 (62.5) | 3 (37.5) |
| Headache | 7 (87.5) | 5 (62.5) |
| Myalgia | 6 (75) | 4 (50) |

All flu-like symptoms reported in the LOCTERON 320 μG group were mild in intensity. In the PEG-Intron group 2 subjects had severe headache, 1 had severe myalgia. Moderate intensity flu-like adverse events were reported in the PEG-Intron group as follows: Arthralgia (3/8), Chills (3/8), Fever (3/8), Headache (4/8), Myalgia (4/8).

Table 22. lists flu-Like adverse events for treatment-experienced subjects when administered either a PEG-interferon or LOCTERON 640 μg.

TABLE 22

Flu-Like Adverse Events for treatment-experienced
subjects when administered either a PEG-interferon
or LOCTERON 640 μg

| Flu-Like Adverse Event | Dose Group: Number of 8 (%) | |
|---|---|---|
| | PEG-Intron (N = 8) | Locteron (N = 8) |
| Arthralgia | 5 (62.5) | 5 (62.5) |
| Chills (rigors) | 5 (62.5) | 5 (62.5) |
| Fever (pyrexia; T ≧ 38.0° C.) | 5 (62.5) | 2 (25) |
| Headache | 5 (62.5) | 4 (50) |
| Myalgia | 7 (87.5) | 5 (62.5) |

All flu-like symptoms reported in the Locteron 640 μg group were mild to moderate in intensity. In the PEG-Intron group the flu-like symptoms were mild, moderate and 3 severe: 1 subject had severe chills, 1 had severe headache, and 1 had severe myalgia.

The invention claimed is:

1. A method of treating acute or chronic hepatitis C comprising administering to treatment naive subjects in need thereof a controlled release formulation comprising a microsphere comprising a biodegradable polymer and interferon-α2b encapsulated by or dispersed in the biodegradable polymer, wherein the Cmax of said interferon-α2b in the blood plasma is reached after about 48 hours after initial administration of the formulation and said formulation is administered no more than once every two weeks, wherein the interferon-α2b is present in an amount of about 0.2 wt % to about 10 wt % of the microsphere and at least about 100 MIU per dose, wherein said formulation is administered in combination therapy with ribavirin, wherein at least 80% of the subjects exhibit more than two log reduction in HCV RNA 12 weeks after initial administration of the formulation, and wherein greater than 80% of the flu-like symptoms that occur in the subjects are mild.

2. The method of claim 1, wherein the interferon-α2b is a C-terminally truncated interferon.

3. The method of claim 1, wherein the interferon-α2b is released from the microparticle in a sigmoidal pattern.

4. The method of claim 1, wherein the biodegradable polymer is a block copolymer comprising a poly(ethylene glycol) terephthalate) segment and a poly(butylene terephthalate) segment.

5. The method of claim 1, wherein less than 5% of the subjects experience adverse severe events.

6. The method of claim 1, wherein pyrexia occurs in less than 25% of the subjects.

7. The method of claim 1, wherein the interferon-α2b is present in an amount of at least about 150 MIU per dose and wherein at least 90% of the subjects exhibit more than a two log reduction in HCV RNA 12 weeks after initial administration of the formulation.

8. The method of claim 7, wherein the interferon-α2b is a C-terminally truncated interferon.

9. The method of claim 7, wherein the interferon-α2b is released from the microparticle in a sigmoidal pattern.

* * * * *